(12) United States Patent
Furusako et al.

(10) Patent No.: US 8,124,722 B2
(45) Date of Patent: *Feb. 28, 2012

(54) SOLUBLE CD14 ANTIGEN

(75) Inventors: Shoji Furusako, Shizuoka (JP); Kamon Shirakawa, Shizuoka (JP); Jiro Hirose, Kanagawa (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 353 days.

This patent is subject to a terminal disclaimer.

(21) Appl. No.: 12/395,298

(22) Filed: Feb. 27, 2009

(65) Prior Publication Data

US 2009/0203052 A1 Aug. 13, 2009

Related U.S. Application Data

(60) Division of application No. 11/126,344, filed on May 11, 2005, now Pat. No. 7,608,684, which is a continuation-in-part of application No. 10/534,257, filed as application No. PCT/JP03/14389 on Nov. 12, 2003, now Pat. No. 7,465,547.

(30) Foreign Application Priority Data

Nov. 12, 2002 (JP) ................................ 2002-328866
Sep. 22, 2003 (JP) ................................ 2003-330775
May 11, 2004 (JP) ................................ 2004-141600

(51) Int. Cl.
*A61K 38/00* (2006.01)
*C07K 1/00* (2006.01)

(52) U.S. Cl. ......... 530/300; 530/324; 530/333; 530/344
(58) Field of Classification Search ....................... None
See application file for complete search history.

(56) References Cited

U.S. PATENT DOCUMENTS 4,931,385 A 6/1990 Block et al.
(Continued)

FOREIGN PATENT DOCUMENTS

DE 286 876 A5 10/1983
(Continued)

OTHER PUBLICATIONS

ATCC Catalog page of 3C10 (ATCC No. TIB-228). Aug. 30, 2006. pp. 1-2.*

(Continued)

*Primary Examiner* — Chun Dahle
(74) *Attorney, Agent, or Firm* — Birch, Stewart, Kolasch & Birch, LLP

(57) ABSTRACT

There are provided a soluble CD14 antigen which is a novel in vivo protein useful as a marker for diagnosing sepsis and has the following characteristic features 1) to 3):
1) a molecular weight of 13±2 kDa when measured by SDS-PAGE under non-reducing conditions;
2) an amino acid sequence in which the amino acid sequence of SEQ ID NO:1 is present on its N terminal; and
3) ability to specifically bind to an antibody prepared by using a peptide comprising 16 amino acid residues described in SEQ ID NO:2 for the antigen;
and a recombinant soluble CD14 fragment.

2 Claims, 10 Drawing Sheets

U.S. PATENT DOCUMENTS

| | | | |
|---|---|---|---|
| 5,766,593 | A | 6/1998 | Lichenstein et al. |
| 6,916,628 | B1 | 7/2005 | Furusako et al. |
| 7,326,569 | B2 | 2/2008 | Leturcq et al. |
| 7,465,547 | B2 * | 12/2008 | Furusako et al. ............ 435/7.1 |
| 2004/0141917 | A1 | 7/2004 | Achen et al. |

FOREIGN PATENT DOCUMENTS

| | | |
|---|---|---|
| EP | 1 213 586 A1 | 6/2002 |
| EP | 1 275 713 A1 | 1/2003 |
| EP | 1336620 A1 | 8/2003 |
| EP | 1 571 160 A1 | 9/2005 |
| JP | 2005-106694 A | 4/2005 |
| WO | WO-96/20956 A1 | 7/1996 |
| WO | WO-01/22085 A1 | 3/2001 |
| WO | WO-01/72993 A1 | 10/2001 |
| WO | WO-02/42333 A1 | 5/2002 |

OTHER PUBLICATIONS

Landmann, Regine et al.; The Journal of Infectious Disease; vol. 171, pp. 639-644 (1995).

Stelter, Felix et al.; European Journal of Biochemistry, vol. 236, pp. 457-464 (1996).

Juan, Todd S.-C. et al.; The Journal of Biological Chemistry; vol. 270, No. 3, pp. 1382-1387 (1995).

Majerle, Andreja et al., European Journal of Physiology; vol. 439 [Suppl.], pp. R109-R110 (2000).

Bazil, Vladimir et al.; European Journal of Immunology, vol. 16, pp. 1583-1589 (1986).

Schuett, Christine et al., Allerg. Immunol., vol. 34, pp. 17-26 (1988) (Summary at p. 17 in English).

van Voorhis, Wesley C. et al., Journal of Experimental Medicine; vol. 158, pp. 126-145 (1983).

Bazil, Vladimir et al., Molecular Immunology, vol. 26, No. 7, pp. 657-662 (1989).

Grunwald, U. et al., Journal of Immunological Methods, vol. 155, pp. 225-232 (1992).

Burgmann, Heinz et al., Clinical Immunology and Immunopathology, vol. 80, No. 8, pp. 307-310 (1996).

Endo et al., The Japanese Association for Infectious Diseases, the 52nd East Japan Meeting held on Oct. 31, 2003 Abstract No. 123 (with English translation).

Endo et al., Journal of Japanese Association for Acute Medicine, vol. 14, No. 10, p. 602 (Oct. 2003) (with English translation).

The Official Journal of the Shock Society, Abstract of the 6th World Congress on Trauma, Shock, Inflammation and Sepsis (Mar. 2004).

Endo et al., Journal of the Japanese Society of Intensive Care Medicine, vol. 11 Supplement, p. 244 (Jan. 2004) (with English translation).

The Official Journal of the Critical Care Forum, vol. 8, Supplement 1, pp. S94-S95 (Mar. 2004).

Abstract in the 104th General Assembly of the Japan Surgical Society (Apr. 2004); (with English translation).

Official Journal of the European Society of Intensive Care Medicine and the European Society of Paediatric & Neonatal Intensive Care, vol. 30, Supplement 1, p. S192 (Sep. 2004).

Endo et al., Program and Abstracts of the 10th Conference of the Japan Endotoxin Society, Nov. 15, 2004 (with English translation).

Journal of Endotoxin Research, vol. 10, No. 5, p. 373 (Nov. 2004).

Endo et al., Journal of the Japanese Society of Intensive Care Medicine, vol. 12 Supplement, p. 121 (Jan. 2005) (with English translation).

Endo et al., The Journal of the Japanese Association of Infectious Diseases, vol. 80 Supplement, p. 271, (Mar. 2006) (with English translation).

Endo et al., Japan Journal of Critical Care for Endotoxemia, vol. 9, No. 1, pp. 46-50 (2005) (English translation is on p. 50).

Yaegashi et al., J .Infect. Chemother. , vol. 11, pp. 234-238 ( Mar. 2005).

Manocha, Sanjay et al.; Expert Opinion Investig. Drugs; vol. 11, No. 12, pp. 1795-1812 (2002).

Yaegashi et al., "Evaluation of a newly identified soluble CD14 subtype as a marker for sepsis, " J Infect Chemother (2005), vol. 11 , pp. 234-238.

Bufler et al., "Soluble lipopolysaccharide receptor (CD14) is released via two different mechanisms from human monocytes and CD14 transfectants, " Eur. J. Immunol, 1995, vol. 25, pp. 604-610.

Majerle et al., "Bacterial expression and refolding of different fragments of human CD14," Pflugers Arch:Eur J Physiol (2000) vol. 439 (Suppl): R109-R110.

Majerle et al., "Expression and Refolding of Functional Fragments of the Human Lipopolysaccharide Receptor CD14 in *Escherichia coli* and *Pichia pastoris*, " Protein Expression and Purification, vol. 17, pp. 97-104 (1999).

Stelter et al., "Mutation of amino acids 39-44 of human CD14 abrogates binding of lipopolysaccharide and *Escherichia coli*," Eur. J. Biochem., vol. 243, pp. 100-109, (1997).

Iwaki et al., "The CD14 region spanning amino acids 57-64 is critical for interaction with the extracellular Toll-like receptor 2 domain, " Biochemical and Biophysical Research Communications, vol. 328, (2005), pp. 173-176.

D. Levenson, Clinical Laboratory News Jan. 2008, vol. 34, No. 1, [retrieved on Feb. 12, 2008]. Retrieved from the Internet: URL: http://www.aacc.org/AACC/publications/cln/2008/jan/cover1_0108.htm, p. 1-8.

C. Wenisch et al., "Elevated levels of soluble CD14 in serum of patients with acute *Plasmodium falciparum malaria*," Clin. Exp. Immunol. 1996, vol. 105, pp. 74-78.

E. Lien et al., "Elevated Levels of Serum-Soluble CD14 in Human Immunodeficiency Virus Type 1 (HIV-1) Infection: Correlation to Disease Progression and Clinical Events," Blood, vol. 92, No. 6, pp. 2084-2092, Sep. 1998.

Coleman et al., Research in Immunology, 1994; 145(1): 33-36.

Abaza et al., Journal of Protein Chemistry, vol. 11, No. 5, 1992, pp. 433-444.

Lenderman et al., Molecular Immunology, 1991, 28: 1171-1181.

Li et al., PNAS, 1980, 77: 3211-3214.

Kim et al., JBC 2005, 280:11347-11351.

Haziot et al., The Journal of Immunology, 1988, 141:547-552.

Office Action dated Apr. 7, 2010 for U.S. Appl. No. 11/987,746.

* cited by examiner 1  2

1 : PSP64 PURIFIED SAMPLE
2 : 2ST64 PURIFIED SAMPLE sCD14-ST    2ST64    PSP64

←12.9kDa
←12.6kDa

SOLUBLE CD14 ANTIGEN

This is a Divisional of application Ser. No. 11/126,344 filed on May 11, 2005, now U.S. Pat. No. 7,608,684, and for which priority is claimed under 35 U.S.C. §120. Application Ser. No. 11/126,344 is a continuation-in-part of application Ser. No. 10/534,257, now U.S. Pat. No. 7,465,547, filed under 35 U.S.C. §120 on May 10, 2005, and is the National Stage Application of PCT International Application No. PCT/JP2003/14389 filed on Nov. 12, 2003, which claims the benefit of priority of Japanese Application No. 2003-330775 filed on Sep. 22, 2003 and Japanese Application No. 2002-328866 filed on Nov. 12, 2002 under 35 U.S.C. §119. Application Ser. No. 11/126,344 also claims the benefit of priority to Japanese Application No. 2004-141600 filed on May 11, 2004 under 35 U.S.C. §119. The contents of all of the aforementioned applications are incorporated herein by reference.

BACKGROUND OF THE INVENTION

1. Technical Field

The present invention relates to a novel in vivo antigen which can serve as a diagnostic marker for sepsis. The invention also relates to a method for diagnosing the sepsis characterized by assaying the antigen, and an assay kit and an assay method for the antigen using a particular antibody. The invention further relates to a recombinant soluble fragment useful as a standard substance of the assay kit, an antibody binding to the fragment, a method for producing the fragment, and an antibody screening method using the fragment.

2. Background Art

A CD14 molecule was named as a protein identified by a family of antibodies that recognize glycoproteins expressed on the membrane surface of monocytes in Third Leukocyte Typing Conference, 1986. In 1990, Wright et al. elucidated that the CD14 molecule is a receptor for LPS, endotoxin ("Science", vol. 249, p. 1431-1433, 1990). The CD14 molecule is a glycoprotein having a molecular weight of 53-55 kDa, and analyses on cDNA revealed that mRNA of about 1.4 kb has coding sequence of 356 amino acids ("Nucleic Acids Research" (U.K.), vol. 16, p. 4173, 1988).

It was reported that human CD14 molecules include soluble CD14 molecules in addition to membrane-bound CD14 molecules and blood contains soluble CD14 molecules having different molecular weights ("European Journal of Immunology" (Germany), vol. 23, p. 2144-2151, 1993). In addition, Landmann et al. conducted Western blot analyses on soluble CD14 in serum of patients suffering from sepsis and reported that soluble CD14 of about 55 kDa is at high levels in non-survival sepsis patients and patients with paroxysmal nocturnal hemoglobinuria (PNH) and that in normal sera, this molecule was not detected but soluble CD14 of 49-kDa, a slightly lower molecular weight than the former, was detected ("The Journal of Infectious Disease" (U.S.A.), vol. 171, p. 639-644, 1995).

Stelter et al. reported that the difference in sugar chains is involved in those subtypes having different molecular weights and two soluble CD14 subtypes having different molecular weights are found in blood even after removal of N- and O-linked sugar chains ("European Journal of Biochemistry" (Germany), vol. 236, p. 457-464, 1996). In addition, Bufler et al. conducted the C-terminal analysis on soluble CD14 and reported that a GPI anchored to a serine residue at position 327 of soluble CD14 and that a soluble CD14 molecule having a molecular weight of about 56 kDa is one of the molecular species from which GPI is not anchored ("European Journal of Immunology" (Germany), vol. 25, p. 604-610, 1995).

Concerning recombinant full length soluble CD14 and a fragment thereof, Juan et al. reported that an N-terminal 1-152 fragment of human CD14 has a function of transmitting LPS signals to cells ("Journal of Biological Chemistry" (U.S.A.), vol. 278, p. 1382-1387, 1995), but they have not succeeded in expressing an N-terminal 1-124 fragment and an N-terminal 1-98 fragment. In addition, Majerle et al. reported that an N-terminal 1-152 fragment of human CD14 which includes 3 units of a leucine-rich repeat (LRR) region is refolded and an N-terminal 1-134 fragment of human CD14 which includes only two units of the LRR region is not refolded, and that they did not succeeded in expressing an N-terminal 1-69 fragment ("Pflugers Arch-European Journal of Physiology" (Germany), vol. 439 [Suppl], p. R109-R110, 2000), but according to the report, they have not succeeded in expressing an N-terminal 1-69 fragment.

Antibodies against CD14 molecules include many anti-CD14 antibodies, which have been prepared and used in identification of CD14 proteins, such as MEM-18 prepared by Bazil et al. ("European Journal of Immunology" (Germany), vol. 16, p. 1583-1589, 1986), RoMo-1 prepared by Shutt et al. ("Allergie und Immunologie" (Germany), vol. 34, p. 17-26, 1988), and 3C10 prepared by Steinman et al. ("Journal of Experimental Medicine" (U.S.A.), vol. 158, p. 126-145, 1983).

Furthermore, soluble-CD14 assay systems using those antibodies have been reported by Shutt et al. (DE-286876-A), Bazil et al. ("Molecular Immunology" (U.K.), vol. 26, p. 657-662, 1989), and Grunwald et al. ("Journal of Immunological Methods" (Holland), vol. 155, p. 225-232, 1992), allowing the assay of soluble CD14 in human body fluid.

Furthermore, soluble CD14-ELISA kits have been released on the market from IBL-Hamburg, Medgenix, and R & D Systems, and the assay of soluble CD14 has been performed for many diseases such as sepsis ("Clinical Immunology And Immunopathology" (U.S.A.), vol. 80, p. 307-310, 1996; and "Rinshokensa", vol. 38, p. 341-344, 1994).

However, it was found that soluble CD14 is not a sepsis-specific marker because of increases in levels of soluble CD14 molecules of about 55 kDa and 49 kDa (from report to report, the molecular weights are different and not limited to about 55 kDa and 49 ka, and the same will be applied in the following description) depending on the degree of progress of diseases even in diseases except sepsis ("Infection and Immunity" (U.S.A.), vol. 67, p. 417-420, 1999; "Clinical and Experimental Immunology" (U.K.), vol. 120, p. 483-487, 2000; and "Clinical Experimental Immunology" (U.K.), vol. 96, p. 15-19, 1994). Furthermore, the soluble CD14 was expected to be a marker for the severity of sepsis. However, the soluble CD14 has not been provided as a diagnostic product for sepsis because of no correlation with septic shock ("Pediatric allergy and immunology) (Denmark), vol. 8, p. 194-199, 1997) and also no correlation with systemic inflammatory response syndrome (SIRS) ("European Journal of Clinical Investigation" (U.K.), vol. 28, p. 672-678, 1998).

Further, there has been found out the presence of a soluble CD14 molecule with a low molecular weight of about 36 kDa in blood in addition to others such as two kinds of soluble CD14 molecules described above of about 55 kDa and 49 kDa reported by Landmann et al. (high molecular weight CD14 (from report to report, the molecular weights are different and not limited to about 55 kDa and 49 ka, and the same will be applied in the following description). There has been also found out the presence of a small amount of the low-molecular-weight CD14 in a normal donor and of an increased amount of the low-molecular-weight CD14 in patients suffering from sepsis. Consequently, the clinical efficacy of the assay on a soluble low-molecular-weight CD14 has been validated. As an assay for the soluble low-molecular-weight CD14, there is a proposal in which the level of low-molecular-weight CD14 in blood is indirectly obtained by subtracting the level of high molecular weight CD14 in blood from the total level of the soluble CD14 in blood (International publication WO 01/22085).

SUMMARY OF THE INVENTION

In view of such situation, a novel in vivo antigen which can serve as an easily detectable diagnostic marker for sepsis is highly awaited. Also, an assay kit and an assay method for the antigen using a particular antibody are highly awaited. Furthermore, a method for screening for an antibody which is useful in assay the antigen is awaited. Still further, a recombinant soluble fragment having the immunological function similar to the antigen as well as its production method are awaited.

After an extensive investigation, the inventors of the present invention found a novel antigen which has the sequence of the CD14 in human blood, and also, a method for diagnosing the sepsis or a method for detecting the sepsis which is accomplished by assaying the novel antigen.

The inventors also found a recombinant soluble fragment which has immunological nature similar to the antigen, and a method for producing the fragment, and also, an antibody which specifically binds to the fragment.

Furthermore, the inventors found an assay kit and an assay method which are capable of assaying various antigens, and the kit includes as its constituent "an antibody which specifically binds to a peptide comprising a particular amino acid sequence of the human full length soluble CD14" or a fragment thereof; "an antibody produced by using the peptide comprising a particular amino acid sequence of the human full length soluble CD14 for the antigen" or a fragment thereof; or "an antibody which specifically binds to the fragment" or a fragment thereof.

The inventors also found a method for screening for an antibody which is effective in assaying the antigen.

In the specification of the present invention, a "soluble CD14 antigen" can also be referred to as a "soluble CD14 protein". With regard to the "recombinant soluble CD14 fragment", while it can also be referred to as a "recombinant soluble CD14 protein", the term "fragment" is used herein to indicate that it has a partial sequence of the human full length soluble CD14. The term "fragment" is to be understood as in the case of the general technical term used in the art. In the present invention, the "fragment" designates a part of the analyte protein comprising a partial sequence of the amino acid sequence of the analyte protein, and difference in the protein conformation or in the addition of a sugar chain or a lipid from the analyte protein is not questioned.

The present invention provides the following (1) to (13).
(1) A soluble CD14 antigen which has the following characteristic features 1) to 3):
    1) a molecular weight of 13±2 kDa when measured by SDS-PAGE under non-reducing conditions;
    2) an amino acid sequence in which the amino acid sequence of SEQ ID NO:1 is present on its N terminal; and
    3) ability to specifically bind to an antibody prepared by using the peptide comprising 16 amino acid residues described in SEQ ID NO:2 for the antigen.

(2) A recombinant soluble CD14 fragment produced by the following steps i) to iii):
    i) the step of producing a fragment having a partial sequence of the amino acid sequence described in SEQ ID NO: 3 in which a sequence of a cleavage site for a predetermined protease has been substituted or inserted, or a fragment having such partial sequence in which 1 to 10 amino acids have been deleted, added, or substituted in the region other than positions 53 to 68 of SEQ ID NO: 3;
    ii) the step of cleaving the recombinant soluble CD14 fragment produced in i) with the predetermined protease; and
    iii) the step of recovering the fragment of the N terminal side cleaved in ii); and
having the following characteristic features 1) to 3):
    1) a molecular weight of 13±2 kDa when measured by SDS-PAGE under non-reducing conditions;
    2) no ability to specifically bind to 3C10 or MEM-18; and
    3) ability to specifically bind to an antibody prepared by using the peptide comprising 16 amino acid residues described in SEQ ID NO:2 for the antigen.

(3) A recombinant soluble CD14 fragment which has the following characteristic features 1) to 3):
    1) a molecular weight of 13±2 kDa when measured by SDS-PAGE under non-reducing conditions;
    2) no ability to specifically bind to 3C10 or MEM-18; and
    3) ability to specifically bind to an antibody prepared by using the peptide comprising 16 amino acid residues described in SEQ ID NO:2 for the antigen.

(4) A method for diagnosing or detecting sepsis in which the soluble CD14 antigen of the above (1) is assayed.
(5) A kit for assaying the soluble CD14 antigen of the above (1) in a specimen, the kit comprising at least one antibody which specifically binds to the soluble CD14 antigen of the above (1), or a fragment thereof.
(6) A method for immunologically assaying the soluble CD14 antigen of the above (1) in which at least one antibody which specifically binds to the soluble CD14 antigen of the above (1) or a fragment thereof is allowed to specifically bind to the soluble CD14 antigen of the above (1).
(7) An antibody which specifically binds to the soluble CD14 antigen of the above (1).
(8) An antibody which specifically binds to the recombinant soluble CD14 fragment of the above (2).
(9) An antibody which specifically binds to the recombinant soluble CD14 fragment of the above (3).
(10) A method for screening for an antibody which is useful in assay the soluble CD14 antigen of the above (1), said method comprising:
    1) the step of preparing for screening antibodies which specifically bind to a peptide comprising 6 to 20 consecutive amino acid residues selected from the amino acid sequence described in SEQ ID NO: 3;
    2) the step of preparing an analyte solution containing the CD14;
    3) the step of constituting an immunoassay system by using the antibodies prepared in 1) or the analyte solution prepared in 2);
    4) the step of assaying the analyte solution by using the immunoassay system constituted in 3); and
    5) the step of evaluating and selecting an antibody useful in assay the soluble CD14 antigen of the above (1) based on the assay result obtained in 4).
(11) A method for screening for an antibody which is useful in assay the soluble CD14 antigen of the above (1), said method comprising:

1) the step of preparing antibodies for screening;
2) the step of preparing the recombinant soluble CD14 fragment of the above (2);
3) the step of reacting the antibodies prepared in 1) with the fragment prepared in 2) to evaluate the specific binding between the antibodies prepared in 1) and the fragment prepared in 2); and
4) the step of selecting an antibody which underwent specific binding with the fragment prepared in 2) in step 3) as the antibody which is useful in assay the soluble CD14 antigen of the above (1).

(12) A method for producing the recombinant soluble CD14 fragment of the above (2) comprising:
(i) the step of producing a recombinant soluble CD14 fragment having the sequence characterized by the following 1) to 4):
1) a fragment having a partial sequence of the amino acid sequence described in SEQ ID NO: 3, or a fragment having the partial sequence in which 1 to 10 amino acids have been deleted, added, or substituted in the region other than positions 53 to 68 of SEQ ID NO: 3;
2) the N terminal is any one of positions 1 to 17 of SEQ ID NO: 3;
3) the C terminal is any one of positions 134 to 356 in SEQ ID NO: 3; and
4) a sequence of a cleavage site for a predetermined protease has been incorporated in the downstream of any one of positions 59 to 70 of SEQ ID NO: 3 by substitution or insertion;
(ii) the step of cleaving the recombinant soluble CD14 fragment prepared in (i) with the predetermined protease; and
(iii) the step of recovering the fragment of the N terminal side cleaved in ii).

Next, (1) to (13) of the present invention as described above are described in further detail.

The present invention provides a novel soluble CD14 antigen, a recombinant soluble CD14 fragment, and a novel method for diagnosing or detecting sepsis as described below.

(1) A novel soluble CD14 antigen of the following (1-1) or (1-2).
(1-1) A soluble CD14 antigen which has the following characteristic features 1) to 3):
1) a molecular weight of 13±2 kDa when measured by SDS-PAGE under non-reducing conditions;
2) an amino acid sequence in which the amino acid sequence of SEQ ID NO:1 is present on its N terminal; and
3) ability to specifically bind to an antibody prepared by using the peptide comprising 16 amino acid residues described in SEQ ID NO:2 for the antigen.
(1-2) A soluble CD14 antigen of (1-1) which also has the following characteristic feature 4):
4) capable of obtaining from human plasma.
(2) A recombinant soluble CD14 fragment of any one of the following (2-1) to (2-18).
(2-1) A recombinant soluble CD14 fragment produced by the following steps i) to iii):
i) the step of producing a fragment having a partial sequence of the amino acid sequence described in SEQ ID NO: 3 in which a sequence of a cleavage site for a predetermined protease has been substituted or inserted, or a fragment having the partial sequence in which 1 to 10 amino acids have been deleted, added, or substituted in the region other than positions 53 to 68 of SEQ ID NO: 3;
ii) the step of cleaving the recombinant soluble CD14 fragment produced in i) with the predetermined protease; and
iii) the step of recovering the fragment of the N terminal side cleaved in ii); and having the following characteristic features 1) to 3):
1) a molecular weight of 13±2 kDa when measured by SDS-PAGE under non-reducing conditions;
2) no ability to specifically bind to 3C10 or MEM-18; and
3) ability to specifically bind to an antibody prepared by using the peptide comprising 16 amino acid residues described in SEQ ID NO:2 for the antigen.
(2-2) A recombinant soluble CD14 fragment of the above (2-1) in which the recombinant soluble CD14 fragment produced in step i) of (2-1) has the sequence characterized by the following 4) to 7):
4) a fragment having a partial sequence of the amino acid sequence described in SEQ ID NO: 3, or a fragment having the partial sequence in which 1 to 10 amino acids have been deleted, added, or substituted in the region other than positions 53 to 68 of SEQ ID NO: 3;
5) the N terminal is any one of positions 1 to 17 of SEQ ID NO: 3;
6) the C terminal is any one of positions 134 to 356 in SEQ ID NO: 3;
7) the sequence of the cleavage site for the predetermined protease has been incorporated in the downstream of any one of positions 59 to 90 of SEQ ID NO: 3 by substitution or insertion.
(2-3) A recombinant soluble CD14 fragment of the above (2-2) in which the predetermined protease in step i)7) is PreScission Protease, and the sequence of the cleavage site is Leu, Glu, Val, Leu, Phe, Gln, Gly, Pro.
(2-4) A recombinant soluble CD14 fragment of the above (2-2) in which the predetermined protease in step i)7) is thrombin, and the sequence of the cleavage site is Leu, Val, Pro, Arg, Gly, Ser.
(2-5) A recombinant soluble CD14 fragment of any one of the above (2-2) to (2-4) in which, in step i)5), the N terminal is any one of positions 1 to 6 of SEQ ID NO: 3.
(2-6) A recombinant soluble CD14 fragment of any one of the above (2-2) to (2-4) in which, in step i)5), the N terminal is position 1 of SEQ ID NO: 3.
(2-7) A recombinant soluble CD14 fragment of any one of the above (2-2) to (2-6) in which, in step i)7), the sequence of the cleavage site for the predetermined protease has been incorporated in the downstream of any one of positions 59 to 80 of SEQ ID NO: 3 by substitution or insertion.
(2-8) A recombinant soluble CD14 fragment of any one of the above (2-2) to (2-6) in which, in step i)7), the sequence of the cleavage site for the predetermined protease has been incorporated in the downstream of any one of positions 64 to 75 of SEQ ID NO: 3 by substitution or insertion.
(2-9) A recombinant soluble CD14 fragment of any one of the above (2-2) to (2-6) in which, in step i)7), the sequence of the cleavage site for the predetermined protease has been incorporated in the downstream of position 64 of SEQ ID NO: 3 by substitution or insertion.
(2-10) A recombinant soluble CD14 fragment of any one of the above (2-2) to (2-4) in which, in step i)5), the N terminal is position 1 of SEQ ID NO: 3, and in step i)7), the sequence of the cleavage site for the predetermined protease has been incorporated in the downstream of position 64 of SEQ ID NO: 3 by substitution or insertion.
(2-11) A recombinant soluble CD14 fragment of the above (2-1) or (2-10) having the sequence characterized by the following 8) to 10):
8) a fragment having a partial sequence of the amino acid sequence described in SEQ ID NO: 3, or a fragment having the partial sequence in which 1 to 10 amino acids have been deleted, added, or substituted in the region other than positions 53 to 68 of SEQ ID NO: 3;

9) the N terminal is any one of positions 1 to 17 of SEQ ID NO: 3; and 10) the C terminal is any one of positions 59 to 90 in SEQ ID NO: 3.

(2-12) A recombinant soluble CD14 fragment of the above (2-11) in which, in 9), the N terminal is any one of positions 1 to 6 of SEQ ID NO: 3.

(2-13) A recombinant soluble CD14 fragment of the above (2-11) in which, in 9), the N terminal is position 1 of SEQ ID NO: 3.

(2-14) A recombinant soluble CD14 fragment of any one of the above (2-11) to (2-13) in which, in 10), the C terminal is any one of positions 59 to 80 of SEQ ID NO: 3.

(2-15) A recombinant soluble CD14 fragment of any one of the above (2-11) to (2-13) in which, in 10), the C terminal is any one of positions 64 to 75 of SEQ ID NO: 3.

(2-16) A recombinant soluble CD14 fragment of any one of the above (2-11) to (2-13) in which, in 10), the C terminal is position 64 of SEQ ID NO: 3.

(2-17) A recombinant soluble CD14 fragment of the above (2-11) in which, in 9), the N terminal is position 1 of SEQ ID NO: 3, and in 10), the C terminal is position 64 of SEQ ID NO: 3.

(2-18) A recombinant soluble CD14 fragment of any one of the above (2-1) to (2-18) further having the following characteristic feature 11):

11) no ability of binding to LPS.

(3) A recombinant soluble CD14 fragment of any one of the following (3-1) to (3-9).

(3-1) A recombinant soluble CD14 fragment which has the following characteristic features 1) to 3):

1) a molecular weight of 13±2 kDa when measured by SDS-PAGE under non-reducing conditions;

2) no ability to specifically bind to 3C10 and MEM-18; and 3) ability to specifically bind to an antibody prepared by using the peptide comprising 16 amino acid residues described in SEQ ID NO:2 for the antigen.

(3-2) A recombinant soluble CD14 fragment of the above (3-1) further having the following characteristic feature 4):

4) no ability of binding to LPS.

(3-3) A recombinant soluble CD14 fragment of the above (3-1) or (3-2) having the sequence characterized by the following 5) to 7):

5) a fragment having a partial sequence of the amino acid sequence described in SEQ ID NO: 3, or a fragment having the partial sequence in which 1 to 10 amino acids have been deleted, added, or substituted in the region other than positions 53 to 68 of SEQ ID NO: 3;

6) the N terminal is any one of positions 1 to 17 of SEQ ID NO: 3; and 7) the C terminal is any one of positions 59 to 90 in SEQ ID NO: 3.

(3-4) A recombinant soluble CD14 fragment of the above (3-3) in which, in 6), the N terminal is any one of positions 1 to 6 of SEQ ID NO: 3.

(3-5) A recombinant soluble CD14 fragment of the above (3-3) in which, in 6), the N terminal is position 1 of SEQ ID NO: 3.

(3-6) A recombinant soluble CD14 fragment of any one of the above (3-3) to (3-5) in which, in 7), the C terminal is any one of positions 59 to 80 of SEQ ID NO: 3.

(3-7) A recombinant soluble CD14 fragment of any one of the above (3-3) to (3-5) in which, in 7), the C terminal is any one of positions 64 to 75 of SEQ ID NO: 3.

(3-8) A recombinant soluble CD14 fragment of any one of the above (3-3) to (3-5) in which, in 6), the N terminal is position 1 of SEQ ID NO: 3, and in 7), the C terminal is any one of positions 64 to 75 of SEQ ID NO: 3.

(3-9) A recombinant soluble CD14 fragment of any one of the above (3-3) to (3-8) in which the fragment is the one having a partial sequence of the amino acid sequence described in SEQ ID NO: 3.

(4) A method for diagnosing sepsis of any one of the following (4-1) to (4-4).

(4-1) A method for diagnosing or detecting sepsis in which the soluble CD14 antigen of the above (1) is assayed.

(4-2) A method for diagnosing or detecting sepsis of the above (2-1) in which the method comprises the following steps of:

1) assaying the soluble CD14 antigen of the above (1) in the blood collected from a subject;

2) comparing the assayed value with the standard value for a normal donor; and 3) evaluating whether the subject has sepsis.

(4-3) A method for diagnosing or detecting sepsis of the above (2-2) in which the step 1) of assaying the soluble CD14 antigen is accomplished by an immunoassay.

(4-4) A method for diagnosing or detecting sepsis of the above (2-2) in which the step 1) of assaying the soluble CD14 antigen is accomplished by a sandwich immunoassay.

The present invention also provides a novel assay kit for the soluble CD14 antigen as well as a novel method for assaying the soluble CD14 antigen.

(5) A kit of any one of the following (5-1) to (5-8) for assaying the soluble CD14 antigen of the above (1).

(5-1) A kit for assaying the soluble CD14 antigen of the above (1) in a specimen, the kit comprising at least one antibody which specifically binds to the soluble CD14 antigen of the above (1), or a fragment thereof.

(5-2) A kit of the above (5-1) for assaying the soluble CD14 antigen, in which the antibody which specifically binds to the soluble CD14 antigen of the above (1) or a fragment thereof included in the kit is any one of the following antibodies a) to d) or a fragment thereof:

a) an antibody which specifically binds to a peptide comprising the amino acid residues described in SEQ ID NO: 2;

b) an antibody produced by using a peptide comprising 8 to 16 consecutive amino acid residues selected from the amino acid sequence described in SEQ ID NO: 2 for the antigen;

c) an antibody produced by using a peptide comprising 16 amino acid residues described in SEQ ID NO: 2 for the antigen; and d) an antibody which specifically binds to the recombinant soluble CD14 fragment of the above (2) or (3).

(5-3) A kit of the above (5-1) or (5-2) for assaying the soluble CD14 antigen, in which the antibody which specifically binds to the soluble CD14 antigen of the above (1) or a fragment thereof included in the kit is the antibody d) which specifically binds to the recombinant soluble CD14 fragment of the above (2) or (3) or a fragment thereof.

(5-4) A kit of any one of the above (5-1) to (5-3) for assaying the soluble CD14 antigen, in which the antibody which specifically binds to the soluble CD14 antigen of the above (1) or a fragment thereof included in the kit is an antibody produced by using the recombinant soluble CD14 fragment of the above (2) or (3) for the antigen, or a fragment thereof.

(5-5) A kit of any one of the above (5-1) to (5-4) for assaying the soluble CD14 antigen, in which the antibody which specifically binds to the soluble CD14 antigen of the above (1) or a fragment thereof included in the kit is a monoclonal antibody produced by using the recombinant soluble CD14 fragment of the above (2) or (3) for the antigen, or a fragment thereof.

(5-6) A kit of any one of the above (5-1) to (5-4) for assaying the soluble CD14 antigen, in which the soluble CD14 antigen of the above (1) is assayed by a sandwich immunoassay. The kit is any one of the following (5-6-1) to (5-6-19).

(5-6-1) A kit of any one of the above (5-1) to (5-4) for assaying the soluble CD14 antigen, in which the soluble CD14 antigen of the above (1) is assayed by a sandwich immunoassay.

(5-6-2) A kit of the above (5-6-1) for assaying the soluble CD14 antigen, which further comprises a second binding substance which specifically binds to the soluble CD14 antigen of the above (1).

(5-6-3) A kit of the above (5-6-2) for assaying the soluble CD14 antigen, in which the second binding substance is an antibody which specifically binds to the soluble CD14 antigen of the above (1), or a fragment thereof.

(5-6-4) A kit of the above (5-6-2) for assaying the soluble CD14 antigen, in which the second binding substance is a monoclonal antibody which specifically binds to the soluble CD14 antigen of the above (1).

(5-6-5) A kit of the above (5-6-2) for assaying the soluble CD14 antigen, in which the second binding substance is an antibody which specifically binds to any region in amino acid residues of positions 1 to 52 of the human full length soluble CD14 protein described in SEQ ID NO: 3, or a fragment thereof; or an antibody which shows competition or cross reactivity with an antibody which specifically binds to any region in amino acid residues of positions 1 to 52 of the human full length soluble CD14 protein described in SEQ ID NO: 3, or a fragment thereof.

(5-6-6) A kit of the above (5-6-2) for assaying the soluble CD14 antigen, in which the second binding substance is an antibody which specifically binds to any region in amino acid residues of positions 17 to 26 of the human soluble CD14 protein described in SEQ ID NO: 3, or a fragment thereof; or an antibody which shows competition or cross reactivity with an antibody which specifically binds to any region in amino acid residues of positions 17 to 26 of the human full length soluble CD14 protein described in SEQ ID NO: 3, or a fragment thereof.

(5-6-7) A kit of any one of the above (5-6-1) to (5-6-6) for assaying the soluble CD14 antigen, in which the antibody of any one of the above a) to d) or a fragment thereof is bonded to an insoluble carrier.

(5-6-8) A kit of any one of the above (5-6-2) to (5-6-6) for assaying the soluble CD14 antigen, in which the second binding substance is bonded to an insoluble carrier.

(5-6-9) A kit of any one of the above (5-6-1) to (5-6-6) and (5-6-8) for assaying the soluble CD14 antigen, in which the antibody of any one of the above a) to d) or a fragment thereof is labeled.

(5-6-10) A kit of any one of the above (5-6-1) to (5-6-7), in which the second binding substance is labeled.

(5-6-11) A kit of any one of the above (5-6-2) to (5-6-10) for assaying the soluble CD14 antigen, which further comprises a second specific binding substance which forms a second specific binding.

(5-6-12) A kit of the above (5-6-11) for assaying the soluble CD14 antigen, in which the binding partner of the second specific binding substance is the antibody of any one of the above a) to c) or a fragment thereof, or the second binding substance.

(5-6-13) A kit of the above (5-6-11) for assaying the soluble CD14 antigen, further comprising a partner of the second specific binding substance which binds to the second specific binding substance.

(5-6-14) A kit of any one of the above (5-6-11) to (5-6-13) for assaying the soluble CD14 antigen, in which the second specific binding substance which forms the second specific binding or the partner of the second specific binding substance is bonded to an insoluble carrier.

(5-6-15) A kit of any one of the above (5-6-11) to (5-6-13) for assaying the soluble CD14 antigen, in which the second specific binding substance which forms the second specific binding or the partner of the second specific binding substance is labeled.

(5-6-16) A kit of any one of the above (5-6-1) to (5-6-8) and (5-6-11) to (5-6-14) for assaying the soluble CD14 antigen, comprising a labeled soluble CD14 antigen of the above (1) or a labeled analog of the soluble CD14 antigen of the above (1), which is assayed by competitive sandwich immunoassay.

(5-6-17) A kit of any one of the above (5-6-9), (5-6-10), (5-6-15) and (5-6-16), for assaying the soluble CD14 antigen, in which the label is at least one member selected from enzyme, dye, gold colloid, colored latex, chemiluminescent substance, fluorescent substance, and isotope.

(5-6-18) A kit of any one of the above (5-6-16), for assaying the soluble CD14 antigen, in which the labeled analog of the soluble CD14 antigen of the above (1) is a labeled recombinant soluble CD14 fragment of the above (2).

(5-6-19) A kit of the above (5-6-2) for assaying the soluble CD14 antigen, in which the antibody of any one of a) to c) or a fragment thereof is bonded to an insoluble carrier, and the second binding substance is the antibody of d) or a fragment thereof.

(5-7) A kit of any one of the above (5-1) to (5-6) for assaying the soluble CD14 antigen, in which the assay is carried out by agglutination assay, solid phase direct assay, or competitive assay.

(5-8) A kit of any one of the above (5-1) to (5-7) for assaying the soluble CD14 antigen, further comprising the recombinant soluble CD14 fragment of the above (2) or (3) as a reference material.

(6) A method of any one of the following (6-1) to (6-3) for assaying the soluble CD14 antigen of the above (1).

(6-1) A method for immunologically assaying the soluble CD14 antigen of the above (1) in which at least one antibody which specifically binds to the soluble CD14 antigen of the above (1) or a fragment thereof is allowed to specifically bind to the soluble CD14 antigen of the above (1).

(6-2) A method for immunologically assaying the soluble CD14 antigen of the above (6-1), in which the antibody which specifically binds to the soluble CD14 antigen of the above (1) or a fragment thereof is any one of the following antibodies a) to d) or a fragment thereof:

a) an antibody which specifically binds to a peptide comprising the amino acid residues described in SEQ ID NO: 2;

b) an antibody produced by using a peptide comprising 8 to 16 consecutive amino acid residues selected from the amino acid sequence described in SEQ ID NO: 2 for the antigen;

c) an antibody produced by using a peptide comprising 16 amino acid residues described in SEQ ID NO: 2 for the antigen; and d) an antibody which specifically binds to the recombinant soluble CD14 fragment of the above (2) or (3).

(6-3) A method for immunologically assaying the soluble CD14 antigen of the above (6-2), in which a second binding substance which binds to the soluble CD14 antigen of the above (1) is used to assay the soluble CD14 antigen of the above (1) by a sandwich immunoassay between the antibody of any one of the above a) to c) or a fragment thereof and the second binding substance.

This invention also provides the following novel antibody and a method for screening for an antibody which is useful in assay the soluble CD14 antigen of the above (1).

(7) An antibody of any one of the following (7-1) to (7-4) which specifically binds to the soluble CD14 antigen of the above (1).

(7-1) An antibody which specifically binds to the soluble CD14 antigen of the above (1).

(7-2) An antibody of the above (7-1), which does not substantially bind to the full length soluble CD14 protein in human blood, but specifically binds to the soluble CD14 antigen of the above (1).

(7-3) An antibody of the above (7-1) or (7-2), which has been produced by using the recombinant soluble CD14 fragment of the above (2) for the antigen.

(7-4) An antibody of any one of the above (7-1) to (7-3), in which the antibody is a monoclonal antibody.

(8) An antibody of any one of the following (8-1) to (8-5) which specifically binds to the recombinant soluble CD14 fragment of the above (2).

(8-1) An antibody which specifically binds to the recombinant soluble CD14 fragment of the above (2).

(8-2) An antibody of the above (8-1), which does not substantially bind to the full length soluble CD14 protein in human blood, but binds to the recombinant soluble CD14 fragment of the above (2).

(8-3) An antibody of the above (8-1) or (8-2), which has been produced by using the recombinant soluble CD14 fragment of the above (2) for the antigen.

(8-4) An antibody of any one of the above (8-1) to (8-3), in which the antibody is a monoclonal antibody.

(8-5) An antibody of the above (8-4), in which the antibody is F1237-3-4 antibody.

(9) An antibody of any one of the following (9-1) to (9-4) which specifically binds to the recombinant soluble CD14 fragment of the above (3).

(9-1) An antibody which specifically binds to the recombinant soluble CD14 fragment of the above (3).

(9-2) An antibody of the above (9-1), which does not substantially bind to the full length soluble CD14 protein in human blood, but binds to the recombinant soluble CD14 fragment of the above (3).

(9-3) An antibody of the above (9-1) or (9-2), which has been produced by using the recombinant soluble CD14 fragment of the above (3) for the antigen.

(9-4) An antibody of any one of the above (9-1) to (9-3), in which the antibody is a monoclonal antibody.

(10) A method of any one of the following (10-1) to (10-13) for screening for an antibody which is useful in assay the soluble CD14 antigen of the above (1).

(10-1) A method for screening for an antibody which is useful in assay the soluble CD14 antigen of the above (1), said method comprising the steps of:

1) preparing for screening antibodies which specifically bind to a peptide comprising 6 to 20 consecutive amino acid residues selected from the amino acid sequence described in SEQ ID NO: 3;

2) preparing an analyte solution containing the CD14;

3) constituting an immunoassay system by using the antibodies prepared in 1) or the analyte solution prepared in 2);

4) assaying the analyte solution by using the immunoassay system constituted in 3); and 5) evaluating and selecting the antibody which is useful in assay the soluble CD14 antigen of the above (1) based on the assay result obtained in 4).

(10-2) A screening method of the above (10-1), in which the antibody prepared in the step 1) is the one which specifically binds to a peptide comprising 6 to 20 consecutive amino acid residues selected from the amino acid sequence described in SEQ ID NO: 3 the N terminal of which is positions 1 to 314.

(10-3) A screening method of the above (10-1), in which the antibody prepared in the step 1) is the one produced by using a peptide comprising 8 to 30 consecutive amino acid residues selected from the amino acid sequence described in SEQ ID NO: 3 for the antigen.

(10-4) A screening method of the above (10-2), in which the antibody prepared in the step 1) is the one produced by using a peptide comprising 8 to 30 consecutive amino acid residues selected from the amino acid sequence described in SEQ ID NO: 3 the N terminal of which is positions 1 to 314 for the antigen.

(10-5) A screening method of the above (10-1), in which the analyte solution prepared in the step 2) is a body fluid from a normal donor or a standard sample of human high molecular weight CD14.

(10-6) A screening method of any one of the above (10-1) to (10-5), in which the immunoassay system constituted in the step 3) is the one used in antigen immobilization.

(10-7) A screening method of the above (10-6) which further comprises the step of also preparing a labeled antibody for the antibody prepared in 1); and the antigen immobilization system is constituted in the step 3) by bonding the analyte solution of 2) to an insoluble carrier; and the step 4) is accomplished by reacting the antibody prepared in 1) and the labeled antibody with the antigen immobilization assay system constituted in 3).

(10-8) A screening method of the above (10-6) or (10-7), in which the step 5) of evaluation and selection is accomplished by confirming that the antibody prepared in 1) does not specifically bind to the high molecular weight CD14.

(10-9) A screening method of any one of the above (10-1) to (10-4), further comprising the step of 1)-(2) preparing another antibody which specifically binds to a peptide comprising 6 to 20 consecutive amino acid residues selected from the amino acid sequence described in SEQ ID NO: 3 or an anti-CD14 antibody; and having the following characteristic features:

the analyte solutions prepared in the step 2) are a body fluid from a normal donor and a body fluid from a sepsis patient;

the immunoassay system constituted in the step 3) is a sandwich assay using two antibodies respectively prepared in the step 1) and the step 1)-(2); and the step 5) of the antibody evaluation and selection comprises comparing the assay results for the body fluid from the normal donor and the assay results for the body fluid from the sepsis patient, and the evaluation and selection of an antibody useful in diagnosing sepsis adapted for use in a sandwich immunoassay is conducted on the basis of the difference in the assay results.

(10-10) A screening method of the above (10-9), in which the screening is carried out to find a combination of antibodies for use in the sandwich immunoassay which is useful in assay the soluble CD14 antigen according to the first aspect of the present invention.

(10-11) A screening method of the above (10-9) or (10-10), in which the body fluid from a normal donor and the body fluid from a sepsis patient prepared in the step 2) are blood samples.

(10-12) A screening method of the above (10-9) or (10-10), in which, in constituting the sandwich immunoassay system in the step 3), the antibody prepared in 1) or 1)-(2) is bonded to an insoluble carrier.

(10-13) A screening method of the above (10-9) or (10-10), in which, in constituting the sandwich immunoassay system in the step 3), the antibody prepared in 1) or 1)-(2) is labeled.

(11) A method of any one of the following (11-1) to (11-5) for screening for an antibody which is useful in assay the soluble CD14 antigen of the above (1).

(11-1) A method for screening for an antibody which is useful in assay the soluble CD14 antigen of the above (1), comprising the following steps of:
1) preparing antibodies for screening;
2) preparing the recombinant soluble CD14 fragment of the above (2);
3) reacting the antibodies prepared in 1) with the fragment prepared in 2) to evaluate the specific binding of the antibodies prepared in 1) with the fragment prepared in 2); and
4) selecting the antibody which underwent specific binding with the fragment prepared in 2) in the step 3) as the antibody which is useful in assay the soluble CD14 antigen of the above (1).

(11-2) A screening method of the above (11-1), in which the antibody prepared in the step 1) is an antibody which specifically binds to a protein comprising any one of 6 to 356 consecutive amino acid residues selected from the amino acid sequence described in SEQ ID NO: 3.

(11-3) A screening method of the above (11-1), in which the antibody prepared in the step 1) is an antibody which specifically binds to a protein comprising at least 7 consecutive amino acid residues selected from positions 53 to 68 of the amino acid sequence described in SEQ ID NO: 3.

(11-4) A screening method of any one of the above (11-1) to (11-3), in which the step 3) of evaluating the specific binding of the antibody by the reaction is an antigen immobilization.

(11-5) A screening method of any one of the above (11-1) to (11-3), in which the step 3) of evaluating the specific binding of the antibody by the reaction is accomplished by a sandwich immunoassay.

(11-6) A screening method of any one of the above (11-1) to (11-3), in which the step 3) of evaluating the specific binding of the antibody by the reaction is accomplished by biomolecular interaction analysis.

This invention also provides the following particular method for producing the recombinant soluble CD14 fragment of the above (2).

(12) A method of any one of the following (12-1) to (12-3) for producing the recombinant soluble CD14 fragment of the above (2).

(12-1) A method for producing the recombinant soluble CD14 fragment of the above (2-3) comprising the steps of:
(i) producing a recombinant soluble CD14 fragment having the sequence characterized by the following 1) to 4):
1) a fragment having a partial sequence of the amino acid sequence described in SEQ ID NO: 3, or a fragment having such partial sequence in which 1 to 10 amino acids have been deleted, added, or substituted in the region other than positions 53 to 68 of SEQ ID NO: 3;
2) the N terminal is any one of positions 1 to 17 of SEQ ID NO: 3;
3) the C terminal is any one of positions 134 to 356 in SEQ ID NO: 3;
4) a sequence of a cleavage site for a predetermined protease has been incorporated in the downstream of any one of positions 59 to 70 of SEQ ID NO: 3 by substitution or insertion;
(ii) cleaving the recombinant soluble CD14 fragment prepared in (i) with the predetermined protease; and
(iii) recovering the fragment of the N terminal side cleaved in ii).

(12-2) A method of the above (12-1) for producing the recombinant soluble CD14 fragment of the above (2-3), in which, in the step (i)4), the predetermined protease is PreScission Protease, and the sequence of the cleavage site is Leu, Glu, Val, Leu, Phe, Gln, Gly, Pro.

(12-3) A method of the above (12-1) for producing the recombinant soluble CD14 fragment of the above (2-3), in which, in the step (i)4), the predetermined protease is thrombin, and the sequence of the cleavage site is Leu, Val, Pro, Arg, Gly, Ser.

The novel soluble CD14 antigen of the present invention is useful as a marker for diagnosing a sepsis patient. This soluble CD14 antigen is also useful as a standard substance or competitive substance used in assaying the soluble CD14 antigen.

The recombinant soluble CD14 fragment of the present invention has characteristic features immunologically resembling those of the soluble CD14 antigen, and therefore, it can be used as a standard substance or a competitive substance in assaying the soluble CD14 antigen, and it can also be used in screening for antibodies that can be used in assaying the soluble CD14 antigen.

By "immunological resemblance of the characteristic features with the soluble CD14 antigen", it is meant that the recombinant soluble CD14 fragment of the present invention has the binding ability with the known CD14 antibody and the binding ability with an antibody that binds to the soluble CD14 antigen that are substantially consistent with the soluble CD14 antigen.

Furthermore, the assay kit and the assay method for the soluble CD14 antigen of the present invention are capable of conducting a specific quantitative or qualitative assay at a high sensitivity in a convenient manner, and they are useful in diagnosing sepsis patients.

Furthermore, the screening method of the present invention is useful in searching antibodies that can be used in assaying the soluble CD14 antigen.

Furthermore, the method for producing the recombinant soluble CD14 fragment of the present invention has enabled the production of the recombinant soluble CD14 fragment, expression of which had been impossible in prokaryotic or eukaryotic cells, and in particular, in yeast cells.

DETAILED DESCRIPTION OF THE PREFERRED ASPECTS

Figure 1A:
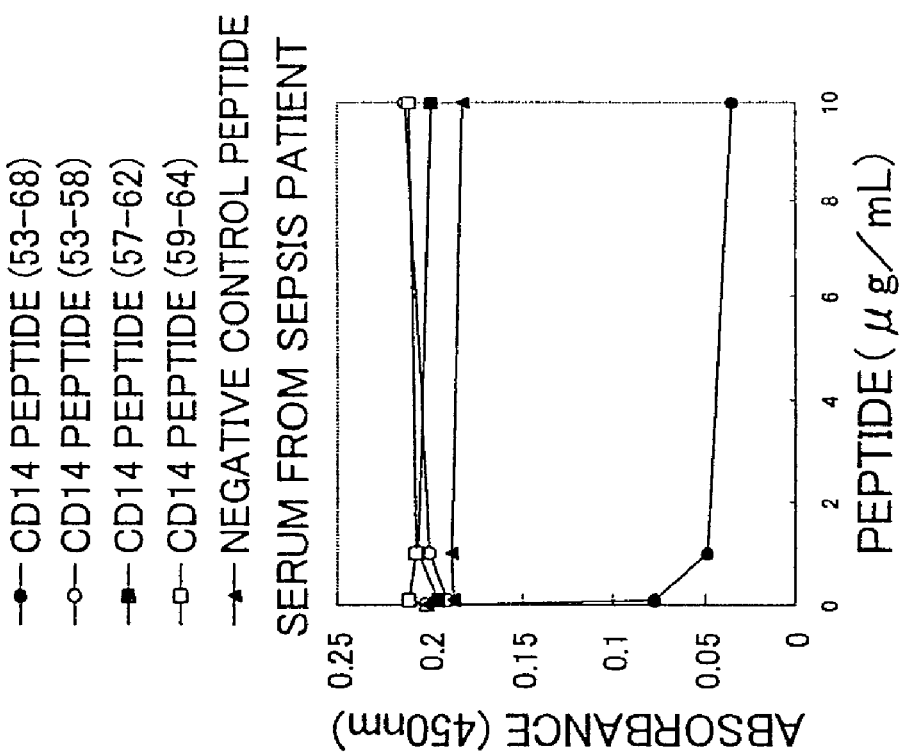
FIG. 1 indicates the result that only S68 peptide prevents binding of the S68 peptide polyclonal antibody and the soluble CD14 antigen of the present invention. (A) shows the state of no binding in the serum from a normal donor, and (B) shows the binding inhibition by the S68 peptide in the serum from a sepsis patient.

Next, the present invention is described in further detail.

Major soluble CD14 proteins that are found in human blood include soluble CD14 proteins with the sizes of about 55 kDa and about 49 kDa reported by Landmann et al. as described in the section of Prior Art. These proteins are respectively the human full length soluble CD14 protein and the human full length soluble CD14 protein from which only 41 amino acids have been deleted from the C terminal. (These proteins are hereinafter sometimes referred to as the "high molecular weight CD14" without denoting "human"). Specific binding of these high molecular weight CD14 with F1025-3-1 antibody is confirmed in WO01/22085.

In addition to such high molecular weight CD14 as mentioned above, also described is a protein which is a low molecular weight CD14 with the molecular weight of 36 kDa.

The inventors of the present invention have found a novel soluble CD14 protein which is different from both the high molecular weight CD14 as described above and the CD14 with the molecular weight of 36 kDa as described in WO01/22085, and this novel soluble CD14 protein exists at a higher content in the blood of a sepsis patient compared to the blood of a normal donor.

The term "soluble CD14 protein" used herein designates a protein found in human plasma (or human serum), which may also be referred to as a "soluble-form CD14 protein". The term "soluble CD14 protein" is used particularly in comparison with the "membrane binding CD14 protein" which is bonded to the cell membrane and which is not present in the human plasma.

"The antibody produced by using a peptide or its fragment or the like for the antigen" or "the antibody produced by using a peptide or its fragment or the like as an antigen" described in the present invention is an antibody that is or that has been produced by immunizing various animals with a peptide or its fragment for the "antigen". The peptide or its fragment used as the "antigen" would then constitute the epitope or a part of the epitope of the antibody, and the antibody would specifically bind to the peptide or its fragment used for the "antigen".

With regard to "the antibody produced (by using . . . ) for the antigen" or "the antibody that has been produced (by using . . . ) for the antigen", an antibody produced by using an immunogen which is a peptide having a carrier or a carrier protein added thereto or a peptide having other amino acid residues added thereto in order to impart the immunogenicity to the peptide used for the "antigen" is also included in the concept of "the antibody produced (by using . . . ) for the antigen" or "the antibody that has been produced (by using . . . ) for the antigen", as long as it has the characteristic features as described above.

An "antibody which undergoes specific binding" means an antibody that immunologically binds to a specific binding target, or an antibody that undergoes a typical antigen—antibody reaction with the specific binding target. For example, occurrence of an antigen—antibody reaction can be confirmed by agglutination assay, sandwich assay, solid phase direct assay, solid phase binding assay, competitive assay, or the like. When the binding between the "antibody which undergoes specific binding" and its specific binding target is represented in terms of affinity, the dissociation constant (KD) would typically be less than $10^{-7}$M. When dissociation constant measurement is unobtainable in a binding test, the result is then indicated as "no substantial binding". When only nonspecific binding is confirmed and the binding ability is smaller than the case of "specific binding" by a factor or 10 or less, 100 or less, and preferably 1,000 or less, the result is also indicated as "no substantial binding".

"No binding with LPS" means that the recombinant soluble CD14 fragment has no or little binding ability with the LPS. The full length CD14 in the living body or the human full length soluble CD14 protein described in SEQ ID NO: 3 has a binding ability with the LPS in the living body or in the serum, and the complex activates the cell. The binding ability of the recombinant soluble CD14 fragment which does "not bind with LPS" is 1/100 or even lower compared to that of the full length CD14 in the living body or the human full length soluble CD14 protein described in SEQ ID NO: 3 with the LPS.

<First Aspect>

First aspect of the present invention is a soluble CD14 antigen which has the following characteristic features 1) to 3):

1) a molecular weight of 13±2 kDa when measured by SDS-PAGE under non-reducing conditions;

2) an amino acid sequence in which the amino acid sequence of SEQ ID NO:1 is present on its N terminal; and 3) ability to specifically bind to an antibody prepared by using the peptide comprising 16 amino acid residues described in SEQ ID NO:2 for the antigen.

The soluble CD14 antigen according to the first aspect of the present invention has the characteristic feature 1) as mentioned above. In SDS-PAGE conducted under non-reducing conditions, a band corresponding to the soluble CD14 antigen according to the first aspect of the present invention is detected at the position corresponding to the molecular weight of 13±2 kDa.

To be more specific, when the molecular weight is calculated by using Precision Plus Protein™ dual color standards (Bio-Rad Laboratories, Inc.) in 12.5% SDS-PAGE under non-reducing conditions, a band is detected at a position corresponding to the molecular weight of 13±2 kDa.

The soluble CD14 antigen according to the first aspect of the present invention has the characteristic feature 2) as mentioned above. The amino acid sequence described in SEQ ID NO: 1 is consistent with the N terminal amino acid sequence of the human CD14 described in SEQ ID NO: 3, and this confirms that the soluble CD14 antigen according to the first aspect of the present invention is one type of the human CD14.

The soluble CD14 antigen according to the first aspect of the present invention has the characteristic feature 3) as mentioned above. The peptide comprising the amino acid residues described in SEQ ID NO:2 described in the characteristic feature 3) corresponds to 16 amino acid residues at positions 53 to 68 of the human CD14 described in SEQ ID NO: 3. Currently, no human protein including the sequence of SEQ ID NO: 2 is known but for the human CD14, and such sequence can be regarded as a sequence specifically included in the human CD14. This also confirms that the soluble CD14 antigen according to the first aspect of the present invention is one type of the human CD14.

Preferably, the soluble CD14 antigen according to the first aspect of the present invention also has the following characteristic feature 4):

4) capable of being obtained from human plasma.

The soluble CD14 antigen according to the first aspect of the present invention characterized by the feature 4) is a protein found in human plasma. The soluble CD14 antigen according to the first aspect of the present invention can be obtained at a high purity by the purification method as described below. In addition, since the soluble CD14 antigen according to the first aspect of the present invention is present at a high concentration in the sepsis patient, it can be used as a marker in diagnosing or detecting the sepsis.

The soluble CD14 antigen according to the first aspect of the present invention can serve as a standard substance or a competitive substance in the kit for assaying the soluble CD14 antigen according to the first aspect of the present invention which is useful in diagnosing or detecting the sepsis.

Next, purification of the soluble CD14 antigen according to the first aspect of the present invention is described.

The soluble CD14 antigen according to the first aspect of the present invention can be purified from human plasma or human serum by combining human CD14-related antibody affinity column chromatography, gel filtration chromatography, and SDS-PAGE. The soluble CD14 antigen according to the first aspect of the present invention fractionated by the column chromatography can be detected at a high efficiency by using the assay kit according to the fifth aspect of the present invention which assays the soluble CD14 antigen according to the first aspect of the present invention.

In this context, the human CD14-related antibody is an anti-human CD14 antibody or an antibody against the peptide derived from the human CD14 amino acid sequence. For example, the soluble CD14 antigen according to the first aspect of the present invention can be separated from the high molecular weight CD14 by an affinity chromatography in which F1025-3-1 antibody or F1024-1-3 antibody is used for the anti-human CD14 antibody. The high molecular weight CD14 will then be adsorbed by the antibody, and the soluble CD14 antigen according to the first aspect of the present invention will be eluted as the initial fraction. The soluble CD14 antigen can then be separated from other proteins of the serum by an affinity chromatography using an antibody which specifically binds to the peptide comprising the amino acid residues described in SEQ ID NO: 2.

The soluble CD14 antigen according to the first aspect of the present invention is adsorbed to the antibody, and the adsorbed soluble CD14 antigen will elute from the column when medium is acidified. The hybridomas producing the antibody F1025-3-1 and the antibody F1024-1-3 have been internationally deposited to the National Institute of Advanced Industrial Science and Technology (Independent Administrative Institute), International Patent Organism Depositary (IPOD) (Chuo-dairoku, 1-1, Higashi 1-chome, Tsukuba-shi, Ibaraki-ken, Japan) with the Accession No. FERM BP-7296 and the Accession No. FERM BP-7511 as described in WO01/22085 and WO01/72993, respectively.

The soluble CD14 antigen in the serum can be separated from other proteins by an affinity chromatography using an anti-human CD14 polyclonal antibody. Then, the soluble CD14 antigen can be separated from the high molecular weight CD14 by an affinity chromatography using the anti-human CD14 monoclonal antibody.

The soluble CD14 antigen according to the first aspect of the present invention can also be further purified by subjecting the human serum or the fraction partially purified by the affinity chromatography as described above to gel filtration chromatography. In this case, the assay kit according to the fifth aspect of the present invention may be used as described above to collect the fraction from which the soluble CD14 antigen according to the first aspect of the present invention is detected. A fraction corresponding to the molecular weight of 35±10 kDa can also be collected by using a molecular weight marker.

The fraction partially purified as described above may also be subjected to SDS-PAGE under non-reducing conditions to collect the part corresponding to 13±2 kDa for further purification. The thus collected fraction contains the soluble CD14 antigen according to the first aspect of the present invention purified to a high degree as its main protein.

An even higher purity can be realized by further conducing the purification by anion exchange column chromatography, reversed phase chromatography, isoelectric focusing, or the like. For example, in an anion exchange column chromatography at pH 8.5, the soluble CD14 antigen according to the first aspect of the present invention elutes at an ionic strength of about 0.3M.

<Second Aspect>

Second aspect of the present invention is a recombinant soluble CD14 fragment which has the following characteristic features 1) to 3):

1) a molecular weight of 13±2 kDa when measured by SDS-PAGE under non-reducing conditions;

2) no ability to specifically bind to 3C10 or MEM-18; and 3) ability to specifically bind to an antibody prepared by using the peptide comprising 16 amino acid residues described in SEQ ID NO:2 for the antigen.

Examples of the recombinant soluble CD14 fragment according to the second aspect of the present invention include the recombinant soluble CD14 fragments having the sequences characterized by the following 5) to 7):

5) a fragment having a partial sequence of the amino acid sequence described in SEQ ID NO: 3, or a fragment having such partial sequence in which 1 to 10 amino acids have been deleted, added, or substituted in the region other than positions 53 to 68 of SEQ ID NO: 3;

6) the N terminal is any one of positions 1 to 17 of SEQ ID NO: 3; and 7) the C terminal is any one of positions 59 to 90 in SEQ ID NO: 3.

Of these exemplary recombinant soluble CD14 fragments, the preferred is the one in which, in 6), the N terminal is any one of positions 1 to 6 of SEQ ID NO: 3, and the more preferred is the one in which the N terminal is position 1 of SEQ ID NO: 3.

Also preferred is the recombinant soluble CD14 fragments wherein, in 7), the C terminal is any one of positions 59 to 80 of SEQ ID NO: 3, and the more preferred is the one in which the C terminal is any one of positions 64 to 75 of SEQ ID NO: 3, and even more preferred is the one in which the C terminal is position 64 of SEQ ID NO: 3.

Particularly preferred is the recombinant soluble CD14 fragment of any one of the above (2-3) to (2-5) in which, in 6), the N terminal is position 1 of SEQ ID NO: 3, and the C terminal is position 64 of SEQ ID NO: 3.

Also particularly preferred is the recombinant soluble CD14 fragment in which the fragment of 5) is a fragment having a partial sequence of the amino acid sequence described in SEQ ID NO: 3.

Next, the method for producing the recombinant soluble CD14 fragment according to the second aspect of the present invention by genetic engineering means is described. The method, however, is not particularly limited, and any method commonly used in the art can be employed.

The nucleotide sequence of the DNA coding for the amino acid sequence of the fragment of the present invention is not limited to one sequence since, as is known in the art, the gene coding for an amino acid may comprise 1 to 6 different types of DNA triplets (codons) depending on the type of the amino acid. Therefore, the nucleotide sequence of the gene is not limited as long as the gene comprises the nucleotide sequence coding for the fragment of the present invention. The gene may also comprise a cDNA, a chromosomal DNA, a combination thereof, or a cDNA containing an intron which can be adequately spliced. The gene, however, is preferably a cDNA in view of the handling convenience in the genetic engineering processes.

The gene is not limited for its production process. For example, the gene may be the one produced by chemical synthesis, the one obtained from an adequate DNA library, or the one produced by PCR (Polymerase Chain Reaction) using a DNA comprising the DNA of the gene coding for the full length or a part of the CD14 for the template. The gene may also be the one produced by annealing or ligating the gene or its fragment produced by such means.

The DNA of the gene can be chemically synthesized as described below by dividing the DNA of the gene to fragments of about 20 to 30 nucleotides and synthesizing these fragments by a DNA synthesizer (for example, model 394 manufactured by Applied Biosystems), phosphorylating the 5' terminal of the fragments if desired and annealing the fragments, and ligating the annealed fragments to thereby obtain the target DNA.

The gene can also be obtained by a PCR process using a genomic library or a cDNA library for the template. When a PCR process is employed, a sense primer and an antisense primer designed on the basis of a known nucleotide sequence and the nucleotide sequence of the DNA or the like coding for the fragment of the present invention or a fragment having a protease cleavage site inserted or substituted (hereinafter sometimes referred to as the "fragment of the present invention or the like"), and if desired, a restriction enzyme-recognizing sequence are prepared, and the PCR is conducted for any particular DNA library according to the method known in the art (see Michael A I. et al. ed., Polymerase Chain Reaction, PCR Protocols, A Guide to Methods and Applications, 1990, Academic Press). The DNA library used is not particularly limited as long as it contains the DNA of the gene or a part thereof. Therefore, the DNA library used may be a commercially available DNA library, or the one prepared by producing cDNA in accordance with the method of Sambrook, J. et al. from lymphocytes from human peripheral blood or the like, human cell line, or hybridoma optionally after activating with an adequate activating agent. The nucleotide sequence of the DNA coding for the amino acid sequence of the fragment of the present invention or the like is not limited to one sequence since, as is known in the art, 1 to 6 triplets (codons) of the DNA of the gene may be present per one amino acid depending on the type of the amino acid. Therefore, the gene may comprise any nucleotide sequence as long as the gene comprises the nucleotide sequence coding for the fragment of the present invention or the like.

The recombinant vector may be a vector of any form including circular, linear, single stranded, double stranded, and a combination thereof, and the vector used may be adequately selected according to the intended use. In view of the handling convenience and ease of incorporation in the host, the vector is preferably a circular vector, and in view of the stability, the vector is preferably double stranded.

The "recombinant soluble CD14 fragment" is a soluble fragment produced by genetic manipulation which has a partial amino acid sequence of the human full length CD14 protein described in SEQ ID NO: 3.

The recombinant soluble CD14 fragment according to the second aspect of the present invention has the characteristic feature 1) as described above. That is, a band corresponding to the recombinant soluble CD14 fragment according to the second aspect of the present invention is detected in SDS-PAGE carried out under non-reducing conditions at the position corresponding to a molecular weight of 13±2 kDa.

More specifically, when the molecular weight is determined by using Precision Plus Protein™ dual color standards (Bio-Rad Laboratories, Inc.) in 12.5% SDS-PAGE carried out under non-reducing conditions, a band is detected at the position of the molecular weight of 13±2 kDa.

The recombinant soluble CD14 fragment according to the second aspect of the present invention has the characteristic feature 2) as described above. That is, it has no ability to specifically bind to 3C10 or MEM-18.

By "no ability to specifically bind to 3C10 or MEM-18", is meant that the recombinant soluble CD14 fragment does not undergo immunological binding, or ordinary antigen—antibody reaction. The recombinant soluble CD14 fragment according to the second aspect of the present invention which has "no ability to specifically bind to 3C10 or MEM-18" shows a binding ability to the 3C10 and MEM-18 which is 1/100 or less, and preferably 1/1,000 or less compared to that of the full length CD14 found in the living body or the human full length recombinant soluble CD14 protein described in SEQ ID NO: 3.

The recombinant soluble CD14 fragment according to the second aspect of the present invention has the characteristic feature 3) as described above, and in particular, it specifically binds to a polyclonal antibody. The peptide comprising the amino acid residues described in SEQ ID NO: 2 described in the characteristic feature 3) corresponds to 16 amino acid residues at positions 53 to 68 of the human CD14 described in SEQ ID NO: 3. Since the polyclonal antibody recognizes a sequence having a length of at least 7 amino acids (see Example 4 as will be describe later), the recombinant soluble CD14 fragment according to the second aspect at least includes a sequence of 7 consecutive amino acids selected from positions 53 to 68 of the human CD14 described in SEQ ID NO: 3.

3C10 and MEM-18 are well known anti-CD14 antibodies. The epitope on the CD14 is conceived to be positions 7 to 14 and positions 57 to 64, respectively, and the recombinant soluble CD14 fragment derived from the conventional human CD14 will bind to 3C10 and MEM-18 as long as the epitope region is included in the sequence.

The recombinant soluble CD14 fragment according to the second aspect of the present invention has the characteristic features 1) to 3) as described above, and accordingly, it has physical properties and immunological nature similar to those of the soluble CD14 antigen according to the first aspect of the present invention. In particular, it is estimated from the similarity in the immunological nature that the recombinant soluble CD14 fragment according to the second aspect of the present invention has a conformation of the amino acid residue sequence which may serve as the epitope similar to that of the soluble CD14 antigen according to the first aspect of the present invention. Therefore, the recombinant soluble CD14 fragment according to the second aspect of the present invention is particularly useful as a standard substance in assaying the soluble CD14 antigen according to the first aspect of the present invention. While a recombinant polypeptide having the amino acids of positions 1 to 307 at N terminal of human CD14 in which the serine at position 286 has been replaced with cysteine (hereinafter referred to as the "rsCD14(1-307) S286C") has generally been used as the standard substance in assaying the soluble CD14 antigen according to the first aspect of the present invention, use of the recombinant soluble CD14 fragment according to the second aspect of the present invention is handy in converting the immunological reaction to the amount of substance owing to the similar molecular weight. In addition, the recombinant soluble CD14 fragment according to the second aspect of the present invention exhibits reactivity similar to that of the soluble CD14 antigen according to the first aspect of the present invention in different solvent conditions. For example, while the soluble CD14 antigen according to the first aspect of the present invention and rsCD14(1-307)S286C show different immunological reactivity for the specimen from citrated blood and EDTA blood, the immunological reactivity is consistent between the soluble CD14 antigen according to the first aspect of the present invention and the recombinant soluble CD14 fragment according to the second aspect of the present invention. Similarly, the recombinant soluble CD14 fragment according to the second aspect of the present invention is also useful as an analog in assaying the soluble CD14 antigen according to the first aspect of the present invention by a competitive method.

Furthermore, since the recombinant soluble CD14 fragment according to the second aspect of the present invention has immunological nature similar to that of the soluble CD14 antigen according to the first aspect of the present invention, it can be used as a specific binding target in screening for an antibody that can be used in assaying the soluble CD14 antigen according to the first aspect of the present invention. Such an assay can be accomplished, of course, by using the soluble CD14 antigen according to the first aspect of the present invention for the specific binding target. The soluble CD14 antigen, however, is present in the living body only in a minute amount, and therefore, the recombinant soluble CD14 fragment according to the second aspect of the present invention would serve as a particularly useful substitute.

As described above, the recombinant soluble CD14 fragment according to the second aspect of the present invention is useful for various applications, and this usefulness can be ascribed to the characteristic features 1) to 3). In other words, the recombinant soluble CD14 fragment according to the second aspect of the present invention having the characteristic features 1) to 3) is not represented by its sequence but by the function including the physical properties and the immunological nature of the CD14 fragment.

The recombinant soluble CD14 fragment according to the second aspect of the present invention has further characteristic feature that it does not bind to LPS. Although no specific indication of the peptide is included in WO96/20956, it discloses a peptide which contains 8 to 60 amino acids including positions 57 to 64 of the human CD14 and which binds to LPS. This peptide and the recombinant soluble CD14 fragment according to the second aspect of the present invention are not identical, as clearly understood by the fact that the recombinant soluble CD14 fragment according to the second aspect of the present invention has the characteristic feature 4) as described above.

Examples of the recombinant soluble CD14 fragment according to the second aspect of the present invention include the recombinant soluble CD14 fragments having the sequences characterized by the following 5) to 7):

5) a fragment having a partial sequence of the amino acid sequence described in SEQ ID NO: 3, or a fragment having such partial sequence in which 1 to 10 amino acids have been deleted, added, or substituted in the region other than positions 53 to 68 of SEQ ID NO: 3;

6) the N terminal is any one of positions 1 to 17 of SEQ ID NO: 3; and 7) the C terminal is any one of positions 59 to 90 in SEQ ID NO: 3.

Of these exemplary recombinant soluble CD14 fragments, the preferred is the one in which, in 6), the N terminal is any one of positions 1 to 6 of SEQ ID NO: 3, and the more preferred is the one in which the N terminal is position 1 of SEQ ID NO: 3.

Also preferred is the recombinant soluble CD14 fragments wherein, in 7), the C terminal is any one of positions 59 to 80 of SEQ ID NO: 3, and the more preferred is the one in which the C terminal is any one of positions 64 to 75 of SEQ ID NO: 3, and even more preferred is the one in which the C terminal is position 64 of SEQ ID NO: 3.

Particularly preferred is the recombinant soluble CD14 fragment of any one of the above (2-3) to (2-5) in which, in 6), the N terminal is position 1 of SEQ ID NO: 3, and the C terminal is position 64 of SEQ ID NO: 3.

Also particularly preferred is the recombinant soluble CD14 fragment in which the fragment of 5) is a fragment having a partial sequence of the amino acid sequence described in SEQ ID NO: 3.

Next, the method for producing the fragment of the present invention by genetic engineering means is described. The method, however, is not particularly limited, and any method commonly used in the art can be employed.

The nucleotide sequence of the DNA coding for the amino acid sequence of the fragment of the present invention is not limited to one sequence since, as is known in the art, 1 to 6 triplets (codons) of the DNA of the gene may be present for one amino acid depending on the type of the amino acid. Therefore, the gene may comprise any nucleotide sequence as long as the gene comprises the nucleotide sequence coding for the fragment of the present invention. The gene may also comprise a cDNA, a chromosomal DNA, a combination thereof, or a cDNA containing an intron which can be adequately spliced. The gene, however, is preferably a cDNA in view of the handling convenience in the genetic engineering processes.

The gene is not limited for its production process. For example, the gene may be the one produced by chemical synthesis, the one obtained from an adequate DNA library, or the one produced by PCR (Polymerase Chain Reaction) using a DNA comprising the DNA of the gene coding for full length of a part of the CD14 for the template. The gene may also be the one produced by annealing or ligating the gene or its fragment produced by such means.

The DNA of the gene can be chemically synthesized as described below by dividing the DNA of the gene to fragments of 20 to 30 nucleotides and synthesizing these fragments in a DNA synthesizer (for example, model 394 manufactured by Applied Biosystems), phosphorylating the 5' terminal of the fragments if desired and annealing the fragments, and ligating the annealed fragments to thereby obtain the target DNA.

The gene can also be obtained by a PCR process using a genomic library or a cDNA library for the template. When a PCR process is employed, a sense primer and an antisense primer designed on the basis of a known nucleotide sequence and the nucleotide sequence of the DNA or the like coding for the fragment of the present invention or a fragment having a protease cleavage site inserted or substituted (hereinafter sometimes referred to as the "fragment of the present invention or the like"), and if desired, a restriction enzyme-recognizing sequence are prepared, and the PCR is conducted for any particular DNA library according to the method known in the art (see Michael A I. et al. ed., Polymerase Chain Reaction, PCR Protocols, A Guide to Methods and Applications, 1990, Academic Press). The DNA library used is not particularly limited as long as it contains the DNA of the gene or a part thereof. Therefore, the DNA library used may be a commercially available DNA library, or the one prepared by producing cDNA in accordance with the method of Sambrook, J. et al. from lymphocytes from human peripheral blood or the like, human cell line, or hybridoma optionally after activating with an adequate activating agent. The nucleotide sequence of the DNA coding for the amino acid sequence of the fragment of the present invention or the like is not limited to one sequence since, as is known in the art, 1 to 6 triplets (codons) of the DNA of the gene may be present per one amino acid depending on the type of the amino acid. Therefore, the gene may comprise any nucleotide sequence as long as the gene comprises the nucleotide sequence coding for the fragment of the present invention or the like.

The recombinant vector may be a vector of any form including circular, linear, single stranded, double stranded, or a combination thereof, and the vector used may be adequately selected according to the intended use. In view of the handling convenience and ease of incorporation in the host, the vector is preferably a circular vector, and in view of the stability, the vector is preferably double stranded.

The signal sequence connected can be adequately selected, and the preferred is the signal sequence coding for the signal peptide having the sequence: Met Glu Arg Ala Ser Cys Leu Leu Leu Leu Leu Leu Pro Leu Val His Val Ser Ala (SEQ ID NO: 28) of the human CD14 (Goyer et al., Nucleic Acid Research, vol. 16, page 4173, 1988).

When the fragment is to be expressed as an inclusion body by using *E. coli* for the host, addition of methionine or a peptide containing methionine at the N terminal is preferred.

In view of the host, the preferable recombinant vector is the one which transforms an animal cell, yeast, or other eukaryotic cell so that the fragment of the present invention or the like is expressed by the transformed cell. Accordingly, a preferable recombinant vector contains at least a translation initiation codon, a termination codon, and a selective marker gene, as well as a polyadenylation sequence; SV40 promoter, EF1α promoter, or SRα promoter which functions in an animal cell, or AOX1 promoter which functions in yeast; SV40 replication origin; and the like.

The recombinant vector can be obtained by ligating the gene DNA with other DNA fragment comprising any desired nucleotide sequence, or by introducing the gene DNA in any suitable vector (see Sambrook J. et al., Molecular Cloning, a Laboratory Manual 2nd ed., Cold Spring Harbor Laboratory, New York, 1989).

The transformant can be obtained by introducing the recombinant vector in the host cell or organism.

The transformant is preferably the one which is capable of expressing the fragment of the present invention or the like, and most preferably, the one which is capable of expressing the fragment of the present invention or the like in a culture supernatant. Use of such transformant will facilitate production of the fragment of the present invention or the like in a large amount.

The transformant is cultivated, and gene amplification and induction of the gene expression are conducted as desired. The cultured mixture is then collected for purification of the fragment of the present invention or the like by an adequate combination of concentration, solubilization, dialysis, various chromatographic processes, and other processes.

The "cultured mixture" means a transformant, a culture medium containing the transformant, a culture supernatant, or a cell lysate.

The transformant produced by such production process is not particularly limited as long as it expresses the fragment of the present invention or the like. However, the transformant is preferably the one produced by using a cell selected from mammalian cells such as COS cell and CHO cell, yeast, and *E. coli*.

Next, embodiments of the cultivation and the induction of the expression are described, and in these embodiments, *E. coli*, a mammalian cell such as CHO cell, or a yeast of genus *Pichia* was used for the transformant.

When the transformant used is *E. coli* that has been transformed by a recombinant DNA molecule containing trp promoter, the transformant is preliminarily cultivated in L-Broth, and then inoculated in M9-CA culture medium at an amount of 1/50 for cultivation at 37° C. Several hours after the start of the cultivation, OD 550 value reaches 1 to 4 (i.e. logarithmic growth phase), and 3β-indoleacrylic acid is then added to a final concentration of 10 μg/ml to thereby induce the expression. Cultivation is continued for another about 1 to 2 days to obtain the cultured mixture containing the target protein.

When the transformant used is a *Pichia* yeast that has been transformed by a recombinant vector containing AOX1 promoter, the transformant is preliminarily cultivated in BMGY medium for about 2 days, and after changing the culture medium, methanol is added to induce the expression. The cultivation is continued at 30° C. for another about 1 to 2 days to obtain the cultured mixture containing the target protein.

When the transformant used is a mammalian cell such as CHO cell that has been transformed by a recombinant vector containing EF1α promoter, the transformant is cultivated in DMEM medium supplemented with 10% fetal bovine serum. The cells are inoculated at a concentration of about 1 to $10 \times 10^4$ cells/ml, and cultivated under the conditions of 37° C.

and 5% carbon dioxide gas/95% air. Usually, the culture reaches confluence at 2 to 3 days, and then, the culture medium is replaced with serum free D-MEM. The cultivation is continued for another 2 to 3 days to thereby obtain the cultured mixture containing the target protein. When the amount of the target protein produced is insufficient, the production can be enhanced by adding methotrexate as described above for gene amplification to thereby increase the amount of the product.

The fragment of the present invention or the like may be purified from the thus obtained cultured mixture by a method adequately selected from the methods commonly used in purifying a fragment, a protein, or a polypeptide. More specifically, an adequate method may be selected and combined from the methods commonly used in the art such as salting out, ultrafiltration, isoelectric precipitation, gel filtration, electrophoresis, ion exchange chromatography, hydrophobic chromatography, antibody chromatography and other affinity chromatography processes, chromatofocusing, adsorption chromatography, and reversed phase chromatography, and if desired, the product can be further purified by using HPLC system or the like.

In the production process, the fragment of the present invention or the like may also be expressed as a fusion protein with β-galactosidase of E. coli or other polypeptide. In such a case, a further step of cleaving such protein would be required at some point of the purification by treating the fusion protein with a chemical reagent such as cyanogen bromide or hydroxylamine, or an enzyme such as protease.

When the transformant used is E. coli, and the fragment of the present invention or the like is produced as an inclusion body which is an insolubilized protein, a further step of solubilizing the inclusion body followed by denaturing and refolding will be required at some point of the purification (Thomas, E. et al., J. Molecular Biology, 87, 563-577, 1974).

More specifically, the cell is lysed and centrifuged to collect the pellet. Next, a solubilization buffer containing urea or guanidine hydrochloride, surfactant, oxidized glutathione, and reduced glutathione at an adequate content (for example, a buffer containing 5M guanidine hydrochloride, 0.005% Tween 80, 50 mM Tris-HCl (pH 8.0), 5 mM EDTA, 2 mM reduced glutathione, and 0.02 mM oxidized glutathione) is added to the pellet, and 2-mercaptoethanol is then added for denaturing. The mixture is then dialyzed against a solution which is the same as the buffer used for the solubilization except for the absence of the guanidine hydrochloride to thereby promote the refolding. When the fragment has been expressed as a fusion protein, the region of the unnecessary protein is cleaved after the procedure as described above by using a chemical reagent such as cyanogen bromide or an enzyme such as protease, and the product is further purified by an adequate chromatographic process.

Alternatively, the fragment of the present invention can be chemically synthesized by a method commonly used in the art, and the fragment produced by such chemical synthesis is also within the scope of the fragment of the present invention. For example, the fragment may be produced by synthesis on a commercially available peptide synthesizer, or by synthesizing the fragments of the fragment of the present invention, and ligating the thus synthesized fragments.

<Third Aspect>

Third aspect of the present invention is a recombinant soluble CD14 fragment produced by the following steps i) to iii):

i) the step of producing a fragment having a partial sequence of the amino acid sequence described in SEQ ID NO: 3, or a fragment having such partial sequence in which 1 to 10 amino acids have been deleted, added, or substituted in the region other than positions 53 to 68 of SEQ ID NO: 3, in which a cleavage site for a predetermined protease has been substituted or inserted;

ii) the step of cleaving the recombinant soluble CD14 fragment produced in i) with the predetermined protease; and iii) the step of recovering the fragment of the N terminal side cleaved in ii); and having the following characteristic features 1) to 3):

1) a molecular weight of 13±2 kDa when measured by SDS-PAGE under non-reducing conditions;

2) no ability to specifically bind to 3C10 or MEM-18; and 3) ability to specifically bind to an antibody prepared by using the peptide comprising 16 amino acid residues described in SEQ ID NO:2 for the antigen.

The inventors of the present invention postulated the mechanism that has resulted in the presence in blood of the soluble CD14 antigen according to the first aspect of the present invention as described below, and attempted to produce the recombinant soluble CD14 fragment according to the third aspect of the present invention by a process similar to the postulated in vivo production mechanism, which by no means limit or define the scope of the present invention.

As will be explained below, the soluble CD14 antigen according to the first aspect of the present invention exhibits specific increase in the blood when the donor suffers from sepsis. More specifically, it increases by an in vivo phenomenon which may occur in the early stage of the sepsis, and in particular, immediately after the exposure of the living body to endotoxin or the like.

One in vivo phenomenon which may occur immediately after the exposure of the living body to endotoxin or the like is activation of neutrophil, and the activated neutrophil releases a protease such as neutrophil elastase. It is estimated that, in the course of this process, high molecular weight CD14 such as soluble full length CD14 or membrane CD14 (hereinafter referred to as the "full length CD14") in the living body is decomposed by the elastase, and this results in the increase of the soluble CD14 antigen according to the first aspect of the present invention. Although various fragments are likely to be produced by this cleavage due to the low specificity of the cleavage by the elastase, it can be expected that it is the soluble CD14 antigen according to the first aspect of the present invention that is finally produced. Also expected are interactions with other proteases, and such interactions should also lead to the production of the soluble CD14 antigen according to the first aspect of the present invention.

The soluble CD14 antigen according to the first aspect of the present invention produced by the decomposition of the full length CD14 by the protease such as elastase is at least stable to the degree that it is detectable in the living body (i.e. in the serum).

Since the soluble CD14 antigen according to the first aspect of the present invention can be immunologically assayed separately from the full length CD14 as will be described below, the soluble CD14 antigen according to the first aspect of the present invention formed by the phenomenon as described above is expected to have a conformation different from that of the full length CD14.

Since the recombinant soluble CD14 fragment according to the third aspect of the present invention is a recombinant soluble CD14 fragment of the soluble CD14 antigen according to the first aspect of the present invention, production of the fragment having a conformation similar to the soluble CD14 antigen according to the first aspect of the present invention, namely, the fragment having immunological specificity similar to the soluble CD14 antigen according to the first aspect of the present invention was attempted by cleaving off the C terminal region from a relatively large CD14 fragment by means of a protease. The inventors thereby succeeded in producing, isolating, and purifying the recombinant soluble CD14 fragment according to the third aspect of the present invention.

Next, an embodiment of producing the recombinant soluble CD14 fragment according to the third aspect of the present invention is described.

In step i), a recombinant soluble CD14 fragment having the sequence characterized by the following 8) to 11) is produced.

8) a fragment having a partial sequence of the amino acid sequence described in SEQ ID NO: 3, or a fragment having such partial sequence in which 1 to 10 amino acids have been deleted, added, or substituted in the region other than positions 53 to 68 of SEQ ID NO: 3;

9) the N terminal is any one of positions 1 to 17 of SEQ ID NO: 3;

10) the C terminal is any one of positions 134 to 356 in SEQ ID NO: 3;

11) a sequence of a cleavage site for a predetermined protease has been incorporated in the downstream of any one of positions 59 to 90 of SEQ ID NO: 3 by substitution or insertion.

Exemplary predetermined proteases in the step (i)11) include PreScission Protease, thrombin, and Factor Xa. When the predetermined protease is PreScission Protease, the sequence of the cleavage site is Leu, Glu, Val, Leu, Phe, Gln, Gly, Pro, and these 8 amino acid residues may be incorporated, for example, in the downstream of any one of positions 59 to 70 of SEQ ID NO: 3 by substitution or insertion. When the predetermined protease is thrombin, the sequence of the cleavage site is Leu, Val, Pro, Arg, Gly, Ser, and these 6 amino acid residues may be incorporated, for example, in the downstream of any one of positions 59 to 70 of SEQ ID NO: 3. When the predetermined protease is Factor Xa, the sequence of the cleavage site is Ile, Glu, Gly, Arg, and these 4 amino acid residues may be incorporated, for example, in the downstream of any one of positions 59 to 70 of SEQ ID NO: 3.

Of these recombinant soluble CD14 fragments, the preferred is the one which has been produced by preparing in step (i) a fragment wherein, in 9), the N terminal is any one of positions 1 to 6 of SEQ ID NO: 3, and the more preferred is the one which has been produced by preparing a fragment in which the N terminal is position 1 of SEQ ID NO: 3.

Also preferred is the recombinant soluble CD14 fragment which has been produced by preparing in step (i) a fragment wherein, in 11), the sequence of the cleavage site for the predetermined protease has been incorporated in the downstream of any one of positions 59 to 68 of SEQ ID NO: 3 by substitution or insertion.

Also preferred is the recombinant soluble CD14 fragment which has been produced by preparing a fragment wherein the sequence of the cleavage site for the predetermined protease has been incorporated in the downstream of position 64 of SEQ ID NO: 3 by substitution or insertion.

Particularly preferred is the recombinant soluble CD14 fragment which has been produced by preparing a fragment wherein the N terminal is any one of positions 1 to 6 of SEQ ID NO: 3, and the sequence of the cleavage site for the predetermined protease has been incorporated in the downstream of position 64 of SEQ ID NO: 3 by substitution or insertion.

With regard to step (i), once the sequence is determined, the recombinant soluble CD14 fragment can be prepared as described in the section of the recombinant soluble CD14 fragment according to the second aspect of the present invention.

With regard to the step (ii), the step of cleaving the fragment wherein cleavage site of the predetermined protease has been incorporated by insertion or substitution with the predetermined protease may be accomplished by the reaction commonly used in the art under the optimal conditions of the predetermined protease. For example, when the predetermined protease is PreScission Protease, the cleavage reaction may be allowed to take place overnight at 4° C. with the ratio of the enzyme to the substrate kept in the range of 0.001 to 10:1 (U:μg). When the predetermined protease is thrombin, cleavage reaction by the thrombin may be allowed to take place overnight at 22° C. with the ratio of the enzyme to the substrate kept in the range of 0.001 to 10:1 (U:μg). When the predetermined protease is Factor Xa, the cleavage reaction may be allowed to take place overnight by adding the ingredients so that the ratio of the enzyme to the substrate is in the range of 0.0008 to 8:1 (U:μg).

With regard to the step (iii) of recovering the fragment of the N terminal side, this step can be accomplished as described above for the purification of the fragment of the present invention or the like.

The production process as described above is capable of producing the fragment of the present invention or the like at a high yield with high product consistency and at a commercial scale.

The particular sequence of the recombinant soluble CD14 fragment according to the third aspect of the present invention can be deduced from the production process as described above. The preferable fragment has a sequence which is the same as the fragment described in the section of the second aspect of the present invention. In some cases, the recombinant soluble CD14 fragment according to the third aspect of the present invention has a part of the cleavage site sequence of the predetermined protease added to its C terminal.

The recombinant soluble CD14 fragment according to the third aspect of the present invention is particularly preferable since it reacts to the kit which only detects the soluble CD14 antigen according to the first aspect of the present invention and which does not detect the high molecular weight CD14 in blood; it has been confirmed to show a reactivity equivalent to that of the soluble CD14 antigen according to the first aspect of the present invention in the detection by western blotting (see Example 14-(2) below); and its conformation can be assumed to be substantially equivalent to that of the soluble CD14 antigen according to the first aspect of the present invention.

In the following, the recombinant soluble CD14 fragment according to the second aspect of the present invention and the recombinant soluble CD14 fragment according to the third aspect of the present invention are described together (Both are sometimes described as "the recombinant soluble CD14 fragment according to the second aspect of the present invention" or "the recombinant soluble CD14 fragment of the present invention").

The "recombinant soluble CD14 fragment" is a soluble fragment produced by genetic manipulation which has a partial amino acid sequence of the human full length CD14 protein described in SEQ ID NO: 3.

The recombinant soluble CD14 fragment according to the second aspect of the present invention has the characteristic feature 1) as described above. That is, a band corresponding to the recombinant soluble CD14 fragment according to the second aspect of the present invention is detected in SDS- PAGE carried out under non-reducing conditions at the position corresponding to a molecular weight of 13±2 kDa.

More specifically, when the molecular weight is determined by using Precision Plus Protein™ dual color standards (Bio-Rad Laboratories, Inc.) in 12.5% SDS-PAGE carried out under non-reducing conditions, a band is detected at the position of the molecular weight of 13±2 kDa.

The recombinant soluble CD14 fragment according to the second aspect of the present invention has the characteristic feature 2) as described above. That is, it has no ability to specifically bind to 3C10 or MEM-18.

By "no ability to specifically bind to 3C10 or MEM-18", is meant that the recombinant soluble CD14 fragment does not undergo immunological binding, or ordinary antigen—antibody reaction to 3C10 or MEM-18. The recombinant soluble CD14 fragment according to the second aspect of the present invention which has "no ability to specifically bind to 3C10 or MEM-18" shows a binding ability to the 3C10 and MEM-18 which is 1/100 or less, and preferably 1/1,000 or less compared to that of the full length CD14 found in the living body or the human full length recombinant soluble CD14 protein described in SEQ ID NO: 3.

The recombinant soluble CD14 fragment according to the second aspect of the present invention has the characteristic feature 3) as described above, and in particular, it specifically binds to a polyclonal antibody. The peptide comprising the amino acid residues described in SEQ ID NO: 2 described in the characteristic feature 3) corresponds to 16 amino acid residues at positions 53 to 68 of the human CD14 described in SEQ ID NO: 3. Since the polyclonal antibody recognizes a sequence having a length of at least 7 amino acids (see Example 4 as will be describe later), the recombinant soluble CD14 fragment according to the second aspect at least includes a sequence of 7 consecutive amino acids selected from positions 53 to 68 of the human CD14 described in SEQ ID NO: 3.

3C10 and MEM-18 are well known anti-CD14 antibodies. The epitope on the CD14 is conceived to be positions 7 to 14 and positions 57 to 64, respectively, and the recombinant soluble CD14 fragment derived from the conventional human CD14 will bind to 3C10 and MEM-18 as long as the epitope region is included in the sequence.

The recombinant soluble CD14 fragment according to the second aspect of the present invention has the characteristic features 1) to 3) as described above, and accordingly, it has physical properties and immunological nature similar to those of the soluble CD14 antigen according to the first aspect of the present invention. In particular, it is estimated from the similarity in the immunological nature that the recombinant soluble CD14 fragment according to the second aspect of the present invention has a conformation of the amino acid residue sequence which may serve as the epitope similar to that of the soluble CD14 antigen according to the first aspect of the present invention. Therefore, the recombinant soluble CD14 fragment according to the second aspect of the present invention is particularly useful as a standard substance in assaying the soluble CD14 antigen according to the first aspect of the present invention. While a recombinant polypeptide having the amino acids of positions 1 to 307 at N terminal of human CD14 in which the serine at position 286 has been replaced with cysteine (hereinafter referred to as the "rsCD14(1-307)S286C") has generally been used as the standard substance in assaying the soluble CD14 antigen according to the first aspect of the present invention, use of the recombinant soluble CD14 fragment according to the second aspect of the present invention is handy in converting the immunological reaction to the amount of substance owing to the similar molecular weight. In addition, the recombinant soluble CD14 fragment according to the second aspect of the present invention exhibits reactivity similar to that of the soluble CD14 antigen according to the first aspect of the present invention in different solvent conditions. For example, while the soluble CD14 antigen according to the first aspect of the present invention and rsCD14(1-307)S286C show different immunological reactivity for the specimen from citrated blood and EDTA blood, the immunological reactivity is consistent between the soluble CD14 antigen according to the first aspect of the present invention and the recombinant soluble CD14 fragment according to the second aspect of the present invention. Similarly, the recombinant soluble CD14 fragment according to the second aspect of the present invention is also useful as an analog in assaying the soluble CD14 antigen according to the first aspect of the present invention by a competitive method.

Furthermore, since the recombinant soluble CD14 fragment according to the second aspect of the present invention has immunological nature similar to that of the soluble CD14 antigen according to the first aspect of the present invention, it can be used as a specific binding target in screening for an antibody that can be used in assaying the soluble CD14 antigen according to the first aspect of the present invention. Such an assay can be accomplished, of course, by using the soluble CD14 antigen according to the first aspect of the present invention for the specific binding target. The soluble CD14 antigen, however, is present in the living body only in a minute amount, and therefore, the recombinant soluble CD14 fragment according to the second aspect of the present invention would serve as a particularly useful substitute.

As described above, the recombinant soluble CD14 fragment according to the second aspect of the present invention is useful for various applications, and this usefulness can be ascribed to the characteristic features 1) to 3). In other words, the recombinant soluble CD14 fragment according to the second aspect of the present invention having the characteristic features 1) to 3) is not represented by its sequence but by the function including the physical properties and the immunological nature of the CD14 fragment.

The recombinant soluble CD14 fragment according to the second aspect of the present invention has further characteristic feature that it does not bind to LPS. Although no specific indication of the peptide is included in WO96/20956, it discloses a peptide which contains 8 to 60 amino acids including positions 57 to 64 of the human CD14 and which binds to LPS. This peptide and the recombinant soluble CD14 fragment according to the second aspect of the present invention are not identical, as clearly understood by the fact that the recombinant soluble CD14 fragment according to the second aspect of the present invention has the characteristic feature 4) as described above.

The step of cleaving the fragment wherein cleavage site of the predetermined protease has been incorporated by insertion or substitution with the predetermined protease may be accomplished by the reaction commonly used in the art under the optimal conditions of the predetermined protease. For example, when the predetermined protease is PreScission Protease, the cleavage reaction may be allowed to take place overnight at 4° C. with the ratio of the enzyme to the substrate kept in the range of 0.001 to 10:1 (U:μg). When the predetermined protease is thrombin, cleavage reaction by the thrombin may be allowed to take place overnight at 22° C. with the ratio of the enzyme to the substrate kept in the range of 0.001 to 10:1 (U:μg). When the predetermined protease is Factor Xa, the cleavage reaction may be allowed to take place overnight by adding the ingredients so that the ratio of the enzyme to the substrate is in the range of 0.0008 to 8:1 (U:μg).

With regard to the step of recovering the fragment of the N terminal side, this step can be accomplished as described above for the purification of the fragment of the present invention or the like.

The production process as described above is capable of producing the fragment of the present invention or the like at a high yield with high product consistency and at a commercial scale.

Alternatively, the fragment of the present invention can be chemically synthesized by a common method used in the art, and the fragment produced by such chemical synthesis is also within the scope of the fragment of the present invention. For example, the fragment may be produced by synthesis on a commercially available peptide synthesizer, or by synthesizing the fragments of the fragment of the present invention, and ligating the thus synthesized fragments.

<Fourth Aspect>

Fourth aspect of the present invention is a method for diagnosing or detecting sepsis in which the soluble CD14 antigen according to the first aspect of the present invention is assayed. Use of the sepsis diagnosing or detecting method according to the fourth aspect of the present invention enables diagnosis or detection of the sepsis in the subject.

This method preferably contains the following steps 1) to 3):

1) assaying the soluble CD14 antigen according to the first aspect of the present invention in the blood collected from a subject;
2) comparing the assayed value with the standard value for a normal donor; and
3) evaluating whether the subject has sepsis.

In the step 1), the blood collected from the subject may be either as-collected blood from the subject, namely, a whole blood, or a plasma or serum prepared from the as-collected blood. The step 1) is preferably a step in which the soluble CD14 antigen according to the first aspect of the present invention is measured after preparing the blood into the plasma or the serum. "Assaying the soluble CD14 antigen according to the first aspect of the present invention" basically means measuring the quantity of the soluble CD14 antigen according to the first aspect of the present invention. However, it is also possible to measure the quantity per unit solution, namely, the concentration. In this step, it is important to obtain an assay result in the unit that enables comparison with the standard value in the following step 2).

In step 1), the assay is preferably conducted by a sandwich immunoassay in view of assay convenience. For example, such immunoassay can be accomplished by using the assay method according to the sixth aspect of the present invention, and by using the assay kit according to the fifth aspect of the present invention as will be described below. The step 1), however, is not limited to such an assay method, and the assay may be carried out, for example, by separating the soluble CD14 antigen according to the first aspect of the present invention in the blood, plasma, or serum collected from the subject by electrophoresis, and measuring the concentration or width of the detected band by densitometry. In a preferred embodiment of this method, the separation is conducted by SDS-PAGE under non-reducing conditions, and then, the band is detected by western blotting using the antibody used in the assay kit according to the fifth aspect of the present invention. Other assay methods include separation and detection by mass spectroscopy, HPLC, gas chromatography, and TLC.

The step 2) is a step conducted by preliminarily obtaining the assay results from normal donors, and standardizing the assay results, for example, by calculating the average or by setting a standard range; and using this standardized value or range of the normal donors for the standard which is compared with the value determined in the step 1). For example, the standard value for the normal donors may be determined by using "the average value+2SD or 3SD" of the normal donor for the cut off value. Alternatively, the step 2) may be accomplished by preliminarily determining the standard value for the sepsis patients, and comparing the value determined in the step 1) with this value. This step can be carried out instead of the step of comparing with the standard value of the normal donor of the step 2).

The step 3) is a step of evaluating whether the subject is sepsis (positive) or not sepsis (negative) on the basis of the results of the comparison in the step 2). However, the evaluation may also include "pseudopositive" evaluation or predictive diagnosis in addition to the "positive" and "negative" evaluations. For example, when the assay result is compared with the standard range of the normal donors set at 0 to 0.1 μg/mL and the sepsis patient value of 0.2 μg/mL or higher, the results can be evaluated as "negative" when the value of the subject is in the range of 0 to 0.1 μg/mL; "pseudopositive" when the value of the subject is in the range of 0.1 to 0.2 μg/mL; and "positive" or "high probability of developing sepsis within 24 hours" when the value of the subject is 0.2 μg/mL or higher.

In clinical tests, stability of the soluble CD14 antigen according to the first aspect of the present invention in the specimen may play the key factor. For example, when the sample is repeatedly frozen and thawed, or left for a long period at room temperature, the soluble CD14 antigen according to the first aspect of the present invention in the serum may become decomposed so that the assay can no longer be carried out, or the high molecular weight CD14 in the serum may become decomposed to exhibit a structure equivalent or similar to that of the soluble CD14 antigen according to the first aspect of the present invention to give an erroneous result.

In view of such situation, various additives may be added to the serum in order to secure the stability of the soluble CD14 antigen according to the first aspect of the present invention and the high molecular weight CD14. Exemplary additives which may be added at the time of the blood collection include ethylenediaminetetraacetic acid (EDTA), heparin, and citric acid which are used in collecting the plasma. Alternatively, a protease inhibitor may be added to the serum as a stabilizer to thereby suppress the proteolysis. Examples of such protease inhibitor include antithrombin III, α1-antitrypsin, aprotinin, leupeptin, α2-macrogloblin, pepstatin, antipain, chymostatin, amastatin, tripsin inhibitor, phenylmethylsulfonyl fluoride (PMSF), EGTA, E-64, benzamidine, and 4-fluoro-(2-aminoethyl)benzenesulfonyl chloride (AEBSF). Furthermore, stability of the soluble CD14 antigen according to the first aspect of the present invention and the high molecular weight CD14 in the solution may be improved by adding a sugar such as lactose, sucrose, or toreharose, or a synthetic high molecular weight compound such as PEG.

<Fifth Aspect>

Fifth aspect of the present invention is a kit for assaying the soluble CD14 antigen according to the first aspect of the present invention in a specimen, the kit comprising at least one antibody which specifically binds to the soluble CD14 antigen according to the first aspect of the present invention or a fragment thereof.

The kit of the present invention comprises at least one antibody which specifically binds to the soluble CD14 antigen according to the first aspect of the present invention or a fragment thereof to enable the detection of the soluble CD14 antigen according to the first aspect of the present invention in the specimen. In the kit of the present invention, detection of the soluble CD14 antigen according to the first aspect of the present invention is realized by direct detection of the target soluble CD14 antigen according to the first aspect of the present invention. The kit of the present invention is preferably the one which only detects the soluble CD14 antigen according to the first aspect of the present invention, and which does not detect human high molecular weight soluble CD14 antigen or 36 kDa soluble CD14 protein. Indeed, the assay kit of the present invention will detect neither the human high molecular weight soluble CD14 protein nor the 36 kDa soluble CD14 protein even if the human serum were used as it is for the specimen with no further special treatment such as addition of a protein to the human serum or denaturing of the protein in the human serum. The fragment of the antibody" is Fab, Fab', or F(ab')$_2$ of the antibody.

The assay kit of the present invention is not particularly limited as long as it comprises at least one antibody which specifically binds to the soluble CD14 antigen according to the first aspect of the present invention or a fragment thereof, and the kit is capable of assaying the soluble CD14 antigen according to the first aspect of the present invention in the specimen. The assay kit of the present invention is preferably a kit for assaying the soluble CD14 antigen, in which the antibody which specifically binds to the soluble CD14 antigen according to the first aspect of the present invention or a fragment thereof included in the kit is any one of the following antibodies a) to d) or a fragment thereof:

a) an antibody which specifically binds to a peptide comprising the amino acid residues described in SEQ ID NO: 2;
b) an antibody produced by using a peptide comprising 8 to 16 consecutive amino acid residues selected from the amino acid sequence described in SEQ ID NO: 2 for the antigen;
c) an antibody produced by using a peptide comprising 16 amino acid residues described in SEQ ID NO: 2 for the antigen; and
d) an antibody which specifically binds to the recombinant soluble CD14 fragment according to the second aspect of the present invention or the recombinant soluble CD14 fragment according to the third aspect of the present invention.

More preferably, the assay kit of the present invention is an assay kit which comprises the antibody a), c), or d) or a fragment thereof. Still more preferably, the assay kit is an assay kit which comprises the antibody d) or a fragment thereof. Most preferably, the assay kit of the present invention is an assay kit which comprises an antibody which binds to the recombinant soluble CD14 fragment according to the second aspect of the present invention, or a fragment of the antibody.

The antibody d), namely, the recombinant soluble CD14 fragment according to the second aspect of the present invention or the recombinant soluble CD14 fragment according to the third aspect of the present invention ("the recombinant soluble CD14 fragment according to the second aspect of the present invention" and "the recombinant soluble CD14 fragment according to the third aspect of the present invention" are hereinafter sometimes together referred to as "the recombinant soluble CD14 fragments of the present invention") includes an antibody which has similar characteristic features as a) an antibody which specifically binds to a peptide comprising the amino acid residues described in SEQ ID NO: 2; b) an antibody produced by using a peptide comprising 8 to 16 consecutive amino acid residues selected from the amino acid sequence described in SEQ ID NO: 2 for the antigen; or c) an antibody produced by using a peptide comprising 16 amino acid residues described in SEQ ID NO: 2 for the antigen, and some are overlapping. Therefore, the antibody d) may include some of the antibodies a) to c). To clearly distinguish the antibody d) from the antibodies a) to c), the antibodies a) to c) may be excluded from the antibody d).

The antibody which specifically binds to the soluble CD14 antigen according to the first aspect of the present invention or a fragment thereof, and in particular, the antibody d) used in this kit is preferably an antibody which has been prepared by using the recombinant soluble CD14 fragment according to the second aspect of the present invention or the recombinant soluble CD14 fragment according to the third aspect of the present invention for the antigen, or a fragment thereof. Also preferred is an antibody prepared by using the soluble CD14 antigen according to the first aspect of the present invention for the antigen, or a fragment thereof. More preferred is an antibody prepared by using the recombinant soluble CD14 fragment according to the second aspect of the present invention for the antigen, or a fragment thereof. Also preferred is a monoclonal antibody prepared by using the recombinant soluble CD14 fragment according to the second aspect of the present invention for the antigen, or a fragment thereof. In particular, the antibody used is preferably an antibody which does not substantially bind to the human high molecular weight CD14 or a recombinant high molecular weight CD14 such as the soluble polypeptide having the amino acids of positions 1 to 356 at N terminal of the human CD14 (hereinafter referred to as the "rsCD14(1-356)").

The assay principle is not particularly limited as long as the antibody or a fragment thereof is used to immunologically assay the soluble CD14 antigen according to the first aspect of the present invention.

An assay kit is described in the following as an example of the assay principle, and in this assay kit, the antibody a), namely, "an antibody which specifically binds to the peptide comprising the amino acid residues described in SEQ ID NO: 2" or "a monoclonal antibody prepared by using the recombinant soluble CD14 fragment according to the second aspect of the present invention for the antigen" is used to detect the soluble CD14 antigen according to the first aspect of the present invention by sandwich immunoassay (this assay kit is hereinafter sometimes referred to as sandwich immunoassay kit).

The sandwich immunoassay can be carried out by using the techniques known in the art. Assay principle, application, and improvement are described, for example, in Ishikawa E. ed., "Supersensitive Enzyme Immunoassay", Gakkai-Shuppan Center (1993); Immunoassay Development Research Group, "Novel Use of Immunoassays and Their Use in the Development of Diagnostic and Therapeutic Agents", Keiei-Kyoiku Shuppan; and Ishikawa E. ed., "Enzyme Immunoassay (3rd ed.)", Igaku-Shoin (1987).

The sandwich immunoassay kit of the present invention comprises an antibody which specifically binds to the peptide comprising the amino acid residues described in SEQ ID NO: 2. The characteristic features and the production method of the antibody which specifically binds to the peptide comprising the amino acid residues described in SEQ ID NO: 2 are as described in the first aspect of the present invention. The antibody is not particularly limited, and the antibody may be either a polyclonal antibody or a monoclonal antibody.

Sandwich immunoassay is an assay typically accomplished by forming a complex of an antibody—an antigen— an antibody by using two or more antibodies which recognize the analyte protein by different sites.

First, an insoluble carrier having a first antibody bonded thereto is prepared for use as a solid phase or the reaction site. The specimen is added to the insoluble carrier of the solid phase for reaction. After reacting for a predetermined time, the solid phase is washed to remove the substance which failed to specifically bind to the solid phase. A labeled second antibody is then added, and after reacting for a predetermined time, the solid phase is washed to remove the labeled antibody which failed to form the complex. Quantity of the complex which became specifically bonded to the solid phase was qualitatively and quantitatively determined by utilizing the label. The sandwich assay may be carried out either in two stages as described above (two-step method) or by simultaneously adding the antigen and the labeled antibody in one stage (one-step method).

In the sandwich immunoassay kit of the present invention, the assay is accomplished by forming the complex of "an antibody which specifically binds to the peptide comprising the amino acid residues described in SEQ ID NO: 2" or "a monoclonal antibody prepared by using the recombinant soluble CD14 fragment according to the second aspect of the present invention for the antigen"—"the soluble CD14 antigen according to the first aspect of the present invention"—"a second binding substance which specifically binds to the soluble CD14 antigen according to the first aspect of the present invention".

The sandwich immunoassay kit of the present invention may be constituted from:

an insoluble carrier having "an antibody which specifically binds to the peptide comprising the amino acid residues described in SEQ ID NO: 2" or "a monoclonal antibody prepared by using the recombinant soluble CD14 fragment according to the second aspect of the present invention for the antigen" attached thereto, and a labeled second binding substance which binds to "the soluble CD14 antigen according to the first aspect of the present invention" (hereinafter sometimes referred to as "the second binding substance" for simplicity); or an insoluble carrier having the second binding substance attached thereto, and "a labeled antibody which specifically binds to the peptide comprising 16 amino acid residues described in SEQ ID NO: 2" or "a labeled monoclonal antibody prepared by using the recombinant soluble CD14 fragment according to the second aspect of the present invention for the antigen".

Exemplary second binding substances are antibodies which specifically bind to "the soluble CD14 antigen according to the first aspect of the present invention", and the antibody which specifically binds to "the soluble CD14 antigen according to the first aspect of the present invention" is not particularly limited, and may be either a polyclonal antibody or a monoclonal antibody. In view of compatibility with the sandwich immunoassay using an antibody which specifically binds to the peptide comprising the amino acid residues described in SEQ ID NO: 2, the second binding substance is preferably a monoclonal antibody, or a fragment of such monoclonal antibody. The antibody fragment may be Fab, Fab', or F(ab')$_2$ of the monoclonal antibody.

The antibody which specifically binds to the soluble CD14 antigen according to the first aspect of the present invention (hereinafter sometimes referred to as "the second antibody") is not particularly limited and it may be either an antibody which specifically binds to the soluble CD14 antigen according to the first aspect of the present invention, or an antibody which also specifically binds to the high molecular weight CD14. Preferably, the second antibody is an antibody which bind to "the soluble CD14 antigen according to the first aspect of the present invention" by a different binding region from "the antibody which specifically binds to the peptide comprising the amino acid residues described in SEQ ID NO: 2" or "the monoclonal antibody prepared by using the recombinant soluble CD14 fragment according to the second aspect of the present invention for the antigen". More preferably, the second antibody is an antibody wherein the second binding substance specifically binds to any one of the regions in the amino acid residues of positions 1 to 52 of the human high molecular weight CD14, or a fragment thereof; or an antibody which competes with or which shows cross reactivity with an antibody which specifically binds to any one of the regions in the amino acid residues of positions 1 to 52 of the human high molecular weight CD14, or a fragment thereof. Most preferably, the second antibody is an antibody wherein the second binding substance specifically binds to any one of the regions in the amino acid residues of positions 17 to 26 of "the soluble CD14 antigen according to the first aspect of the present invention", or a fragment thereof; or an antibody which competes with (or which shows cross reactivity with) an antibody which specifically binds to any one of the regions in the amino acid residues of positions 17 to 26 of "the soluble CD14 antigen according to the first aspect of the present invention", or a fragment thereof.

The second antibody can be prepared, for example, according to the production process described for the first aspect of the present invention by using the high molecular weight CD14, "the soluble CD14 antigen according to the first aspect of the present invention", a mixture of the high molecular weight CD14 and "the soluble CD14 antigen according to the first aspect of the present invention", or the recombinant CD14 for the antigen to thereby produce the polyclonal antibody or the monoclonal antibody. Embodiment of producing the second antibody by using a mixture of the high molecular weight CD14 and "the soluble CD14 antigen according to the first aspect of the present invention" and the recombinant CD14 for the antigen will be described later in Example 3.

As in the case of Example 3 as will be described below, a sandwich assay system is preferably constituted in advance before the actual assay from an antibody which specifically binds to the peptide comprising the amino acid residues described in SEQ ID NO: 2 and a candidate antibody for the second antibody to thereby select an adequate second antibody by confirming the assay sensitivity.

The antibody fragments Fab, Fab', and F(ab')$_2$ can be prepared by the method known in the art (Ishikawa E. ed., "Supersensitive Enzyme Immunoassay", Gakkai-Shuppan Center, 1993).

In the foregoing, a sandwich immunoassay accomplished by bonding the antibody to the insoluble carrier has been described. The sandwich immunoassay, however, can be accomplished also in a solution without using an insoluble carrier, for example, by reacting the antigen, the labeled antibody, and the second labeled second binding substance in a liquid phase to thereby measure the interaction between the label and the second label.

With regard to the sandwich immunoassay, the assay may be alternatively accomplished by a competitive method, in which the antigen in the specimen and the labeled antigen or the labeled antigen analogue are allowed to compete in the formation of the complex of the antibody—the antigen—the antibody.

In the sandwich immunoassay kit of the present invention, the assay is accomplished by forming the complex: "an antibody which specifically binds to the peptide comprising the amino acid residues described in SEQ ID NO: 2" or "a monoclonal antibody prepared by using the recombinant soluble CD14 fragment according to the second aspect of the present invention for the antigen"—the labeled "soluble CD14 antigen according to the first aspect of the present invention" (or it analogue)—"the second binding substance which binds to the soluble CD14 antigen according to the first aspect of the present invention".

The sandwich immunoassay kit of the present invention conducted by the competitive method may be constituted from:

an insoluble carrier having "an antibody which specifically binds to the peptide comprising the amino acid residues described in SEQ ID NO: 2" or "a monoclonal antibody prepared by using the recombinant soluble CD14 fragment according to the second aspect of the present invention for the antigen" attached thereto; the second binding substance; and the labeled "soluble CD14 antigen according to the first aspect of the present invention" or the labeled analogue of "the soluble CD14 antigen according to the first aspect of the present invention"; or "an antibody which specifically binds to the peptide comprising the amino acid residues described in SEQ ID NO: 2" or "a monoclonal antibody prepared by using the recombinant soluble CD14 fragment according to the second aspect of the present invention for the antigen", an insoluble carrier having the second binding substance attached thereto; and the labeled "soluble CD14 antigen according to the first aspect of the present invention" or the labeled analogue of "the soluble CD14 antigen according to the first aspect of the present invention".

Examples of the analog of "the soluble CD14 antigen according to the first aspect of the present invention" include the recombinant soluble CD14 fragment according to the second aspect of the present invention; a soluble polypeptide having the amino acids of positions 1 to 285 at the N terminal of the human CD14 (hereinafter referred to as the "rsCD14 (1-285)"), and rsCD14(1-307)S286C. Among these, the particularly preferred is the recombinant soluble CD14 fragment according to the second aspect of the present invention. The analog, however, is not particularly limited as long as it is capable of competing in the assay system with the soluble CD14 antigen according to the first aspect of the present invention in the specimen. The production methods of the rsCD14(1-285) and rsCD14(1-307)S286C are described in WO01/72993.

The sandwich immunoassay can also be carried out by another alternative method using a second specific binding. In this method, the assay is accomplished by forming the complex of an antibody—an antigen—an antibody—a second specific binding substance; or the complex of an antibody—an antigen—an antibody—a second specific binding substance—a specific binding partner of the second specific binding substance (hereinafter sometimes referred to as "the second specific binding partner").

More specifically, the sandwich immunoassay kit of the present invention is accomplished by forming a complex of "an antibody which specifically binds to the peptide comprising the amino acid residues described in SEQ ID NO: 2" or "a monoclonal antibody prepared by using the recombinant soluble CD14 fragment according to the second aspect of the present invention for the antigen"—"the soluble CD14 antigen according to the first aspect of the present invention"—"a second binding substance which binds to the soluble CD14 antigen according to the first aspect of the present invention"—a second specific binding substance; a complex of "an antibody which specifically binds to the peptide comprising the amino acid residues described in SEQ ID NO: 2" or "a monoclonal antibody prepared by using the recombinant soluble CD14 fragment according to the second aspect of the present invention for the antigen"—"the soluble CD14 antigen according to the first aspect of the present invention"—"a second binding substance which binds to the soluble CD14 antigen according to the first aspect of the present invention"—a second specific binding substance—a second specific binding partner; or a complex of "a second binding substance which binds to the soluble CD14 antigen according to the first aspect of the present invention"—"the soluble CD14 antigen according to the first aspect of the present invention"—"an antibody which specifically binds to the peptide comprising the amino acid residues described in SEQ ID NO: 2" or "a monoclonal antibody prepared by using the recombinant soluble CD14 fragment according to the second aspect of the present invention for the antigen"—a second specific binding substance—a second specific binding partner.

With regard to the constitution of the sandwich immunoassay kit of the present invention using the second specific binding, for example, it may further comprise a labeled second specific binding substance when the partner of the second specific binding substance is "an antibody which specifically binds to the peptide comprising the amino acid residues described in SEQ ID NO: 2" or "a monoclonal antibody prepared by using the recombinant soluble CD14 fragment according to the second aspect of the present invention for the antigen", or "the second binding substance which binds to the soluble CD14 antigen according to the first aspect of the present invention". Exemplary second specific binding substance is an antibody against the partner of the second specific binding substance.

When the partner of the second specific binding substance is the second specific binding partner, the kit comprises "an antibody which specifically binds to the peptide comprising the amino acid residues described in SEQ ID NO: 2, to which the second specific binding substance has been bonded" or "a monoclonal antibody produced by using the recombinant soluble CD14 fragment according to the second aspect of the present invention for the antigen, to which the second specific binding substance has been bonded"; a labeled second binding substance which binds to the soluble CD14 antigen according to the first aspect of the present invention; and an insoluble carrier having the second specific binding partner bonded thereto; or alternatively, a labeled antibody which specifically binds to the peptide comprising the amino acid residues described in SEQ ID NO: 2 or "a monoclonal antibody produced by using the recombinant soluble CD14 fragment according to the second aspect of the present invention for the antigen, which has been labeled"; a second binding substance which binds to "the soluble CD14 antigen according to the first aspect of the present invention" having a second specific binding substance bonded thereto"; and an insoluble carrier having the second specific binding partner bonded thereto.

Exemplary combinations of the second specific binding substance and the second specific binding partner include an antigen and its antibody; a ligand and its receptor; a substance containing a sugar chain and lectin; and biotin and avidin or streptavidin.

Exemplary sandwich immunoassays also include, in addition to those described above, an assay conducted by using an antibody against an antibody, namely, an anti-immunoglobulin antibody to form a complex of an antibody—an antigen—an antibody—an anti-immunoglobulin antibody; an assay using an anti-immunoglobulin antibody and a second specific binding to form an anti-immunoglobulin antibody—an antibody—an antigen—an antibody—a second specific binding substance—a second specific binding partner.

In the sandwich immunoassay kit of the present invention, the assay is accomplished by forming a complex of "an antibody which specifically binds to the peptide comprising the amino acid residues described in SEQ ID NO: 2" or "a monoclonal antibody prepared by using the recombinant soluble CD14 fragment according to the second aspect of the present invention for the antigen"—"the soluble CD14 antigen according to the first aspect of the present invention"—"a second binding substance which binds to the soluble CD14 antigen according to the first aspect of the present invention"—an anti-immunoglobulin antibody; a complex of "an antibody which specifically binds to the peptide comprising the amino acid residues described in SEQ ID NO: 2" or "a monoclonal antibody prepared by using the recombinant soluble CD14 fragment according to the second aspect of the present invention for the antigen"—"the soluble CD14 antigen according to the first aspect of the present invention"—"a second binding substance which binds to the soluble CD14 antigen according to the first aspect of the present invention"—an anti-immunoglobulin antibody; an anti-immunoglobulin antibody—"an antibody which specifically binds to a peptide comprising the amino acid residues described in SEQ ID NO: 2" or "a monoclonal antibody produced by using the recombinant soluble CD14 fragment according to the second aspect of the present invention for the antigen"—"the soluble CD14 antigen according to the first aspect of the present invention"—"a second binding substance which binds to the soluble CD14 antigen according to the first aspect of the present invention"—a second specific binding substance—a second specific binding partner; or an anti-immunoglobulin antibody—"a second binding substance which binds to the soluble CD14 antigen according to the first aspect of the present invention"—"the soluble CD14 antigen according to the first aspect of the present invention"—"an antibody which specifically binds to the peptide comprising the amino acid residues described in SEQ ID NO: 2" or "a monoclonal antibody prepared by using the recombinant soluble CD14 fragment according to the second aspect of the present invention for the antigen"—the second specific binding substance—the second specific binding partner.

Irrespective of the type of the sandwich immunoassay, any such assay conducing the assay by forming a complex of "an antibody which specifically binds to the peptide comprising the amino acid residues described in SEQ ID NO: 2" or "a monoclonal antibody prepared by using the recombinant soluble CD14 fragment according to the second aspect of the present invention for the antigen"—"the soluble CD14 antigen according to the first aspect of the present invention"—"a second binding substance which binds to the soluble CD14 antigen according to the first aspect of the present invention" is within the scope of the assay of the present invention even if a solid phase or a label substance were included by using the second specific binding.

In other words, irrespective of the type of the sandwich immunoassay, a sandwich immunoassay kit is within the scope of the kit of the present invention as long as the assay kit contains "an antibody which specifically binds to the peptide comprising the amino acid residues described in SEQ ID NO: 2" or "a monoclonal antibody prepared by using the recombinant soluble CD14 fragment according to the second aspect of the present invention for the antigen". Similarly, a sandwich immunoassay kit is within the scope of the kit of the present invention as long as the assay kit contains an antibody of any one of the above a) to d). (In the following, the same applies to the expression "as long as "an antibody which specifically binds to the peptide comprising the amino acid residues described in SEQ ID NO: 2" or "a monoclonal antibody prepared by using the recombinant soluble CD14 fragment according to the second aspect of the present invention for the antigen" is contained").

The insoluble carrier used for the sandwich immunoassay kit of the present invention may be, for example, beads, latex particles, magnetic particles, a plate, a tube, or a membrane. The beads, the plate, and the tube may be those produced from polystyrene, nylon, glass, silicone rubber, stainless steel, plastic, or the like. The membrane may be the one produced from cellulose, cellulose derivative, nitrocellulose, porous synthetic polymer, or glass fiber, a fabric, a nonwoven, a filter paper, or the like. The beads, the latex particles, and the magnetic particles may be those having spherical shape, which is advantageous in view of reduced space during the storage. The plate and the tube may be used in the form of a well, and this form is advantageous in view of the compatibility with commercially available automated assay system, plate reader, and the like. The membrane can be used in the immunochromatography and flow through test as will be described below.

The binding of the antibody which specifically binds to the peptide comprising the amino acid residue described in SEQ ID NO: 2, the second binding substance, the second specific binding substance or its partner, or the anti-immunoglobulin antibody to the insoluble carrier may be accomplished, for example, by thermal adsorption, chemical bonding, or the like.

The non-adsorption surface of the insoluble carrier having no such substance bonded thereto is preferably blocked by a substance which does not affect the assay system in order to improve specificity or sensitivity of the assay system. Exemplary such substance having no effects on the assay system include proteins such as BSA and casein, and surfactants such as Tween20 and NP-40.

The label used in the sandwich immunoassay kit of the present invention may be an enzyme such as peroxidase, alkaline phosphatase, $\beta$-D-galactosidase, oxidase, or uricase; a chemiluminescent substance such as acridinium or its derivative, or aequorin or modified aequorin; a fluorescent substance such as FITC, europium (Eu), samarium (Sm), or other lanthanoid fluorescent substance; dye; gold colloid; colored latex; or an isotope.

For example, when the enzyme used is peroxidase, 3,3',5,5'-tetrabenzidine, 1,2-phenylenediamine, or the like may be used for the chromogenic substrate, and when the enzyme used is an alkaline phosphatase, 4-nitrophenylphosphate or the like may be used for the chromogenic substrate, and when the enzyme used is $\beta$-D-galactosidase, 2-nitrophenyl.$\beta$-D-galactoside or the like may be used for the chromogenic substrate.

The labeling with enzyme of the antibody which specifically binds to the peptide comprising the amino acid residues described in SEQ ID NO: 2, the second binding substance, the second specific binding substance or its partner, or anti-immunoglobulin antibody may be accomplished by two stage glutaraldehyde method, periodic acid method, maleimide method, pyridyl disulfide method, or the like.

The label other than the enzyme may also be attached by a method known in the art such as thermal adsorption and chemical bonding.

Labeling with an enzyme is preferable since the assay can be accomplished at a relatively high sensitivity, and with an absorbance measuring system commonly used in the art when the chromogenic substrate is the one as mentioned above.

When a chemiluminescent substance, a fluorescent substance, a colored label, or an isotope is used for the label, the assay can be accomplished by using a measuring system compatible with the label. When a fluorescent substance such as Eu, for example, cryptate (Eu$^{3+}$ cryptate) is used, fluorescence resonance energy transfer may be measured by using an allophycocyanin derivative such as XL665 for the second label.

For a handy assay kit such as a kit employing the immunochromatography or flow through test as will be described below, use of a dye, gold colloid, or colored latex is preferable since these labels can be visually observed.

The sandwich immunoassay kit of the present invention is characterized in that the assay is carried out by the sandwich immunoassay, and it contains an antibody which specifically binds to the peptide comprising the amino acid residues described in SEQ ID NO: 2. The sandwich immunoassay may be accomplished by technologies known in the art as described above, and the sandwich immunoassay kit of the present invention is not particularly limited any further than the above description as long as the kit is based on the sandwich immunoassay and it contains "an antibody which specifically binds to the peptide comprising the amino acid residues described in SEQ ID NO: 2" or "a monoclonal antibody prepared by using the recombinant soluble CD14 fragment according to the second aspect of the present invention for the antigen". More specifically, the sandwich immunoassay kit of the present invention includes "an antibody which specifically binds to the peptide comprising the amino acid residues described in SEQ ID NO: 2" or "a monoclonal antibody prepared by using the recombinant soluble CD14 fragment according to the second aspect of the present invention for the antigen" and other reagents that are necessary for the sandwich immunoassay, and the components of the kit are not particularly limited as long as the assay principle and the assay results are not interfered by such components.

Exemplary such optional components include a buffer or a diluent for the specimen, the labeled antibody, or the like, a chromogenic substrate (see above) suitable for the enzyme used if an enzyme is used in the labeled antibody, a blocking agent, a stopping reagent, and a washing solution. Preferably, the diluent is the one containing a substance that is also contained in the specimen, although the diluent is not particularly limited. When the specimen is serum, and the blood collection in the course of obtaining the serum has been conducted in the presence of EDTA or citric acid, the diluent preferably contains EDTA or citric acid at the same content. The diluent, for example, may contain 0.2 to 1 mg/ml of EDTA.

Exemplary such optional components also include a standard substance, which may be "the soluble CD14 antigen according to the first aspect of the present invention" or an analog of "the soluble CD14 antigen according to the first aspect of the present invention". Use of the recombinant soluble CD14 fragment of the present invention is particularly preferred for the standard substance.

The sandwich immunoassay kit of the present invention also includes the kits for immunochromatographic or flow through analysis in which the assay is accomplished on the principle of the sandwich immunoassay. The sandwich immunoassay kit of the present invention is also applicable to an assay by MEDIA process which electrochemically measures the signal from the label (JP-A 5-264552), an immunoassay using a microchip ("Bioscience and Industry", vol. 61, pages 449-454, 2003), time-resolved fluoroimmunoassay ("Analytical biochemistry" (US), 1984, vol. 137, pp. 335-343), and homogeneous immunoassay. The assay kits employing such assay principles are also included within the scope of the sandwich immunoassay kit of the present invention as long as the analyte is assayed by sandwich immunoassay, and the kit contains "an antibody which specifically binds to the peptide comprising the amino acid residues described in SEQ ID NO: 2" or "a monoclonal antibody prepared by using the recombinant soluble CD14 fragment according to the second aspect of the present invention for the antigen".

The sandwich immunoassay kit of the present invention has the characteristic feature that it contains "an antibody which specifically binds to the peptide comprising the amino acid residues described in SEQ ID NO: 2" or "a monoclonal antibody prepared by using the recombinant soluble CD14 fragment according to the second aspect of the present invention for the antigen", and it can specifically assay the soluble CD14 antigen according to the first aspect of the present invention. The specimen used for the sandwich immunoassay kit of the present invention is preferably an aqueous specimen. The particularly preferred are, for example, blood, serum, plasma, and other blood components, urine and other body fluids, cell culture supernatant, and eluate from the column, and these specimens can be successfully used in assaying the soluble CD14 antigen according to the first aspect of the present invention contained in these specimens. However, in the case of specimens other than human blood components, for example, human urine or other body fluids; blood components, urine, or other body fluids from non-human species; cell culture supernatant or eluate from a column, the kit can assay not only "the soluble CD14 antigen according to the first aspect of the present invention" but also proteins and polypeptides analogous to "the soluble CD14 antigen according to the first aspect of the present invention". The sandwich immunoassay kit of the present invention also includes the kit for assaying proteins and polypeptides analogous to "the soluble CD14 antigen according to the first aspect of the present invention" as long as it contains "an antibody which specifically binds to the peptide comprising the amino acid residues described in SEQ ID NO: 2" or "a monoclonal antibody prepared by using the recombinant soluble CD14 fragment according to the second aspect of the present invention for the antigen".

In addition, "an antibody which specifically binds to the peptide comprising the amino acid residues described in SEQ ID NO: 2" and "a monoclonal antibody prepared by using the recombinant soluble CD14 fragment according to the second aspect of the present invention for the antigen" in the foregoing description may be replaced with "an Fab, Fab', or (Fab')$_2$ fragment of the antibody which specifically binds to the peptide comprising the amino acid residues described in SEQ ID NO: 2" or "an Fab, Fab', or (Fab')$_2$ fragment of the monoclonal antibody prepared by using the recombinant soluble CD14 fragment according to the second aspect of the present invention for the antigen", respectively.

In the foregoing, embodiments of the sandwich immunoassay kit using the antibody a), namely, "an antibody which specifically binds to the peptide comprising the amino acid residues described in SEQ ID NO: 2" or "a monoclonal antibody prepared by using the recombinant soluble CD14 fragment according to the second aspect of the present invention for the antigen" have been described. The assay kit, however, can also be constituted by using the antibody b), namely, "an antibody produced by using a peptide comprising 8 to 16 consecutive amino acid residues selected from the amino acid sequence described in SEQ ID NO: 2 for the antigen", the antibody c), namely, "an antibody produced by using a peptide comprising 16 amino acid residues described in SEQ ID NO: 2 for the antigen", the antibody d), namely, "an antibody produced by using the soluble CD14 fragment according to the second aspect of the present invention for the antigen", or fragment Fab, Fab', or (Fab')$_2$ of such an antibody.

Exemplary assay principles other than the sandwich immunoassay include agglutination assay, solid phase binding assay, and solution reaction assay, and an assay kit adapted for each method may be constituted by using at least one antibody which specifically binds to "the soluble CD14 antigen according to the first aspect of the present invention" or a fragment thereof, and preferably, by using the antibody of the present invention or a fragment thereof. When the assay kit is constituted by using one antibody alone without using the second binding substance, the antibody which specifically binds to "the soluble CD14 antigen according to the first aspect of the present invention" or a fragment thereof preferably comprises an antibody which does not substantially bind to the full length soluble CD14 protein (hereinafter sometimes referred to as "the human high molecular weight CD14") in the human blood or the recombinant high molecular weight CD14 such as the soluble polypeptide containing the amino acids of the positions 1 to 356 at the N terminal of the human CD14 (hereinafter referred to as the "rsCD14(1-356)").

In the agglutination assay, an antibody is bonded to the surface of particles, the particle are allowed to agglutinate by utilizing the presence of the antigen, and specific qualification or quantitation of the antigen is conducted by using the degree of the agglutination for the index.

In the immunoassay kit of the present invention utilizing the agglutination assay, the assay is conducted, for example, by forming "the antibody which specifically binds to a peptide comprising the amino acid residues described in SEQ ID NO: 2" or "the monoclonal antibody produced by using the recombinant soluble CD14 fragment according to the second aspect of the present invention for the antigen"—"the soluble CD14 antigen according to the first aspect of the present invention" and agglutinating the complex.

The immunoassay kit of the present invention utilizing the agglutination assay comprises the particles having the antibody of the present invention bonded on its surface.

The particles used may be those commonly used in the art such as latex particles, erythrocytes (for example, sheep erythrocytes), gelatin particles, microbeads, or carbon particle.

The solid phase binding assay is an assay which is accomplished by forming an antibody—antigen complex on the solid phase. In this assay, a specimen containing the antigen is adsorbed on an insoluble carrier (i.e. solid phase), and a labeled antibody is then added for reaction. The amount of the complex that became bonded to the solid phase is then measured by using the label for specific qualification or quantitation.

The competitive assay is conducted, for example, by allowing an antigen analog to be adsorbed on an insoluble carrier for competition with the reaction between the labeled antibody and the antigen in the specimen, and measuring the amount of the labeled antibody that became specifically bonded to the antigen analog. Another competitive assay is conducted by allowing an antibody to be adsorbed on an insoluble carrier for competition of the labeled antigen analog with the reaction between the antibody and the antigen in the specimen, and measuring the amount of the labeled antigen analog that became specifically bonded to the antibody.

In the solid phase binding immunoassay kit of the present invention, the assay is accomplished by forming a complex of "an antibody which specifically binds to the peptide comprising the amino acid residues described in SEQ ID NO: 2" or "a monoclonal antibody prepared by using the recombinant soluble CD14 fragment according to the second aspect of the present invention for the antigen"—"the soluble CD14 antigen according to the first aspect of the present invention"; a complex of "an antibody which specifically binds to the peptide comprising the amino acid residues described in SEQ ID NO: 2" or "a monoclonal antibody prepared by using the recombinant soluble CD14 fragment according to the second aspect of the present invention for the antigen"—the labeled "soluble CD14 antigen according to the first aspect of the present invention" (or its analog); or a complex of "a labeled antibody which specifically binds to the peptide comprising the amino acid residues described in SEQ ID NO: 2" or "a labeled monoclonal antibody produced by using the recombinant soluble CD14 fragment according to the second aspect of the present invention for the antigen"—"the soluble CD14 antigen according to the first aspect of the present invention" (or its analog).

The insoluble carrier, the analog of "the soluble CD14 antigen according to the first aspect of the present invention", the label, and the reagent adsorbed are as described in the explanation of the sandwich immunoassay kit.

The solution reaction method is a method in which an antigen and a labeled antibody are reacted in liquid phase, and the antigen, the antibody, and the antigen—antibody complex are separated by means of coagulation or physicochemical technique using the antibody for specific qualification or quantitation of "the soluble CD14 antigen according to the first aspect of the present invention".

In the foregoing description, "an antibody which specifically binds to the peptide comprising the amino acid residues described in SEQ ID NO: 2" or "a monoclonal antibody prepared by using the recombinant soluble CD14 fragment according to the second aspect of the present invention for the antigen" may be replaced with "an antibody produced by using a peptide comprising 8 to 16 consecutive amino acid residues selected from the amino acid sequence described in SEQ ID NO: 2 for the antigen", "an antibody produced by using a peptide comprising 16 amino acid residues described in SEQ ID NO: 2 for the antigen", "an antibody produced by using the soluble CD14 antigen according to the first aspect of the present invention for the antigen", or "an antibody produced by using the recombinant soluble CD14 fragment according to the third aspect of the present invention for the antigen", or "an Fab, Fab', or (Fab')$_2$ fragment of such an antibody".

Assay principles of the assay kit of the present invention have been described in the foregoing. However, these are not the sole principles of the assay kit of the present invention, and an assay kit is included within the scope of the present invention as long as it contains an antibody which specifically binds to at least one "soluble CD14 antigen according to the first aspect of the present invention" or a fragment thereof, and it can directly assay "the soluble CD14 antigen according to the first aspect of the present invention". The principle of the immunoassay may comprise those known in the art as described, for example, in the above-mentioned Ishikawa E. ed., "Supersensitive Enzyme Immunoassay", Gakkai-Shuppan Center (1993); Immunoassay Development Research Group, "Novel Use of Immunoassays and Their Use in the Development of Diagnostic and Therapeutic Agents", Keiei-Kyoiku Shuppan; and Ishikawa E. ed., "Enzyme Immunoassay (3rd ed.)", Igaku-Shoin (1987).

"The soluble CD14 antigen according to the first aspect of the present invention" which can be specifically assayed by the kit of the present invention increases in the patient suffering from sepsis. Accordingly, measurement of "the soluble CD14 antigen according to the first aspect of the present invention" would provide an index for the diagnosis of sepsis, and the kit of the present invention is useful in diagnosing the sepsis.

"The antibody which specifically binds to a peptide comprising the amino acid residues described in SEQ ID NO: 2" or "the monoclonal antibody produced by using the recombinant soluble CD14 fragment of the present invention for the antigen" is preferably an antibody which has a dissociation constant (KD) expressed in term of the affinity of the antibody for the peptide or "the recombinant soluble CD14 fragment of the present invention" of less than $10^{-7}$M, more preferably $10^{-8}$M or less, and still more preferably $10^{-9}$M or less.

In the production of "the antibody which specifically binds to a peptide comprising the amino acid residues described in SEQ ID NO: 2", the peptide used for the antigen is a peptide containing at least 8 consecutive amino acids, preferably a peptide containing at least 10 consecutive amino acids, more preferably a peptide containing at least 12 consecutive amino acid, and most preferably a peptide containing at least 16 consecutive amino acids described in SEQ ID NO: 2. In addition, as long as the peptide contains any one of the at least 8 consecutive amino acids of SEQ ID NO: 2, the peptide is not particularly limited for the amino acid sequence other than the at least 8 consecutive amino acids of the SEQ ID NO: 2. The peptide, however, is preferably the one in which all the amino acid sequences within the peptide are those found in the SEQ ID NO: 2.

The antibody is preferably the one produced by using the peptide containing at least 8 consecutive amino acids, preferably the peptide containing at least 10 consecutive amino acids, more preferably the peptide containing at least 12 consecutive amino acid, and most preferably the peptide containing at least 16 consecutive amino acids described in SEQ ID NO: 2 for the antigen.

In the production of "the antibody produced by using a peptide comprising 8 to 16 consecutive amino acid residues selected from the amino acid sequence described in SEQ ID NO: 2 for the antigen", the number of the amino acid residues of the peptide is not particularly limited as long as the peptide is the one comprising 8 to 16 consecutive amino acid residues selected from the amino acid sequence described in SEQ ID NO: 2. The antibody is preferably the one produced by using a peptide comprising at least 10 consecutive amino acids, more preferably at least 12 consecutive amino acid, and most preferably at least 16 consecutive amino acids for the antigen. In other words, the antibody is most preferably "an antibody produced by using a peptide comprising 16 consecutive amino acid residues of SEQ ID NO: 2 for the antigen".

Also, "the soluble CD14 antigen according to the first aspect of the present invention" has a molecular weight different from that of the high molecular weight CD14, and an amino acid sequence shorter than that of the high molecular weight CD14. Accordingly, the structure of the "the soluble CD14 antigen according to the first aspect of the present invention" in blood should be different from that of the high molecular weight CD14. It is conceived that this difference in the structure leads to the difference in the reactivity with the antibody, and the strong bonding, namely, the high affinity for "the soluble CD14 antigen according to the first aspect of the present invention" of the antibodies a) to d) which are the preferable examples of the antibody which specifically binds to "the soluble CD14 antigen according to the first aspect of the present invention" included in the assay kit according to the fifth aspect of the present invention (hereinafter sometimes referred to as "the antibodies a) to d)" for the sake of simplicity).

Each of the antibodies a) to d) may be either a polyclonal antibody or a monoclonal antibody. The animal species used to obtain the antibodies of the present invention is not particularly limited, and use of a rabbit, a goat, or the like is preferred in view of the ease of the antibody production. The type of the molecule is also not particularly limited, and an immunoglobulin of any class, subclass, or isotype may be employed.

The peptide used for the immunogen may be produced by any method commonly used in the art, for example, by using a peptide synthesizer (peptide synthesizer model 433A manufactured by PerkinElmer Japan) or by genetic recombination (see "New Protocols of Cytoengineering Experiments" edited by Antitumor Research Section, The Institute of Medical Science, The University of Tokyo, and published from Shujun-sha).

For example, the peptide comprising at least 8 consecutive amino acids of the amino acid residues described in SEQ ID NO: 2 can be synthesized by Fmoc method by using a peptide synthesizer (model 433A), and after deprotection by TFA and cleavage from the resin, it can be purified by using a C18 HPLC column (Capcell-pak, Shiseido Co., Ltd.) to prepare the target peptide.

When the antigen is a protein, it can be used for the immunogen with no further treatment. However, a peptide of the size equal to or smaller than 8 to 30 amino acid residues generally may not have immunogenicity due to the low molecular weight. In such a case, the peptide is bonded to a carrier, or a MAP peptide is prepared by Multiple Antigen Peptide (MAP) method to impart to the molecule a molecular weight sufficient to develop the immunogenicity in order to enable its use for an antigen.

Exemplary carriers bonded to such peptide include a carrier protein and a polymer. The carrier protein employed may be a foreign protein such as bovine serum albumin, keyhole limpet hemocyanin (KLH), thyroglobulin, and ovalbumin. These carrier proteins may be bonded to the peptide by means of the functional group in the side chain of the amino acid of the peptide or such a carrier protein, or by incorporating maleimide group, N-hydroxysuccinimide (NHS) group, or aldehyde group. Exemplary polymers include sugars such as mannan and chitosan, and polyvinyl pyrrolidone (PVA). These polymers may be bonded to the peptide by adsorption or the chemical bond as mentioned above.

Production of the recombinant soluble CD14 fragment of the present invention used for the antigen may be carried out as described for the second and third aspects of the present invention. When such fragment is used for the antigen, it can be used for the immunogen either with no further treatment or after binding to a carrier or the like.

The antibody of the present invention may be produced by a method known in the art (for example, see "Experimental Methods in Immunology" edited and published by Japanese Society for Immunology). For example, a polyclonal antibody may be produced by the process as described below.

20 to 1000 µg of the immunogen prepared as described above is mixed with an adjuvant such as Freund's complete adjuvant, RIBI adjuvant, or ALUM for use in the immunization of various animals. Exemplary animals used include horse, sheep, goat, pig, rabbit, rat, and mouse. The immunization can be accomplished, for example, by intramuscular administration, intradermal administration, subcutaneous administration, intraperitoneal administration, lymph node administration, or other method, and after initial administration, the animal may be boostered at an interval of 1 to 4 weeks by administering the immunogen admixed with an adjuvant such as Freund's incomplete adjuvant, RIBI adjuvant, or ALUM in a similar manner or by directly adding the immunogen to the vein. An antiserum may be prepared by collecting the blood from the immunized animal by any blood collection method commonly used in the art, for example, from carotid artery, ear vein, heart, leg vein, or the like, and separating the serum, for example, by centrifugation. γ globulin fraction is then salted out by adding ammonium sulfate, sodium sulfate, or the like for precipitation. The precipitate is dialyzed against an appropriate buffer, and subjected to an affinity matrix such as protein A or protein G capable of specifically purifying the γ globulin to obtain the purified polyclonal antibody of IgG fraction against the target peptide. The product can be specifically purified by selecting an antibody which specifically binds to the antigen as described above.

A monoclonal antibody may be produced by the process as described below.

An immunocyte of the immunized mammal is fused with a myeloma cell to produce a hybridoma, and the clone producing an antibody which specifically binds to the peptide as described above is selected to produce the antibody of the present invention. The immunogen used is preferably a peptide comprising at least 10 consecutive amino acid residues, more preferably at least 12 consecutive amino acid residues, and most preferably 16 consecutive amino acid residues of positions 53 to 68.

The mammal immunized is not particularly limited. The mammal, however, is preferably selected by taking compatibility with the myeloma cell used for the cell fusion into consideration, and use of a mammal such as mouse, rat, and hamster is preferred. Various known myeloma cells can be employed including myeloma cells such as P3, P3U1, SP2/O, NS-1, YB2/0, and Y3-Ag1.2.3.

The immunization can be accomplished by the method known in the art, for example, by administering the antigen in the peritoneal cavity, under the skin, in the vein, or in the food pad. This antigen administration may be combined with the administration of the adjuvant, and the antigen is preferably administered two or more times. The immunocyte is preferably a splenocyte or a cell of the lymph node collected several days, for example, 3 days after the final administration of the antigen. The fusion of the immunocyte and the myeloma cell may be conducted by a method known in the art such as the method of Milstein (Methods in Enzymol., vol. 73, page 3), by using a fusion agent such as polyethyleneglycol (PEG), or by electrofusion method.

The mixing ratio of the immunocyte and the myeloma cell is not particularly limited as long as these cells can fuse with each other. The myeloma cell, however, is preferably used at 1/10 to equal amount of the immunocyte. When the cells are fused by using PEG (average molecular weight, 1,000 to 4,000), PEG is preferably used at a concentration of 50% although the concentration is not particularly limited. A fusion promoter such as dimethyl sulfoxide (DMSO) may also be added to improve the fusion efficiency. The fusion may be initiated by adding the PEG solution which has been heated to a temperature of 37° C., and after allowing the reaction to proceed for 1 to 5 minutes, the reaction may be completed by adding the culture medium. The thus formed hybridoma may be cultivated for 1 to 7 days on a selective culture such as a culture containing hypoxanthine, thymidine, and aminopterin (HAT medium) to separate cells which failed to fuse.

The resulting hybridoma is further selected on the basis of the type of the antibody produced. The selected hybridoma is made monoclonal by means of the limiting dilution method known in the art to thereby establish the monoclonal antibody-producing hybridoma. Activity of the antibody produced by the hybridoma may be detected by a method known in the art such as ELISA, agglutination, or radioimmunoassay. The thus established hybridoma may be cultivated by a method known in the art to thereby obtain the monoclonal antibody from the culture supernatant. Alternatively, the hybridoma may be administered to a mammal which has compatibility with the particular hybridoma for propagation, and the monoclonal antibody may be collected from the ascites. The purification of the antibody may be accomplished by salting out, gel filtration, ion exchange chromatography, affinity chromatography, or other purification means.

As described in the section of the diagnosis method according to the fourth aspect of the present invention, the value measured may fluctuate by the effect of the stability of the soluble CD14 antigen and the high molecular weight CD14 of the present invention. Therefore, in order to improve the performance of the kit, the antibody used is preferably the one having a high specificity for the soluble CD14 antigen as well as low reactivity with the substance that may change during the storage causing fluctuation of the measurement value. An antibody used for constituting the kit may be screened to thereby obtain an antibody which does not cause such fluctuation.

<Sixth Aspect>

Sixth aspect of the present invention is a method for immunologically assaying "the soluble CD14 antigen according to the first aspect of the present invention" in which at least one antibody which specifically binds to "the soluble CD14 antigen according to the first aspect of the present invention" or a fragment thereof is allowed to specifically bind to "the soluble CD14 antigen according to the first aspect of the present invention".

The assay method according to the sixth aspect of the present invention is a method for immunologically assaying "the soluble CD14 antigen according to the first aspect of the present invention" which does not detect the human high molecular weight CD14; which uses at least one antibody which specifically binds to "the soluble CD14 antigen according to the first aspect of the present invention"; and which directly assays the "the soluble CD14 antigen according to the first aspect of the present invention" in the specimen. Preferably, the assay method uses any one of the following antibodies a) to d) or a fragment of such an antibody:

a) an antibody which specifically binds to a peptide comprising the amino acid residues described in SEQ ID NO: 2;

b) an antibody produced by using a peptide comprising 8 to 16 consecutive amino acid residues selected from the amino acid sequence described in SEQ ID NO: 2 for the antigen;

c) an antibody produced by using a peptide comprising 16 amino acid residues described in SEQ ID NO: 2 for the antigen; and d) an antibody which specifically binds to the recombinant soluble CD14 fragment according to the second aspect of the present invention or the recombinant soluble CD14 fragment according to the third aspect of the present invention.

More preferably, this assay method is an assay method which comprises the use of the antibody a), c), or d) or a fragment of such an antibody. Still more preferably, this assay method is an assay kit which comprises the antibody d) or a fragment thereof. In the above description, the antibody fragment may be Fab, Fab', or F(ab')$_2$ of such monoclonal antibody.

This assay method is also preferably an assay method for assaying "the soluble CD14 antigen according to the first aspect of the present invention" in which a second binding substance which binds to "the soluble CD14 antigen according to the first aspect of the present invention" is used to conduct a sandwich immunoassay between an antibody of any one of the above a) to d) or a fragment thereof and the second binding substance to assay "the soluble CD14 antigen according to the first aspect of the present invention".

The antibody of any one of the above a) to d) may be used as a solid phase antibody, a labeled antibody, or the like. The assay method also includes those utilizing a second specific binding, and an anti-immunoglobulin antibody. In such a case, the antibody which is any one of the a) to d) may be used as a free antibody, a second specific binding substance, or an antibody which is bonded to the partner of the second specific binding.

The assay method of the present invention may be conducted by sandwich immunoassay which may be either non-competitive or competitive, and also included are immunochromatography, flow through analysis, and the like.

The assay principle of the assay method of the present invention is not limited to sandwich immunoassay, and other method such as agglutination, solid phase binding method, and solution reaction method may also be employed.

Detailed assay method and preferable assay method are as described for the section of the kit according to the fifth aspect of the present invention.

<Seventh Aspect>

Seventh aspect of the present invention is an antibody which specifically binds to the soluble CD14 antigen according to the first aspect of the present invention. This aspect of the present invention, however, includes the following antibodies a) to d) which are also described in the Examples of WO2004/44005 (which was published after the priority date of this application), and there is some overlapping. Therefore, the antibody which specifically binds to the recombinant soluble CD14 fragment according to the second aspect of the present invention may include some of the following a) to d). The antibody of the second aspect of the present invention and the antibodies of the following a) to d) can be clearly distinguished by excluding the antibody of the following antibody a) to d) from the antibody of the second aspect of the present invention.

a) an antibody prepared by using a peptide comprising the amino acid residues described in SEQ ID NO: 2 for the antigen;

b) a polyclonal antibody prepared by using a peptide comprising the amino acid residues described in SEQ ID NO: 4 or SEQ ID NO: 5 for the antigen, c) F1031-8-3 antibody, and d) F1106-13-3 antibody.

It is to be noted that WO2004/44005 also describes an antibody which binds to the peptide comprising the amino acid residues described in SEQ ID NO: 2, SEQ ID NO: 4, or SEQ ID NO: 5; and an antibody prepared by using the peptide comprising 8 to 30 consecutive amino acid residues from the amino acid sequence described in SEQ ID NO: 6 for the antigen. On the other hand, the antibody which specifically binds to the recombinant soluble CD14 fragment according to the second aspect of the present invention may include some of such antibodies. For clear distinction, such antibodies may be excluded from the antibody which specifically binds to the recombinant soluble CD14 fragment according to the second aspect of the present invention.

"The antibody which specifically binds to the soluble CD14 antigen according to the first aspect of the present invention" according to the seventh aspect of the present invention does not substantially bind to the full length soluble CD14 protein in human blood or rsCD14(1-356), and it is preferably an antibody which specifically binds to the recombinant soluble CD14 fragment according to the second aspect of the present invention. It is also preferably an antibody which is a monoclonal antibody.

The antibody of the present invention can be prepared by using the soluble CD14 antigen according to the first aspect of the present invention for the antigen.

Use of the antibody according to the seventh aspect of the present invention enables assay of the soluble CD14 antigen according to the first aspect of the present invention, and constitution of the "assay kit for assaying the soluble CD14 antigen according to the first aspect of the present invention" according to the fifth aspect of the present invention.

<Eighth Aspect>

Eighth aspect of the present invention is an antibody which specifically binds to the recombinant soluble CD14 fragment according to the second aspect of the present invention. This aspect of the present invention, however, includes the following antibodies a) to d) which are also described in the Examples of WO2004/44005 (which was published after the priority date of this application), and there is some overlapping. Therefore, the antibody which specifically binds to the recombinant soluble CD14 fragment according to the second aspect of the present invention may include some of the following a) to d). The antibody of the second aspect of the present invention and the antibodies of the following a) to d) can be clearly distinguished by excluding the antibody of the following antibody a) to d) from the antibody of the second aspect of the present invention.

a) an antibody prepared by using a peptide comprising the amino acid residues described in SEQ ID NO: 2 for the antigen;

b) a polyclonal antibody prepared by using a peptide comprising the amino acid residues described in SEQ ID NO: 4 or SEQ ID NO: 5 for the antigen, c) F1031-8-3 antibody, and d) F1106-13-3 antibody.

It is to be noted that WO2004/44005 also describes an antibody which binds to the peptide comprising the amino acid residues described in SEQ ID NO: 2, SEQ ID NO: 4, or SEQ ID NO: 5; and an antibody prepared by using the peptide comprising 8 to 30 consecutive amino acid residues from the amino acid sequence described in SEQ ID NO: 6 for the antigen. On the other hand, the antibody which specifically binds to the recombinant soluble CD14 fragment according to the second aspect of the present invention may include some of such antibodies. For clear distinction, such antibodies may be excluded from the antibody which specifically binds to the recombinant soluble CD14 fragment according to the second aspect of the present invention.

"The antibody which specifically binds to the recombinant soluble CD14 fragment according to the second aspect of the present invention" according to the eighth aspect of the present invention is preferably an antibody which does not substantially bind to the full length soluble CD14 protein in human blood or rsCD14(1-356), while it specifically binds to the recombinant soluble CD14 fragment according to the second aspect of the present invention. It is also preferably an antibody which is a monoclonal antibody.

The antibody of the present invention can be prepared by using the recombinant soluble CD14 fragment according to the second aspect of the present invention for the antigen.

The particularly preferred antibody is the antibody F1237-3-4. The hybridoma producing this F1237-3-4 antibody has been internationally deposited to the National Institute of Advanced Industrial Science and Technology (Independent Administrative Institute), International Patent Organism Depositary (Chuo-dairoku, 1-1, Higashi 1-chome, Tsukuba-shi, Ibaraki-ken, Japan) with the Accession No. FERM ABP-10330.

Use of the antibody according to the eighth aspect of the present invention enables assay of the soluble CD14 antigen according to the first aspect of the present invention, and constitution of the "assay kit for assaying the soluble CD14 antigen according to the first aspect of the present invention" according to the fifth aspect of the present invention.

The "assay kit for the soluble CD14 antigen according to the first aspect of the present invention" according to the fifth aspect of the present invention does not detect the high molecular weight CD14. This is the reason why an antibody which does not substantially bind to the full length soluble CD14 protein in human blood is preferred. This is also the reason why the monoclonal antibody is preferred for use in the assay kit. In addition, an antibody which does not substantially bind to the full length soluble CD14 protein in the human blood or the rsCD14(1-356) is particularly advantageous since the assay can be conducted by using the antibody alone without conducing the sandwich immunoassay using the second binding substance.

As described above, WO2004/44005 describes an antibody which binds to a peptide comprising the amino acid residues described in SEQ ID NO: 2, SEQ ID NO: 4, or SEQ ID NO: 5; an antibody prepared by using a peptide comprising 8 to 30 consecutive amino acid residues selected from the amino acid sequence described in SEQ ID NO: 6 for the antigen; and F1031-8-3 antibody and F1106-13-3 antibody which are respectively an anti-CD14 antibody. Advantage of these antibodies is that they can be used in an assay kit for assaying the low molecular weight CD14 which is effective in diagnosing the sepsis. The antibodies described in WO2004/44005, however, are not proved for their direct relationship with the soluble CD14 antigen according to the first aspect of the present invention, and the situation of the invention of WO2004/44005 is that, when the peptide or the CD14 disclosed in WO2004/44005 was used as an antigen in producing the kit, the product could be usefully incorporated in the low molecular weight CD14 assay kit for sepsis.

On the other hand, the antibody of the present invention can be used in the "an assay kit for the soluble CD14 antigen according to the first aspect of the present invention" according to the fifth aspect of the present invention. In addition, "the recombinant soluble CD14 fragment according to the second aspect of the present invention" has immunological nature similar to the soluble CD14 antigen according to the first aspect of the present invention, and the antibody can not be used in the assay kit for "the soluble CD14 antigen according to the first aspect of the present invention" if it were not an antibody which binds to this fragment (namely, if it were not the antibody of the present invention).

The only antibody that has been known and that can be used in the assay kit for "the soluble CD14 antigen according to the first aspect of the present invention" is the above-mentioned antibody described in WO2004/44005, and the only antibody that binds to "the recombinant soluble CD14 fragment according to the second aspect of the present invention" is also the above-mentioned antibody described in WO2004/44005. It has also been revealed that various anti-CD14 antibodies do not bind to "the recombinant soluble CD14 fragment according to the second aspect of the present invention".

In other words, the antibody of the present invention is an invention fully covering and disclosing the antibodies which can be used in "the assay kit for the soluble CD14 antigen according to the first aspect of the present invention". Furthermore, the antibody prepared by using "the recombinant soluble CD14 fragment according to the second aspect of the present invention" for the antigen shows a high immunological reactivity with "the soluble CD14 antigen according to the first aspect of the present invention", and therefore, such an antibody should be particularly useful.

<Ninth Aspect>

Ninth aspect of the present invention is an antibody which specifically binds to the recombinant soluble CD14 fragment according to the third aspect of the present invention.

The antibody according to the ninth aspect of the present invention can be prepared by using the recombinant soluble CD14 fragment according to the third aspect of the present invention for the antigen.

The preferable examples of the antibody according to the ninth aspect of the present invention is the same as those of the eighth aspect of the present invention. Utility and other features of the antibody is also the same.

<Tenth Aspect>

Tenth aspect of the present invention is a method for screening for an antibody which is useful in assay the soluble CD14 antigen according to the first aspect of the present invention, and this method comprises the following steps of:

1) preparing antibodies which specifically bind to a peptide comprising 6 to 20 consecutive amino acid residues selected from the amino acid sequence described in SEQ ID NO: 3;

2) preparing an analyte solution containing the CD14;

3) constituting an immunoassay system by using the antibodies prepared in 1) or the analyte solution prepared in 2);

4) assaying the substance which specifically binds to the antibodies prepared in 1) in the analyte solution by using the immunoassay system constituted in 3); and 5) evaluating and selecting the antibody useful in assay the soluble CD14 antigen according to the first aspect of the present invention based on the assay result obtained in 4).

The screening method according to the tenth aspect of the present invention is a method for screening for an antibody which is useful in assay the soluble CD14 antigen according to the first aspect of the present invention which may serve as an effective marker in diagnosing sepsis. That is, this is a method for selecting an antibody which is useful in assay the soluble CD14 antigen according to the first aspect of the present invention which may serve as an effective marker in diagnosing sepsis. This method is also a method for selecting an antibody which can be used in the kit according to the fifth aspect of the present invention.

The screening method according to the tenth aspect of the present invention is characterized in that "the antibody which specifically binds to a peptide comprising 6 to 20 consecutive amino acid residues selected from the amino acid sequence described in SEQ ID NO: 3" prepared in the step 1) is used for the screening subject. The screening subject prepared is not particularly limited as long as it is "the antibody which specifically binds to a peptide comprising 6 to 20 consecutive amino acid residues selected from the amino acid sequence described in SEQ ID NO: 3". A fragment of such an antibody may also be used for the screening subject as long as the fragment retains the capability of undergoing the antigen—antibody reaction with the antigen (The following description of the antibody also includes the description for the fragment of the antibody).

The analyte solution of the 2) is not particularly limited as long as it contains CD14. The analyte solution, however, is preferably a solution at least containing the high molecular weight CD14.

The immunoassay system constituted in the 3) is not particularly limited as long as it can determine whether the screening subject antibody is capable of specifically reacting with the CD14 in the analyte solution. Exemplary immunoassay systems include antigen immobilization, sandwich assay, or biomolecular interaction analysis. The immunoassay system, however, may apply the methods described for the fifth aspect or sixth aspect of the present invention.

The step 4) is conducted according to immunoassay system constituted in the step 3), and the substance which specifically binds to the antibody prepared in the 1) is assayed by using the analyte solution for the analyses subject.

The step 5) is a step wherein the screening subject antibody is evaluated based on the result obtained in the step 4) for its effectiveness in using in the immunoassay for diagnosing sepsis, and if evaluated to be effective, the screening subject antibody is selected for use in the immunoassay for diagnosing sepsis. The criteria are not particularly limited.

As described above, the screening method according to the sixth aspect of the present invention is characterized in that the screening subject is "the antibody which specifically binds to a peptide comprising 6 to 20 consecutive amino acid residues selected from the amino acid sequence described in SEQ ID NO: 3" prepared in the step 1), and other steps are not necessarily limited.

The antibody prepared in the step 1) is preferably the antibody which specifically binds to a peptide comprising 6 to 20 consecutive amino acid residues selected from the amino acid sequence of positions 1 to 314 from the N terminal of the amino acid sequence described in SEQ ID NO: 3; the antibody produced by using a peptide comprising 8 to 30 consecutive amino acid residues selected from the amino acid sequence described in SEQ ID NO: 3 for the antigen; or the antibody produced by using a peptide comprising 8 to 30 consecutive amino acid residues selected from the amino acid sequence of positions 1 to 314 from the N terminal of the amino acid sequence described in SEQ ID NO: 3 for the antigen.

It is to be noted that, in the step 1), antibody of the following (i) to (iv) may be prepared instead of "the antibody which specifically binds to a peptide comprising 6 to 20 consecutive amino acid residues selected from the amino acid sequence described in SEQ ID NO: 3". (i) The antibody prepared by synthesizing the peptide on the basis of the full length sequence of the CD14 by a method commonly used in the art, and by preparing an immunizing antigen to produce the antibody. (ii) The antibody prepared by purifying the purified soluble CD14 in the serum and using the purified soluble CD14 for the immunogen to produce the antibody. (iii) The antibody prepared by preparing a recombinant CD14 protein by using COS cell or *E. coli*, and using this recombinant CD14 protein for the immunogen to produce the antibody. (iv) The antibody prepared by treating a CD14 antigen by thermal denaturing or DNP-ation, and using the treated product for the immunogen to produce the antibody.

Next, an embodiment is further described in which the immunoassay system constituted in the step 3) is antigen immobilization.

In this embodiment, a labeled antibody for the antibody prepared in the step 1), for example, a labeled anti-immunoglobulin antibody is further prepared.

In the step 2), the analyte solution prepared is preferably a body fluid from a normal donor or a standard sample of human high molecular weight CD14. The standard sample of the human high molecular weight CD14 prepared may be, for example, the fraction of the body fluid from a normal donor adsorbed by 3C10 antibody affinity column.

The immunoassay system may be constituted, for example, so that a complex of "the high molecular weight CD14 in the analyte solution"—"the antibody prepared in the step 1)"—"labeled anti-immunoglobulin antibody" is formed on the insoluble carrier, and in this case, the specific binding of "the antibody prepared in the step 1)" to "the high molecular weight CD14 in the analyte solution" is assayed by means of the label. For example, the analyte solution may be bonded to an insoluble carrier in the step 3), and in the step 4), in the dot blotting assay system constituted in the step 3), the antibody prepared in 1) and the "labeled anti-immunoglobulin antibody" may be reacted in this order. The degree of the complex formation may then be evaluated by the intensity of the label, namely, by measuring the substance specifically reacted with the antibody prepared in the step 1) in the analyte solution.

In the 5), for example, the antibody prepared in the step 1) which showed week or little label intensity may be evaluated to exhibit weak or little specific binding to the high molecular weight CD14 in the body fluid of the normal donor or the human high molecular weight CD14 standard sample, and such antibody can be selected as an antibody which is effective for use in the sepsis diagnosing immunoassay. For example, when an antibody which has been evaluated to have a strong binding ability to the high molecular weight CD14 in the blood is used to measure the substance in human body fluid that specifically binds such an antibody, the main protein that is measured will be the high molecular weight CD14. In such a case, if the soluble CD14 antigen according to the first aspect of the present invention which is present at a lower content than the high molecular weight CD14 is to be measured, an antibody which does not specifically bind to the high molecular weight CD14 may be selected for use in the assay.

The assay will be an antigen immobilized EIA when an enzyme is used for the label in the antigen immobilization method, and a dot blotting method when a membrane is used for the insoluble carrier.

Next, an embodiment is described in further detail wherein the immunoassay constituted in the step 3) of the present invention is a sandwich assay.

With regard to the sandwich immunoassay, this assay may be conducted as described for the kit according to the fifth aspect of the present invention or the assay method according to the fifth aspect of the present invention.

In this case, another antibody which specifically binds to a peptide comprising 6 to 20 consecutive amino acid residues selected from the amino acid sequence described in SEQ ID NO: 3 or an anti-CD14 antibody (hereinafter sometimes referred to as the second antibody) is prepared.

The analyte solutions prepared in the step 2) are preferably a body fluid from a normal donor and a body fluid from a sepsis patient. In this case, the body fluid from the normal donor and the body fluid from the sepsis patient are preferably those collected from the same source, for example, a blood sample of the normal donor and the blood sample of the sepsis patient, or a urine sample of the normal donor and the urine sample of the sepsis patient. The sample is preferably a blood sample, and more preferably, a serum sample.

And then, the sandwich immunoassay system is constituted on the insoluble carrier, for example, to form a complex of "the antibody prepared in the step 1)"—"the soluble CD14 antigen according to the first aspect of the present invention"—"the second antibody".

For example, in the step 3), either one of "the antibody prepared in the step 1)" and "the second antibody" is bonded to the insoluble carrier, and the other one is labeled to constitute the sandwich immunoassay system.

In the step 4), the analyte solution and the labeled antibody are allowed to react with the sandwich immunoassay system constituted in the step 3).

In the step 5), the assay result for the body fluid from the normal donor and the assay result for the body fluid from the sepsis patient are compared, and an antibody which is useful in assay the soluble CD14 antigen according to the first aspect of the present invention is selected on the basis of the evaluation of the difference between the compared assay results.

When the immunoassay constituted in the step 3) is a sandwich assay, the antibody selection is preferably carried out to thereby select a combination of the antibody prepared in the step 1) and "the second antibody". More specifically, a screening is preferably carried out to select a combination of antibodies used to assay blood protein which can serve as an effective marker for sepsis diagnosis, namely, a combination of antibodies for sandwich immunoassay effective for sepsis diagnosis.

The antibodies used for the screening method of the present invention can be prepared in accordance with the description of the section of the assay kit according to the fifth aspect of the present invention. The materials used are also as described for the assay kit according to the fifth aspect of the present invention.

The biomolecular interaction analysis used is not particularly limited. Exemplary such analysis, however, is surface plasmon resonance analysis, which may be conducted, for example, by Biomolecular Interaction Analysis Systems (manufactured by Biacore).

<Eleventh Aspect>

Eleventh aspect of the present invention is a method for screening for an antibody which is useful in assay the soluble CD14 antigen according to the first aspect of the present invention, said method comprising the steps of:

1) preparing antibodies for screening;
2) preparing the recombinant soluble CD14 fragment according to the second aspect of the present invention;
3) reacting the antibodies prepared in 1) with the fragment prepared in 2) to evaluate the specific binding between the antibodies prepared in 1) and the fragment prepared in 2); and
4) selecting the antibody which underwent specific binding with the fragment prepared in 2) in step 3) as the antibody which is useful in assay the soluble CD14 antigen according to the first aspect of the present invention.

The screening method according to the eleventh aspect of the present invention is a method for screening for an antibody which is useful in assay the soluble CD14 antigen according to the first aspect of the present invention which may serve as an effective marker in diagnosing sepsis, namely, a method for selecting an antibody which is useful in assay the soluble CD14 antigen according to the first aspect of the present invention which may serve as an effective marker in diagnosing sepsis. This screening method is also a method for selecting an antibody which can be used in the kit according to the fifth aspect of the present invention.

The screening method according to the eleventh aspect of the present invention is characterized in that an evaluation is conducted by reacting the screening subject antibody with the recombinant soluble CD14 fragment according to the second aspect of the present invention to evaluate whether it undergoes a specific reaction, namely, an antigen-antibody reaction. As described in the section of the second aspect of the present invention, the recombinant soluble CD14 fragment according to the second aspect of the present invention does not undergo specific reaction with 3C10 or MEM-18 but with the antibody produced by using the peptide comprising the 16 amino acid residues described in SEQ ID NO: 2 for the antigen. This is the same immunological nature as that of the soluble CD14 antigen according to the first aspect of the present invention. Because of this immunological nature, the selection of an antibody useful in assay the soluble CD14 antigen according to the first aspect of the present invention can be accomplished by the evaluation of the reaction between the screening subject antibody and the recombinant soluble CD14 fragment according to the second aspect of the present invention.

In the step 1), the screening subject prepared is not particularly limited as long as it is an antibody. The screening subject may also be a fragment of an antibody as long as it has the function of undergoing an antigen-antibody reaction with another antigen. (The following description of the antibody also applies to a fragment of such an antibody).

In order to improve screening efficiency, the screening subject prepared is preferably "an antibody which specifically binds to a protein comprising any one of 6 to 356 consecutive amino acid residues selected from the amino acid sequence described in SEQ ID NO: 3", and more preferably, "an antibody which specifically binds to a protein comprising at least 7 consecutive amino acid residues selected from positions 53 to 68 of the amino acid sequence described in SEQ ID NO: 3".

The recombinant soluble CD14 fragment according to the second aspect of the present invention prepared in the step 2) is not particularly limited as long as it is an recombinant soluble CD14 fragment described in the section of the second aspect of the present invention.

The method used in the step 3) to react the antibody prepared in the step 1) with the fragment prepared in the step 2) to evaluate the specific binding between the antibody prepared in the step 1) and the fragment prepared in the step 2) is not particularly limited as long as it is capable of evaluating whether both reactants exhibits specific binding, namely, an antigen-antibody reaction. Exemplary methods include antigen immobilization, sandwich assay, and biomolecular interaction analysis, which are as described in the section explaining about the tenth aspect of the present invention. When the specific binding is evaluated by a sandwich immunoassay using a second antibody, evaluation of the antibody combination in the sandwich assay will be enabled.

<Twelfth Aspect>

Twelfth aspect of the present invention is a method for producing the recombinant soluble CD14 fragment according to the second aspect of the present invention, comprising the steps of:

(i) producing a recombinant soluble CD14 fragment having the sequence characterized by the following 1) to 4):

1) a fragment having a partial sequence of the amino acid sequence described in SEQ ID NO: 3, or a fragment having such partial sequence in which 1 to 10 amino acids have been deleted, added, or substituted in the region other than positions 53 to 68 of SEQ ID NO: 3;
2) the N terminal is any one of positions 1 to 17 of SEQ ID NO: 3;
3) the C terminal is any one of positions 134 to 356 in SEQ ID NO: 3;
4) a sequence of a cleavage site for a predetermined protease has been incorporated in the downstream of any one of positions 59 to 70 of SEQ ID NO: 3 by substitution or insertion;

(ii) cleaving the recombinant soluble CD14 fragment prepared in (i) with the predetermined protease; and
(iii) recovering the fragment of the N terminal side cleaved in ii);

wherein the recombinant soluble CD14 fragment produced has the sequence characterized by the following 5) to 7):

5) a fragment having a partial sequence of the amino acid sequence described in SEQ ID NO: 3, or a fragment having such partial sequence in which 1 to 10 amino acids have been deleted, added, or substituted in the region other than positions 53 to 68 of SEQ ID NO: 3;

6) the N terminal is any one of positions 1 to 17 of SEQ ID NO: 3; and 7) the C terminal is any one of positions 59 to 70 in SEQ ID NO: 3.

"The method for producing the recombinant soluble CD14 fragment according to the second aspect of the present invention" according to the twelfth aspect of the present invention is capable of producing a recombinant soluble CD14 fragment according to the second aspect of the present invention having the predetermined amino acid sequence. The detailed production method is as described in the section of the second aspect of the present invention.

For example, when the predetermined protease is PreScission Protease, the sequence of the cleavage site in the step i)4) is Leu, Glu, Val, Leu, Phe, Gln, Gly, Pro.

When the predetermined protease is thrombin, the sequence of the cleavage site in the step i)4) is Leu, Val, Pro, Arg, Gly, Ser.

EXAMPLES

Hereinafter, the present invention will be described more concretely by way of examples. However, the examples are only exemplary and the present invention should by no means be construed as being limited thereto. Further, symbols used in the following description are based on the symbols as a convention in the art.

Those manufactured by ProMedDx, Samplex and Sera Care Life Science were purchased and used as sera of normal donors and sera of patients suffering from sepsis used in the following examples.

Example 1

Preparation of Polyclonal Antibody Using Synthetic Peptide as Antigen 1-(1) Preparation of Peptide as Antigen To bind a peptide having the sequence described in SEQ ID NO: 2 (corresponding to a sequence at positions 53 to 68 described in SEQ ID NO: 3) (hereinafter, described as S68 peptide) to a carrier protein at the N-terminal thereof through an SH group, the peptide was synthesized by inserting cysteine into the N-terminal. That is, using a peptide synthesizer ABI433A (Applied), amino acid columns were aligned according to the amino acid sequence and an amino acid column for cysteine was placed on the N-terminal, followed by conducting automatic synthesis. The synthesized peptide was cut out from a resin by a conventional procedure and was then precipitated with ethyl ether, recovered, and dissolved in distilled water again, followed by freeze drying. After the resulting crude peptide had been dissolved, the peptide was eluted with a linear gradient of 5-70% acetonitrile concentration using a C18 reversed phase HPLC (CAPCELL-PAK, Shiseido Co., Ltd.), followed by collecting a fraction containing a target peptide. The collected fraction was freeze-dried and 2 to 3 mg of purified peptide was obtained.

1-(2) Preparation of Peptide Carrier Antigen Using Synthetic Peptide

A peptide prepared in 1-(1) was dissolved in distilled water to 10 mg/mL and the solution was mixed with 10 mg/mL of maleimide-activated keyhole limpet hemocyanin (Imject™ Maleimide Activated Keyhole Limpet Hemocyanin (KLH) (PIERCE)) in equivalent amounts. After the mixture had been reacted for 2 hours at room temperature, the reaction mixture was desalted by an NAP-10™ column (Amersham Biosciences) being equilibrated with physiological saline to obtain 1 mg of S68-peptide carrier antigen (hereinafter, described as S68 peptide-KLH). The concentration of proteins described in the following examples was obtained by dividing the amount of used KLH by the amount of liquid.

1-(3) Preparation of Polyclonal Antibody Using Synthetic Peptide as Antigen

For preparing a polyclonal antibody against S68 peptide-KLH prepared in 1-(2), a rabbit was immunized using S68 peptide-KLH. That is, 100 μg of each of S68 peptide-KLH was diluted with 500 μL of physiological saline and the solution was mixed with 500 μL of Freund's complete adjuvant (DIFCO) in equivalent amounts, followed by subcutaneously administering the mixture to the back of New Zealand white female rabbit (Kitayama Labes Co., Ltd.) weighing 2.1 to 2.2 kg. After 2 weeks, 100 μg of each of S68 peptide-KLH was diluted with 500 μL of physiological saline and the solution was mixed with 500 μL of Freund's incomplete adjuvant (DIFCO) in equivalent amounts, followed by subcutaneously administering the mixture to the back. After additional 2 weeks from that, 100 μg of S68 peptide-KLH was diluted with 1 mL of physiological saline and the solution was administered in an ear vein.

After 1 week from the completion of administration, blood was collected from the ear vein and antiserum was separated from the blood by routine procedures and an antibody was purified. First, ammonium sulfate was added to the antiserum up to a final saturation concentration of 33%. After the mixture had been stirred for 1 hour at 4° C., the separated precipitate was centrifuged. Then, the precipitate was dissolved in a 76-mM phosphate buffer (hereinafter, described as PBS (pH 6.4)) and the solution was dialyzed overnight. After the dialysate had been filtered, the filtrate was applied to a protein A column (ProSep-A™, Millipore). Then, a binding IgG fraction was eluted with a 0.1 M glycine hydrochloride buffer (pH 3.0) to obtain a purified antibody. After dialysis with PBS (pH 6.4), the protein concentration was calculated from the absorbance at a wavelength of 280 nm (converted level: 0.533 mg/mL). Hereinafter, the obtained antibody will be described as an S68 peptide polyclonal antibody.

1-(4) Preparation of Specific Purified Polyclonal Antibody

For purifying only an antibody against S68 peptide from the S68-peptide polyclonal antibodies, specific purification was performed by the following method. First, for binding the S68 peptide inserted with cysteine (hereinafter, described as C-S68 peptide) to a carrier through an SH group, 200 μg of C-S68 peptide was mixed per 1 mL of SufoLink Coupling Gel (PIERCE) and reacted according to the manual thereof. After the completion of the reaction, the remaining active group was blocked and then an S68 peptide-biding affinity column was prepared. Next, 7.92 mg of the purified IgG fraction described in 1-(3) was applied and then the column was washed with a phosphate buffer (pH 7.4) (Dulbecco, hereinafter, described as D-PBS (pH 7.4)), followed by eluting an anti-S68-peptide antibody with 0.1 M glycine hydrochloride buffer (pH 3.0). After the elution, pH was readjusted to neutral and then dialysis was performed with PBS, followed by calculating the protein concentration from an absorbance at 280 nm (converted level: 0.533 mg/mL). As a result, 0.52 mg of an anti-S68-peptide antibody (hereinafter, described as S68 antibody) was obtained.

Example 2

Preparation of Monoclonal Antibody Using Synthetic Peptide as Antigen

20 µg of S68 peptide-KLH prepared in Example 1-(2) was dissolved in 100 µL of physiological saline and mixed with an equivalent amount of Freund's complete adjuvant (DIFCO), followed by administering 100 µL of the mixture to each of the rear foot pads of a female Wister rat aged 8 weeks. After 2 weeks, the iliac lymph node was surgically excised and cell fusion was performed. The cell fusion was conducted according to Tamie Ando and Takeshi Chiba: "Introduction to Monoclonal Antibody Experimental Manipulation", page 83, 1991 (Kodansha Ltd.). In other words, lymphocytes were separated from the lymph node using a cell strainer (Falcon) and mixed with myeloma cells (Sp2/O-Ag14) at a ratio of 5:1, followed by cell fusion using polyethylene glycol. Fused cells were suspended in an HAT medium and hybridomas were selected, followed by screening hybridomas producing the target antibody.

The screening was performed by an ELISA method in which rsCD14(1-307)S286C was directly immobilized on a plate. That is, 50 µL of rsCD14(1-307)S286C diluted with 0.1-M phosphate buffer (pH 7.4) to 1 µg/mL was added to each well of an immunoplate (Maxisorb, NUNC) and left to stand for 1 hour at 37° C. After that, the plate was washed with ion-exchanged water 5 times and then 100 µL of PBS (pH 6.4) containing 0.1% BSA was added to each well, followed by leaving the plate standing for 1 hour at room temperature to effect blocking. Then, the culture supernatant sampled from the selected hybridomas was added to each well and allowed to react at 37° C. for 1 hour. After that, the plate was washed 3 times with physiological saline containing 0.05% Tween 20.

Subsequently, 50 µL of a solution obtained by diluting peroxidase-labeled anti-rat immunoglobulin antibody (DAKO) 1000-fold with PBS containing 10% rabbit serum was added to each well. After reaction at 37° C. for 1 hour, the plate was washed 5 times in the same manner as above and a tetramethylbenzidine solution (TMB, BioFix) was added to each well. After a reaction for 10 minutes at room temperature, the reaction was stopped with a 0.5 M sulfuric acid solution and an absorbance at 450 nm was measured using a plate spectrophotometer (NJ-2100™, Japan Intermed). As a result, a well containing hybridoma capable of producing an antibody binding to rsCD14(1-307)S286C was selected.

Next, from the selected well, cloning was performed by a limiting dilution method according to Tamie Ando and Takeshi Chiba: "Introduction to Monoclonal Antibody Experimental Manipulation", page 83, 1991 (Kodansha Ltd.). After 10 days, likewise, screening was performed using as an index the reactivity with rsCD14(1-307)S286C and 6 kinds of hybridomas were selected. The selected hybridomas were cultivated in a 10% FCS/RPMI1640 medium (Sigma) and then cultivated in Hybridoma-SFM medium (Invitrogen) to produce an antibody. The antibody was purified using a protein G column (ProSep-G™ column, Millipore). The subtype of the purified F1146-17-2 antibody was determined to be rat IgG2b·κ by using a rat isotyping kit (ZYMED).

By the way, rsCD14(1-307)S286C was prepared using the method described in Example 9 of WO 01/72993.

Example 3

Study of Assay System with Sandwich EIA Method

Using the antibodies described in Examples 1 and 2, the assay system with a sandwich EIA method was studied.

3-(1) Preparation of Recombinant Human CD14

First, for preparing a monoclonal antibody against rsCD14 (1-285) to be used as a second antibody in the sandwich ELISA method, rsCD14(1-285) as an immunogen was prepared in E. coli. In order to express rsCD14(1-285) in E. coli, an expression plasmid pTrp1659 was constructed by the following method.

First, oligomer 8, linkS (5'-agc tta gga att t-3') (SEQ ID NO: 7) and oligomer 8, linkA (5'-cta gaa att cct a-3') (SEQ ID NO: 8) were synthesized.

Those oligomers were mixed in equivalent amounts and heated at 99° C. for 1 minute, and the mixture was then annealed by gradually cooling it down to room temperature. Furthermore, 5'-terminal thereof was phosphorylated by T4 Polynucleotide Kinase to prepare a linker.

Next, sense primer A (5'-aca tct aga tga cca cgc cag aac ct-3') (SEQ ID NO: 9) and antisense primer (5'-ttt gga tcc tta cta gag atc gag cac tct-3') A (SEQ ID NO: 10) were synthesized and PCR was performed using Pyrobest™ DNA Polymerase and plasmid pM1659 described in Example 8 of WO 01/72993 as a template.

After a reaction solution had been heated for 2 minutes at 90° C., the cycle of 98° C. for 10 seconds, 55° C. for 30 seconds, and 72° C. for 1 minute was repeated 30 times.

The resulting amplified product of about 900 bp was double-digested with XbaI and BamHI to collect DNA fragments. The vector pM710 described in Example 10 of JP 06-025289 A was double-digested with HindIII and BamHI and then subjected to agarose gel electrophoresis and collected. After three-way ligation of the linker already phosphorylated, PCR-amplified DNA fragment/XbaI+BamHI digested fragment, and vector/HindIII+BamHI fragment, which were described above, the resultant was transformed into E. coli competent cells (JM109 (TOYOBO) to obtain a clone containing the target plasmid. Plasmid DNA was prepared by routine procedures.

Subsequently, JE7924 transformant strain for the production of rsCD14(1-285) was prepared using an electroporation method.

First, E. coli JE7924 (J. Bacteriol 173, p. 4799, (1991)) was restored from a glycerol stock and incubated in an LB medium at 37° C. overnight. Furthermore, the bacteria were inoculated into 50 ml of a fresh LB medium and continuously incubated until the absorbance at 600 nm reached 0.5 to 0.6, followed by directly ice-cooling a culture flask for 30 minutes. Next, E. coli cells were collected and washed twice with ice-cooled sterilized distilled water and once with an ice-cooled 10% glycerol solution, followed by being suspended in 100 µL of an ice-cooled 10% glycerol solution. The suspension was dispensed into two tubes with 50 µL aliquots and quickly frozen in liquid nitrogen to prepare competent cells (JE7924), which were saved at −80° C. until the time of use.

Next, 50 µL of JE7924 competent cells was transformed with about 30 ng of pTrp1659 by electroporation device, Gene Pulser™ of Bio-Rad Laboratories, Inc. In addition, the settings at this time were a voltage of 2.5 kV and a resistance of 200Ω, and a capacitance of 25 µF. After that, the resultant was incubated in an LB agar plate containing 50 µg/mL of ampicillin overnight to obtain a clone transformed with pTrp1659. The clone thereof was incubated at 37° C. overnight in an LB medium and was then inoculated into a fresh medium, followed by being incubated for additional 5 hours. OD at 600 nm of culture suspension reached 2 to 3,3β-indole acrylic acid (Sigma) was added in a final concentration of 100 μg/mL and the mixture was incubated at 37° C. for 4 hours, resulting in induction expression of rsCD14(1-285). Next, *E. coli* was collected and then an inclusion body was prepared using Bug Buster™ Protein Extraction Reagent (Novagen). After that, the inclusion body was dissolved in an SDS-PAGE buffer and an SDS-PAGE was carried out to identify the expression of rsCD14(1-285) by Western blotting by an anti-CD14 antibody.

Similarly, rsCD14(1-285) to be used as an immunogen was prepared by incubating a JE7924 transformant strain in 1 L of an LB medium. First, the culture solution was centrifuged. After *E. coli* cells had been collected, the bacteria cells were washed with D-PBS and 50 mL of Bug Buster™ Protein Extraction Reagent (Novagen, hereinafter described as Bug Buster™) was added to the collected bacteria cells. The bacterial cells were suspended and left standing for 30 minutes at room temperature. After lysing, the bacterial cells were subjected to a 10-minute sonication treatment (US-3, Iuchi Seieido) and centrifuged at 10000×g at 4° C. for 20 minutes to remove a supernatant. Likewise, an additional sonication treatment was performed on the cells and the resulting precipitate was suspended in 50 mL of Bug Buster™. The suspension was added with 1 mL of a 10-mg/mL lysozyme (Seikagaku Corporation), and the whole was gently stirred and left standing for 10 minutes at room temperature. Subsequently, 200 mL of 1/10 volume of high-concentration Bug Buster™ was added to the mixture and the whole was stirred, followed by being subjected to centrifugation similarly to remove a supernatant. The resulting precipitate was suspended by the addition of 200 mL of 1/10 concentration of Bug Buster™ and then the suspension was centrifuged similarly, followed by repeating such an operation several times. 100 mL of D-PBS was added in the finally obtained precipitate, resulting in an inclusion body.

For the preparation of rsCD14(1-285), the inclusion body was dissolved in a TE buffer (pH 8.0, Nippon Gene) containing 1% Triton-X100 and the solution was then subjected to freeze and thawing 3 times, followed by collecting a precipitate by centrifugation. The precipitate was dissolved in the TE buffer (pH 8.0, Nippon Gene) containing 1% Triton-X100 again, and the solution was ice-cooled and then subjected to a 12-minute ultrasonic treatment with 250 μA at intervals of 10 seconds and centrifuged, followed by collecting a precipitate. The precipitate was dissolved in a TE buffer (pH 8.0, Nippon Gene) containing 1% Triton-X100 and 0.2M NaOH, and then treated at 37° C. for 10 minutes, centrifuged, and re-dissolved three times, followed by collecting a precipitate. The resulting precipitate was dissolved in an aqueous solution containing 6 M guanidine hydrochloric acid to prepare purified rsCD14(1-285). The concentration thereof was calculated by a protein as say of Bradford using BSA as a standard.

3-(2) Preparation of Anti-CD14 Monoclonal Antibody

[1] Preparation of F1106-13-3 Antibody

Using rsCD14(1-285) derived from *E. coli* described above as an antigen to be administered, a monoclonal antibody was prepared. First, 20 μg of purified rsCD14(1-285) was mixed with Freund's complete adjuvant (DIFCO) in equivalent amounts, followed by intraperitoneally administering 200 μL of the mixture to a 6-week-old female ddy mouse. After 2 weeks, 20 μg of purified rsCD14(1-285) was mixed with Freund's incomplete adjuvant (DIFCO) in equivalent amounts, followed by intraperitoneally administering 200 μL of the mixture. 50 μL of antigen was intraperitoneally administered to the mouse 3 days before cell fusion. After 3 days, spleen was aseptically excised. Lymphocytes were isolated from the spleen and mixed with myeloma cells (P3x63-Ag. 8. U.1) in a ratio of 10:1 and fusion was performed with polyethylene glycol according to a method described on Tamie Ando and Takeshi Chiba: "Introduction to Monoclonal Antibody Experimental Manipulation", page 83, 1991 (Kodansha Ltd.). After hybridomas had been selected using an HAT medium, screening of hybridomas producing antibodies binding to rsCD14(1-285) was performed by an ELISA method.

First, rsCD14(1-285) was diluted with PBS (pH 6.4) to 0.4 μg/mL and 50 μL of the resultant solution was then added to each well of an immunoplate (Maxisorb, NUNC) and reacted at 4° C. overnight. After that, the plate was washed with ion-exchanged water 5 times and then 100 μL of PBS (pH 6.4) containing 0.5% BSA was added to each well for blocking. Then, the sampled culture supernatant was added to each well and allowed to react at 37° C. for 1 hour. After that, the plate was washed 3 times with physiological saline containing 0.05% Tween 20. Subsequently, 50 μL of a solution obtained by diluting peroxidase-labeled anti-mouse immunoglobulin antibody (DAKO) 1000-fold with PBS containing 10% rabbit serum was added to each well. After a reaction at 37° C. for 1 hour, the plate was washed 5 times in the same manner as above and a tetramethylbenzidine solution (TMB, BioFix) was added to each well. After a reaction for 10 minutes at room temperature, the reaction was stopped with a 0.5 M sulfuric acid solution and an absorbance at 450 nm was measured using a plate spectrophotometer (NJ-2100, Japan Intermed). On the basis of the result, a well containing hybridoma producing an antibody binding to rsCD14(1-285) was selected. Next, from the selected well, cloning was performed by a limiting dilution method according to Tamie Ando and Takeshi Chiba: "Introduction to Monoclonal Antibody Experimental Manipulation", page 83, 1991 (Kodansha Ltd.). After 10 days, likewise, screening was performed using the reactivity with rsCD14(1-285) as an index to select hybridomas. As a result, 12 types of hybridomas producing anti-rsCD14(1-285) monoclonal antibody were selected.

The selected hybridomas were cultivated in a 10% FCS/RPMI1640 medium (Sigma) and then cultivated in Hybridoma-SFM medium (Invitrogen) to produce an antibody. The antibody was purified using a protein A column (ProSep-A™, Millipore).

The subtype of F1106-13-3 antibody, which was an antibody having a particularly high sensitivity, was determined as IgG2b·κ using IsoStrip™ Mouse Monoclonal antibody Isotyping Kit (Roche).

[2] Preparation of F1031-8-3 Antibody

F1031-8-3 antibody was prepared using the method described in Example 7 of WO 01/22085. Briefly describing, 20 μg of CD14 protein derived from human blood was dissolved in physiological saline and the solution was mixed with Freund's complete adjuvant (DIFCO) in equivalent amounts. Then, after 1 week from each of the initial intraperitoneal administration and the second thereof 2 weeks after the initial, an increased level of antibody titer in serum was confirmed by an ELISA method on the reactivity with recombinant human CD14 protein as in the case of Example 5 of WO 01/22085. A 100-μg antigen was intraperitoneally administered to a mouse as a final administration and after 3 days the spleen was surgically excised from the mouse. Lymphocytes were isolated from the spleen and mixed with myeloma cells (P3x63-Ag. 8. U.1) in a ratio of 10:1 and cell fusion was performed with polyethylene glycol. Hybridomas were selected using an HAT medium and after one week screening of hybridomas producing antibodies was performed by the ELISA method described above. The hybridoma that had reacted with the immobilized soluble CD14 antigen was cloned by a limiting dilution method. After 10 days, similarly, screening was performed to obtain an anti-CD14 protein monoclonal antibody. F1031-8-3 antibody having the subtype of IgG2b·κ determined using IsoStrip Mouse Monoclonal antibody Isotyping Kit (Roche) was obtained as a typical antibody.

3-(3) Study of Sandwich EIA System

For preparing a system capable of specifically detecting a protein that is present in a large amount in a patient suffering from sepsis, a sandwich EIA system was prepared using the antibodies described in Examples 1, 2, and 3-(2).

[1] Preparation of Peroxidase-Labeled Antibody

A peroxidase-labeled antibody was prepared according to the method of Nakane et al. (J. Histochem. Cytochem., vol. 22, p. 1084, 1974). That is, 4 mg of peroxidase (Toyobo) was dissolved in distilled water and the solution was then reacted at 25° C. for 20 minutes by the addition of 100 mM of periodic acid. After the completion of the reaction, 1.5% ethylene glycol was added to the reaction product and the whole was reacted at 25° C. for 10 minutes, followed by dialyzing against a 1-mM acetate buffer (pH 4.4). Each of the purified F1031-8-3 antibody and F1106-13-3 antibody was dialyzed against a 10-mM bicarbonate buffer (pH 9.5), and then 4 mg of peroxidase activated by the addition of 70 µL of a 0.2-M bicarbonate buffer (pH 9.5) per 4 mg was mixed with the antibody in equivalent amounts to allow a reaction at 25° C. for 2 hours. Next, 4 mg/mL of sodium borohydride was added and then the reaction was continued for additional 2 hours at 4° C. The reaction solution was dialyzed against PBS, resulting in a peroxidase-labeled F1031-8-3 antibody (hereinafter, it may be described as F1031-8-3-HRP) and peroxidase-labeled F1106-13-3 antibody (hereinafter, it may be described as F1106-13-3-HRP). The concentration of antibody was calculated from the amount of antibody used and the volume of the labeled antibody solution.

[2] Preparation of Sandwich EIA System

Prepared was a 2-step sandwich EIA system using the S68 antibody prepared as an immobilized antibody in Example 1 and antibodies prepared in Example 3-(2)[1] and [2] as labeled antibodies. That is, S68 antibody was diluted with D-PBS (pH 7.4) to 10 µg/mL and 50 µL of the resultant solution was then added to each well of an immunoplate (Maxisorb™, NUNC) and reacted at 4° C. overnight. After that, the plate was washed with ion-exchanged water 5 times and then 100 µL of D-PBS containing 0.1% StabilGuard™ (SurModics, Inc) and 0.1% Tween 20 was added to each well to effect blocking. Using as a diluent PBS (pH 7.4) containing 1% normal donor serum (serum from which soluble CD14 antigen was removed using 3C10, hereinafter, described as CD14-absorbing serum; 3C10 was prepared from ATCC228-TIB hybridoma obtained from American Type Culture Collection) and by using PBS (pH 7.4) containing 0.1% BSA as a diluting solution, diluted specimens of human sera of normal donors and human sera of patients suffering from sepsis were prepared by diluting the sera 20-fold, respectively. A diluted specimen was added in a concentration of 50 µL per well and reacted at 37° C. for 2 hours.

After the completion of the reaction, the specimen was washed three times with physiological saline containing 0.05% Tween 20 and 50 µL of F1031-8-3-HRP or F1106-13-3-HRP diluted to 0.6 µg/mL with 76 mM PBS (pH 8.0) containing 5% rat serum, 1% mouse serum and 0.1% Tween 20 was added to each well. After a reaction at 37° C. for 2 hours, the plate was washed 5 times in the same manner as above and a tetramethylbenzidine solution (TMB, BioFix) was added to each well. After a reaction for 20 minutes at room temperature, the reaction was stopped with a 0.5 M sulfuric acid solution and an absorbance at 450 nm was measured using a plate spectrophotometer (NJ-2100, Japan Intermed). As a result, as shown in Table 1, a soluble protein in blood, which could not increase in a normal donor but increase in a patient suffering from sepsis in the system in which antibody derived from S68 peptide was used, was able to be assayed.

[3] Preparation of Sandwich EIA System <2>

Prepared was a 2-step sandwich EIA system using the F1146-17-2 antibody prepared as an immobilized antibody in Example 2 and antibody prepared in Example 3-(2)[2] as a labeled antibody. F1146-17-2 antibody was diluted with PBS (pH 6.4) to 120 µg/mL and 50 µL of the resultant solution was then added to each well of an immunoplate (Maxisorb™, NUNC) and reacted at 56° C. for 30 minutes. After that, the plate was washed with ion-exchanged water 5 times and then 100 µL of PBS containing 0.1% StabilGuard™ (SurModics, Inc) and 0.1% Tween 20 (Wako Pure Chemical Industries, Ltd.) was added to each well to effect blocking. Using as a diluent PBS (pH 6.4) containing 1% BSA, diluted specimens of human sera of normal donors and human sera of patients suffering from sepsis were prepared by diluting the sera 10-fold, respectively. A diluted specimen was added in a concentration of 50 µL per well and reacted at 25° C. for 2 hours.

After the completion of the reaction, the plate was washed three times with physiological saline containing 0.05% Tween 20 and 50 µL of peroxidase-labeled F1031-8-3 antibody diluted to 0.5 µg/mL by 76 mM phosphate buffer (pH 8.0) containing 5% rat serum, 1% mouse serum, and 0.1% Tween 20 was added to each well. After a reaction at 25° C. for 2 hours, the plate was washed 5 times in the same manner as above and a tetramethylbenzidine solution (TMB, BioFix) was added to each well. After a reaction for 20 minutes at room temperature, the reaction was stopped with a 0.5 M sulfuric acid solution and an absorbance at 450 nm was measured using a plate spectrophotometer (NJ-2100, Japan Intermed). As a result, similarly to the S68 antibody, in the case of S68-peptide specific monoclonal antibody as shown in Table 1, which was almost not found in the sera of normal donors but found in a high level in the sera of patients suffering from sepsis, was able to be assayed. That is, the result confirmed that an antibody that binds to S68 peptide can prepare a sandwich system irrespective of whether the antibody is polyclonal or monoclonal.

In Table 1, "++" represents a 4-fold or more absorbance at 450 nm compared with the absorbance of the diluent itself and "+" represents a 2-fold or more absorbance, and "−" represents an absorbance equal to the absorbance of the diluent.

TABLE 1

| Combination of antibodies | | Measured level | |
| --- | --- | --- | --- |
| Immobilizing side | Labeling side | Patient suffering from sepsis | Normal donor |
| S68 antibody | F1031-8-3 antibody | ++ | − |
| S68 antibody | F1106-13-3 antibody | ++ | − |
| F1146-17-2 antibody | F1031-8-3 antibody | + | − |

Example 4

Specificity of S68 Antibody

For confirming the specificity of S68 antibody prepared in Example 1, the inventors studied whether blocking occurs by a peptide by the same assay as that of Example 3-(3). That is, S68 peptide (amino acid sequence at positions 53 to 68), synthetic polypeptide prepared by the same way as that of Example 1 (amino acid sequence at positions 53 to 58, amino acid sequence at positions 57 to 62, and amino acid sequence at positions 59 to 64), or negative control peptide (Cys Glu Gly Asn Gly Asn Asn Phe Glu Ser Arg Glu Ala Cys) (SEQ ID NO: 29) was diluted to 0, 0.1, 1, and 10 μg/mL and 25 μL of each diluted solution was added to 25 μL of each of 50-fold diluted solutions of the sera obtained from patients suffering from sepsis and the sera of normal donors to initiate a competitive reaction by mixing with S68 antibody. After that, the levels of the soluble protein bound to S68 antibody without inhibition by any peptide were determined.

Figure 1B:
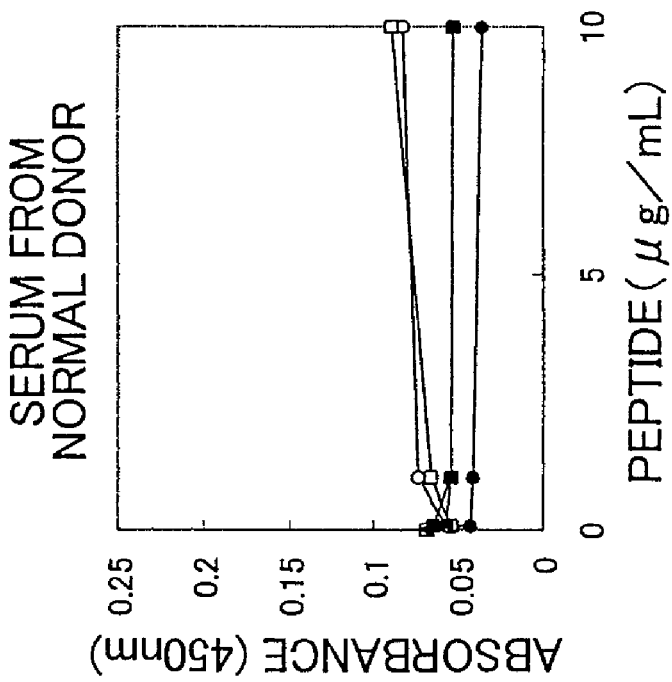

As a result, as shown in FIG. 1, in both the sera of the normal donors showing low levels and of patients suffering form sepsis showing high levels, the binding between S68 antibody and the soluble protein in serum was inhibited in the case of S68 peptide but not inhibited in the case of other partial peptides (each containing 6 amino acids) and a negative control peptide. The above result confirmed that a protein being detected in blood by S68 antibody is specifically recognized by S68 antibody. In addition, the result also confirmed that the sequence recognized by the antibody requires a length of at least 7 amino acids because the inhibition can not be attained by three kinds of synthetic peptides (the number of amino acids: 6) corresponding to the partial peptides of S68 peptide.

Example 5

Reaction Rate Constant of Prepared Antibody

The specificities and reaction rate constants of S68 antibody prepared in Example 1 and F1146-17-2 antibody prepared in Example 2 were analyzed using Biacore™ 3000 (Biacore), respectively. First, S68 peptide-BSA to be immobilized was prepared by the same way as one described in Example 1 using maleimidated BSA (Imject™ Maleimed Activated BSA, PIERCE). Next, the S68 peptide-BSA was immobilized on a sensor chip CM5 (Biacore) using an amine-coupling kit (Biacore). An assay was performed such that HBS-EP (Biacore) was used as a running buffer and a dilution series (50, 100, 150, 200, and 300 nM) of F1146-17-2 antibody was injected into flow cells. The data analysis was performed using Biaevaluation™ software version 3.0 (Biacore) by subtracting reference-cell data from flow-cell measurement data of S68 peptide-BSA. As a result of analyzing a dissociation constant (KD), the F1146-17-2 antibody showed affinity as high as $4.8 \times 10^{-9}$ M. By the way, the KD value of specifically-purified rabbit S68 peptide polyclonal antibody measured similarly was $2.2 \times 10^{-10}$ M.

Example 6

Specificity of Anti-CD14 Monoclonal Antibody 6-(1) Analysis of F1106-13-3 Antibody For clarifying a binding region (epitope) of F1106-13-3 antibody, a peptide library membrane (Custom SPOTs™, Sigma Genosys) on which the amino acid sequence of CD14 was synthesized from the N-terminal thereof 10 amino acids at a time was used for analysis. That is, the membrane was blocked based on the instruction manual thereof and then was reacted with F1106-13-3 antibody, washed, and then reacted with β-galactosidase-labeled anti-mouse antibody. After the membrane had been washed, a peptide sequence on which the antibody was bound was detected using X-gal. By the way, the peptide sequences on the peptide library membrane were analyzed using 19 peptides which were synthesized such that 10 amino acids were subjected to the synthesis at a time so as to overlap two amino acids of the respective C terminals of the sequences of amino acids at positions 1 to 154. The peptides were prepared by the same way as that of Example 1-(1).

The result found that F1106-13-3 antibody binds to the region corresponding to an amino acid sequence at positions 17 to 26 of SEQ ID NO: 3 (CNFSEPQPDW) from the N-terminal of high molecular weight CD14 (SEQ ID NO:33).

6-(2) Analysis of F1031-8-3 Antibody <1>

For confirming the specificity of F1031-8-3 antibody, the binding activity was determined using rsCD14(1-285) derived from *E. coli* described in Example 3-(1) and rsCD14 (1-356) and rsCD14(1-307)S286C prepared from COS cells using methods described in Examples 8 and 9 of WO 01/72993.

First, rsCD14(1-356), rsCD14(1-307)S286C, rsCD14(1-285), or BSA was immobilized 250 ng/spot on a membrane, Hybond-C extra (Amersham Biosciences), and after drying it was blocked by 0.05% Tween 20 containing 0.05 g/mL of skim milk (Meiji Dairies Corporation), PBS (pH 6.4). After the resultant had been left to stand for 1 hour at room temperature, F1031-8-3 antibody diluted to 3 μg/mL with 0.05% Tween 20 containing 0.5% BSA, PBS (pH 6.4) was added and reacted for 1 hour at room temperature, followed by washing with 0.05% Tween 20, PBS (pH 6.4).

Next, peroxidase-labeled anti-mouse immunoglobulin antibody (DAKO) diluted 500 folds with 0.05% Tween 20 containing 10% rabbit serum, PBS (pH 6.4) was added and reacted for 30 minutes at 37° C. Then, the membrane was washed similarly, followed by confirming the binding activity of the antibody with ECL kit (Amersham Biosciences). As a result, as shown in Table 2, F1031-8-3 antibody bound to rsCD14(1-285) derived from *E. coli*, rsCD14(1-307)S286C, and rsCD14(1-356) not to BSA. Thus, the result found that the F1031-8-3 antibody specifically recognized all types of CD14 proteins. In Table 2, "+" represents a situation in which a spot was detected on a film by the ECL and "−" represents a situation in which no spot was detected.

TABLE 2

|  | rsCD14 (1-356) | rsCD14 (1-307) S286C | rsCD14 (1-285) | BSA |
|---|---|---|---|---|
| Binding activity | + | + | + | − |

6-(3) Analysis of F1031-8-3 Antibody <2>

A binding region (epitope) of F1031-8-3 antibody was analyzed. In other words, in the sandwich EIA system of Example 3-(3)[2] where S68 antibody was used as immobilized one and F1031-8-3-HRP was used as labeled one, an inhibition test was performed using F1106-1-3 antibody.

First, as in the case of Example 3-(3)[2], 100 ng/mL of the standard preparation was added to and reacted with an S68-antibody-immobilized plate. After the plate had been washed, before the addition of F1031-8-3-HRP, a 25-μL buffer containing 6 μg/mL of F1106-1-3 antibody, mouse IgG antibody, or no antibody was added. Then, 25 μL of F1031-8-3-HRP antibody was added, followed by the measurement by the same way as that of Example 3-(3)[2].

As shown in Table 3, no inhibition occurred in the mouse IgG antibody addition system while the inhibition of binding between F1031-8-3 and standard preparation by F1106-13-3 antibody occurred. This fact indicated that F1106-13-3 antibody may bind to at least one region to be recognized by F1031-8-3 antibody. By the way, an "inhibition rate" in Table 3 was calculated from each absorbance being decreased at the time of defining the absorbance of the buffer alone as 100%.

TABLE 3

| Additive | Inhibition rate (%) |
| --- | --- |
| Mouse IgG antibody | 2 |
| F1106-13-3 antibody | 70 |

Example 7

Assay Kit for Soluble Protein 7-(1) Typical Format of Assay Kit for Sandwich EIA System A typical format of a soluble protein kit using a combination of immobilized and labeled antibodies that show high levels of the soluble protein in the specimen from patients suffering from sepsis and low levels in specimen from normal donors in Example 3-(3) will be described below.
<1> Immobilized antibody: Plate on which S68 antibody is immobilized
<2> Labeled antibody: Peroxidase-labeled F1031-8-3 antibody
<3> Substrate solution (tetramethylbenzidine solution)
Other Accessories
Format Example of a Plate System
<4> Plate-washing solution (0.9% NaCl, 0.05% Tween 20 solution)
<5> Sample-diluting solution (0.1%-BSA-containing PBS solution)
<6> Stopping reagent (0.5 M $H_2SO_4$ solution)
<7> Standard preparation (CD14(1-307)S286C)
Measuring instruments for performing an assay using the above assay kit <reference example>
<8> Plate spectrophotometer (e.g., E-Max™ (Molecular Devices Corporation))
7-(2) to (11) Format Examples of Assay Kit for Sandwich EIA System In addition to 7-(1), the examples of the assay kit for a sandwich EIA system are shown in Table 4. <1> represents a binding substance immobilized on a plate. <2> represents a labeled binding substance. The constituent elements of <3> to <7> and a measuring instrument <8> as a reference example are identical with 7-(1). <9> represents an antibody bound with a second specific binding substance. "–" represents no description.

TABLE 4

| | <1> | <2> | <9> |
| --- | --- | --- | --- |
| (2) | F1146-17-2 antibody | F1031-8-3-HRP | — |
| (3) | S68 antibody | F1106-13-3-HRP | — |
| (4) | F1146-17-2 antibody | F1106-13-3-HRP | — |
| (5) | F1031-8-3 antibody | S68 antibody-HRP | — |

TABLE 4-continued

| | <1> | <2> | <9> |
| --- | --- | --- | --- |
| (6) | F1031-8-3 antibody | F1146-17-2-HRP | — |
| (7) | F1106-13-3 antibody | S68 antibody-HRP | — |
| (8) | F1106-13-3 antibody | F1146-17-2-HRP | — |
| (9) | F1031-8-3 antibody | SA-HRP | Bio-S68 antibody |
| (10) | Str | F1031-8-3-HRP | Bio-S68 antibody |
| (11) | S68 antibody | SA-HRP | Bio-F1031-8-3 |

7-(12) Standard Curve of Assay Kit for Sandwich EIA System

Figure 2:
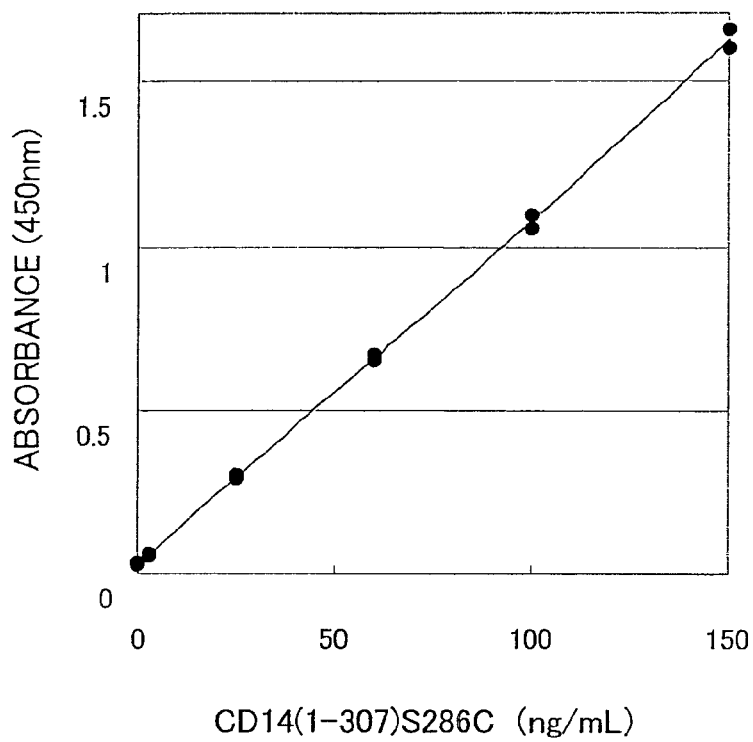
FIG. 2 shows the standard curve of the EIA kit of Example 7-(1) using sCD14(1-307)S286C protein.

Using the assay kit of (1), an assay was performed by the same way as that of Example 3-(3)[2]. That is, S68 antibody was diluted to 10 μg/mL with D-PBS (pH 7.4) and 50 μL of the resultant solution was then added to each well of an immunoplate (Maxisorb™, NUNC). After a reaction at 4° C. overnight, the plate was washed five times with ion-exchanged water and blocked by the addition of 100 μL of D-PBS containing 0.1% StabilGuard™ (SurModics, Inc.) and 0.1% Tween 20 to each well. Next, 76 mM PBS (pH 7.4) containing 1% CD14-absorbing serum and 0.1% BSA was used as a diluent to prepare a dilution series of 0, 3, 25, 60, 100, and 150 ng/mL of CD14(1-307)S286C protein standard preparation. The dilution series of the standard preparation was added in an amount of 50 μL per well and reacted for 2 hours at 37° C. After the completion of the reaction, the plate was washed three times with physiological saline containing 0.05% Tween 20. Then, 50 μL of diluted labeled antibodies prepared by diluting 5% rat serum, 1% mouse serum, and peroxidase-labeled F1031-8-3 antibody to 0.6 μg/mL with 76 mM PBS (pH 8.0) containing 0.1% Tween 20 were added to each well. After a reaction at 37° C. for 2 hours, the plate was washed five times in the same way as above and a tetramethylbenzidine solution (TMB, BioFix) was added to each well. After a reaction for 20 minutes at room temperature, the reaction was terminated by a 0.5 M sulfuric acid solution and an absorbance at 450 nm was measured using a plate spectrophotometer (NJ-2100, Japan Intermed). A standard curve prepared was shown in FIG. 2. A simple assay system with high sensitivity as a measuring sensitivity of 0.6 ng/mL (blank+3SD) was realized.

7-(13) Specificity of Sandwich EIA System

Figure 3:
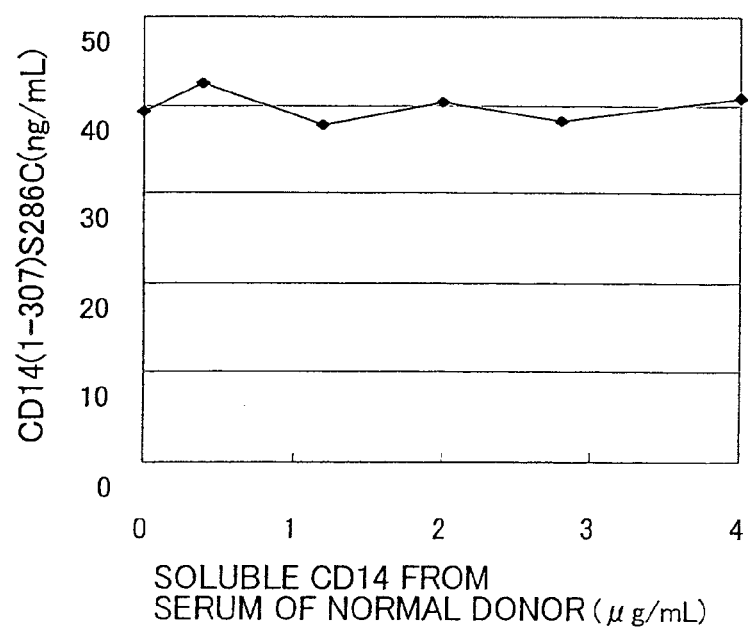
FIG. 3 shows that soluble CD14 antigen from the serum of a normal donor does not affect the measurement of the EIA kit of Example 7-(1) by using sCD14(1-307)S286C protein.

For studying the influence of high molecular weight CD14 present in human serum on the assay system prepared, soluble CD14 derived from normal donor serum at a concentration of 0 to 4 μg/mL was added to the standard preparation of CD14 (1-307)S286C to conduct the same assay as that of (12). As a result, as shown in FIG. 3, there was no influence on the measured level even though the concentration of the soluble CD14 antigen derived from normal donor serum was 4 μg/mL. The result found that the cross-reactivity of the present sandwich EIA system with high molecular weight CD14 was 0.3% or less. In other words, the result confirmed that the present system does not detect human serum high molecular weight CD14 and is specific to a soluble protein showing a high level in serum of a patient suffering from sepsis.

7-(14) Evaluation on Assay Kit for Sandwich EIA System

Reproducibility of the assay results of the kit of (1) was evaluated. The coefficient of variation (CV) of within-run reproducibility using 3 kinds of specimens as in the case of (12) was 5.8, 3.6, and 3.5% and reproducibility between measurements was 6.2, 5.2, and 5.1%, respectively. Thus good results were obtained. Further, the recovery rate in the addition/recovery test was 88 to 109%, which was satisfactory. No influence of an anticoagulant (heparin, citric acid, or EDTA) was observed. The results described above showed that the present kit has a sufficient ability for the assay of the soluble protein in blood.

Example 8

Identification of Soluble Protein in Blood 8-(1) Gel Filtration Chromatography <1>

For analyzing the substance in serum of a patient suffering from sepsis as detected by the assay kit described in Example 7-(1), the serum of the patient suffering from sepsis was fractionated through a gel filtration chromatography column Superdex™ 200PC 3.2/30 (Amersham Biosciences) with SMART SYSTEM™ (Amersham Biosciences) using D-PBS as a elution buffer. Then, each fraction was assayed using the assay kit described in Example 7-(1) and the commercially available CD14-EIA kit (IBL-Hamburg). The molecular weight thereof was calculated by calibrating the column using aldolase (158 kDa), BSA (67 kDa), ovalbumin (43 kDa), and chymotrypsin (25 kDa) from the LMW calibration kit and HMW calibration kit (Amersham Biosciences).

Figure 4:
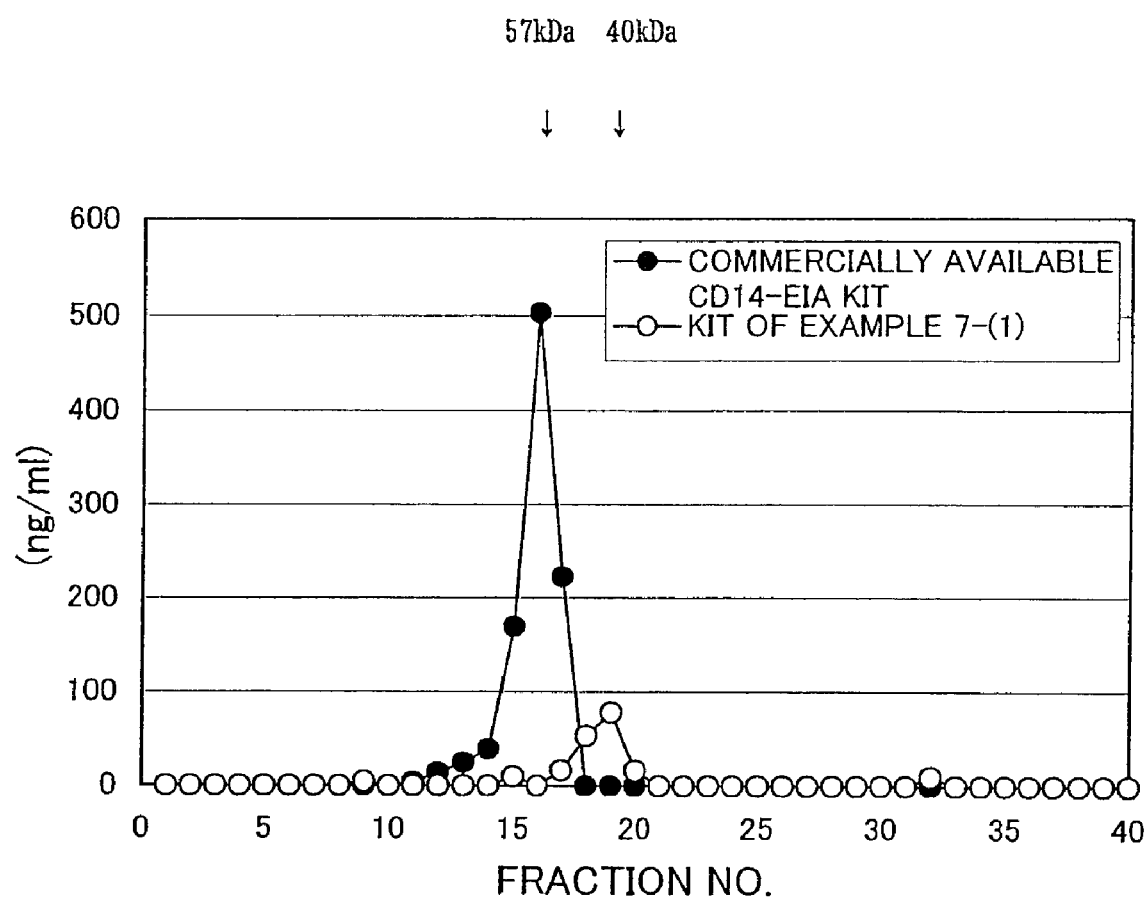
FIG. 4 shows the results of the analysis for the soluble CD14 antigen and the high molecular weight CD14 protein which may be detected from the blood of a sepsis patient by the EIA kit of Example 7-(1). The blood of a sepsis patient is fractionated by gel filtration chromatography, and analyzed by the EIA kit of Example 7-(1) and a commercially available CD14-EIA kit (IBL-Hamburg).

As a result, as shown in FIG. 4, the commercially available CD14-EIA kit detected soluble CD14 antigen having a molecular weight of about 57 kDa, which was defined as high molecular weight soluble CD14 antigen of 49 to 55 kDa conventionally reported. On the other hand, in the kit described in Example 7-(1), a peak was detected around a molecular weight of 35 to 45 kDa but no peak was detected around 57 kDa. Thus, the result confirmed that the kit described in Example 7-(1) specifically detects only a soluble protein present in blood.

8-(2) Gel Filtration Chromatography <2>

As in the case of (2)-<1>, 50 µl of serum from a patient suffering from sepsis was fractionated through a gel filtration chromatography column Superdex™ 75 10/300 GL (Amersham Biosciences) using 200 mM ammonium acetate (pH 6.8) as a elution buffer and was subjected to the assay using each kit. The molecular weight thereof was calculated by calibrating the column using BSA (67 kDa), ovalbumin (43 kDa), chymotrypsinogen (25 kDa), and ribonuclease A (13.7 kDa) from the LMW calibration kit and HMW calibration kit (Amersham Biosciences).

Figure 5:
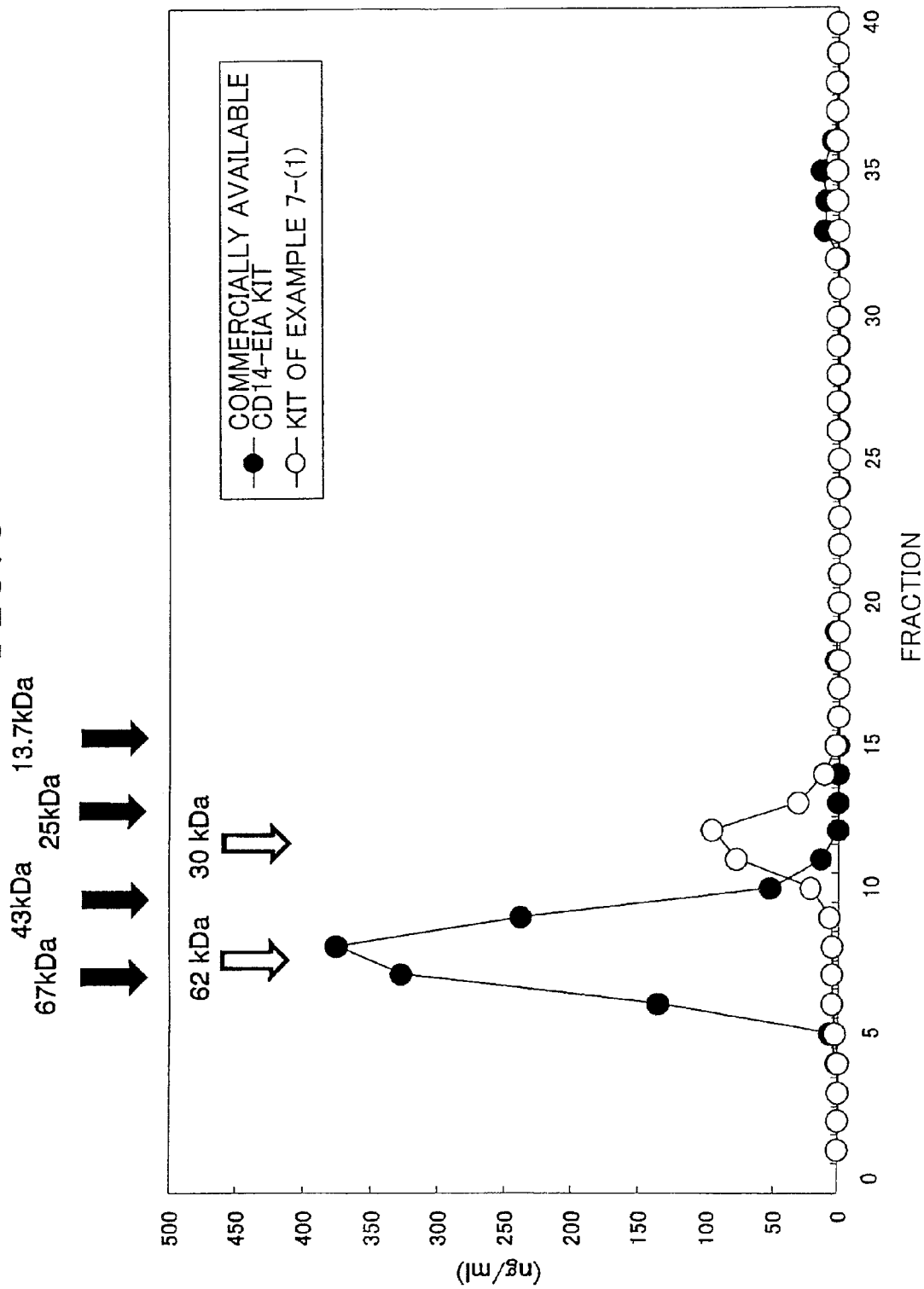
FIG. 5 shows the result of the analysis of the soluble CD14 antigen and the high molecular weight CD14 protein which may be detected from the blood of a sepsis patient by the EIA kit of Example 7-(1). The blood of a sepsis patient is fractionated by gel filtration chromatography, and analyzed by the EIA kit of Example 7-(1) and a commercially available CD14-EIA kit (IBL-Hamburg). The solid arrows on the top of the graph indicate positions of the markers used for calibration which are, from left, BSA, ovalbumin, chymotrypsinogen A, and ribonuclease A.

The results are shown in FIG. 5. In the kit described in Example 7-(1), a peak derived from the soluble protein was detected around a molecular weight of 25 to 35 kDa.

8-(3) F1025-3-1 Antibody Affinity Column Chromatography

When a peaked fraction (e.g., fraction 12) derived from the soluble protein obtained in (2)-<2> is applied to F1025-3-1 antibody affinity column chromatography, a peak derived from the soluble protein is eluted in an affinity column non-absorbing fraction. By the way, the adjustment and operation of the F1025-3-1 antibody affinity column can be performed on the basis of the method described in Example 10 of WO 01/22085.

Example 9

Purification of Soluble Protein in Blood from Serum of Patient Suffering from Sepsis 9-(1) Preparation of F1024-1-3-Sepharose 4B Carrier A 55-mg aliquot of the F1024-1-3 antibody prepared (the hybridoma cell line deposited under Accession Number FER-MBP-7511, as described above), which was described in Example 2 of WO01/72993, was added to 20 ml of ECH-Sepharose 4B (Amersham Biosciences) and then water-soluble carbodiimide (Dojindo Laboratories, Co., Ltd.) was added in a final concentration of 0.1 M to carry out a coupling reaction at 4° C. overnight. Subsequently, the reaction mixture was washed with 0.1 M sodium acetate (pH 5.0), followed by collecting unreacted F1024-1-3 antibody. Absorbances of both the antibody solution before the coupling reaction and the washing solution were measured at 280 nm, respectively, to determine a coupling efficiency (converted level: 0.714 mg/mL). As a result, it was revealed that the F1024-1-3 antibody had a coupling efficiency of 55% and 1.5 mg of the F1024-1-3 antibody could bind to 1 ml of the carrier.

Next, 1 M ethanolamine (pH 7.4) was added to the mixture to carry out a blocking reaction at room temperature for one hour, and the carrier was then washed with 100 ml of 0.1 M sodium acetate/0.5 M NaCl (pH 4.0) and subsequently with 100 ml of 0.1 M Tris-HCl/0.5 M NaCl (pH 8.0). This procedure was further repeated two times to prepare 20 ml of F1024-1-3 Sepharose 4B carrier.

9-(2) Preparation of S68-Sepharose 4 FF Carrier

A 18-mg aliquot of the S68 antibody prepared in Example 1-(4) was dialyzed at 4° C. overnight using a dialysis membrane (Spectrum, Co., Ltd.) having a molecular weight cut-off of 10 kDa and 2.5 L of a dialysate (i.e., 0.2 M $NaHCO_3$ (pH 8.3) containing 0.5 M NaCl). Furthermore, the dialysate was replaced with new one three times. Subsequently, 8 ml of NHS-Activated Sepharose 4 Fast Flow column (Amersham Biosciences) previously equilibrated with 0.2 M $NaHCO_3$ (pH 8.3) containing 0.5 M NaCl was added to the dialyzed S68 antibody solution to carry out a coupling reaction at 4° C. overnight. After the termination of the coupling reaction, unreacted S68 antibody was washed with 0.2 M $NaHCO_3$ (pH 8.3) containing 0.5 M NaCl and then collected. Absorbances of the antibody solution before and after the coupling reaction were measured at 280 nm, respectively, to determine a coupling efficiency (converted level: 0.714 mg/mL). As a result, it was revealed that the S68 antibody had a coupling efficiency of 79% and 1.8 ml of the S68 antibody could bind to 1 ml of the carrier. Next, 0.5 M monomethanolamine (pH8.3) containing 0.5 M NaCl was added to the carrier to carry out a blocking reaction at 4° C. overnight. After the termination of the blocking reaction, the carrier was washed with 300 ml of 0.1 M sodium acetate (pH 4.0) containing 0.5 M NaCl and subsequently with 300 ml of 0.2 M $NaHCO_3$ (pH 8.3) containing 0.5 M NaCl. This procedure was further repeated two times to prepare 8 ml of the S68-Sepharose 4 Fast Flow carrier.

9-(3) SDS-PAGE

SDS-PAGE was carried out using a 12.5% SDS-PAGE gel under non-reducing conditions, according to the procedures of Laemmli (Laemmli UK., Cleavage of structural proteins during the assembly of the head of bacteriophage T4. Nature, Aug. 15, 1970; 227 (259): 680-5). That is, one volume of Tris-SDS-Seprasol (Daiichi Pure Chemicals Co., Ltd.) was added to two volumes of the sample and the mixture was then heated at 100° C. for 5 minutes, followed by applying the mixture to 12.5% of ePAGEL™ gel (ATTO Corporation) to carry out electrophoresis using the Laemmli's discontinuous buffer system at 25 mA for 90 minutes. After the termination of the electrophoresis, the gel was stained with a silver-staining kit, 2D Silver Stain II "Daiichi" (Daiichi Pure Chemicals Co., Ltd.). For molecular weight determination, a molecular weight marker used was "Precision Plus Protein"™ Dual Color Standards (Bio-Rad Laboratories, Inc.).

9-(4) Western Blotting

Filter paper previously cut to fit the size of the SDS-PAGE gel was soaked in a 5% methanol/25 mM Tris/40 mM ε-aminocaproic acid solution and then placed on a cathode plate of a platinum electrode semidry transfer system BE330 (Biocraft Ltd.). Next, according to the above (3), after carrying out SDS-PAGE, the gel was soaked in the same solution and then laid on the filter paper without causing air bubbles therein. Subsequently, a nitrocellulose membrane (Trans-Blot™ Transfer-Medium, Bio-Rad Laboratories, Inc.), previously equilibrated in 5% methanol/25 mM Tris, was laid on the gel without causing air bubbles therein. Furthermore, filter paper previously soaked in the same solution was also laid thereon without causing air bubbles therein and finally the filter paper soaked in 5% methanol/300 mM Tris was laid thereon without causing air bubbles. Furthermore, an anodic electrode was placed thereon to carry out transfer at 2 mA/cm$^2$ at room temperature for two hours. After the termination of the transfer, the nitrocellulose membrane was soaked in Block-Ace™ (Dainippon Pharmaceutical Co., Ltd.) to carry out a blocking operation at 37° C. for one hour. After that, the nitrocellulose membrane was allowed to react with 10 ml of 6.8 µg/ml of F1031-8-3 antibody at 37° C. for two hours and then washed with 0.05% Tween 20/PBS, followed by reacting with an anti-mouse IgG antibody-HRP conjugate (DAKO A/S) at 37° C. for one hour. After the termination of the reaction, the nitrocellulose membrane was washed with 0.05% Tween 20/PBS. After washing out unreacted conjugates, the membrane was then soaked in 50 ml of TMB-H (Moss., Inc.) which was diluted two times with distilled water to cause luminescence at 4° C. overnight in dark.

9-(5) Purification of Soluble Protein in Blood from Serum of Patient Suffering from Sepsis A 1-ml aliquot of the F1024-1-3-Sepharose 4 FF prepared in Example 9-(1) was stuffed in Econo-Column™ (Bio-Rad Laboratories, Inc.) of 1 cm in inner diameter and then equilibrated with D-PBS (pH 7.4) containing 0.05% Tween 20. Simultaneously, 1 ml of the S68-Sepharose 4FF prepared in Example 9-(2) was stuffed in Econo-Column™ of 1 cm in inner diameter and then equilibrated with D-PBS (pH 7.4) containing 0.05% Tween 20. Subsequently, these two columns were connected in tandem such that the F1024-1-3-Sepharose™ 4B column was arranged on the tip of the S68-Sepharose™ 4FF column. Then, 18 ml of the serum from a patient suffering from sepsis was supplied into the tandem column assembly at a flow rate of 0.02 ml/min. Protein which could not be adsorbed onto the column was washed out with D-PBS (pH 7.4) containing 0.05% Tween 20. After that, the S68-Sepharose 4FF column was detached from the assembly and protein adsorbed onto the S68-Sepharose 4FF column was eluted at a flow rate of 0.2 ml/min. with 10 mM HCl containing 0.05% Tween 20, during which 2-ml aliquots were collected in 10 vessels, sequentially. To each of the fraction vessels was previously added 200 µl of 500-mM ammonium bicarbonate, so that the pH of the eluate could be immediately returned to neutral. The concentration of the soluble protein in blood in each fraction to be detected by the kit of Example 7-(1) was determined and the fraction containing the protein was then freeze-dried after pooling.

Following the freeze-drying, the freeze-dried powder was then dissolved by addition of 0.2 ml of a 150-mM ammonium acetate solution containing 0.05% Tween 20, followed by centrifugation at 3,500×g for 10 minutes. The supernatant was subjected to a gel filtration using Superdex™ 75 10/300GL (Amersham Biosciences). An elution buffer used was a 150-mM ammonium acetate solution containing 0.05% Tween 20 and then added to the column provided with 0.2 ml of the sample at a flow rate of 0.8 ml/min. From 7 or 8 minutes after the sample addition, 0.45-ml aliquots of the eluate were collected into 40 vessels, successively.

Each fraction was subjected to the measurement with the kit of Example 7-(1) and a commercially-available CD14-EIA kit (IBL-Hamburg). As a result, the soluble protein in blood which could be detected by the kit of Example 7-(1) was found in Fractions 11-13 with a peak in Fraction 12, and 1.1 µg of soluble protein in blood was obtained from 18 ml of the serum of the patient suffering from sepsis. In addition, the peak of the protein was located at the position of 29±5 kDa. Molecular weight markers used were BSA (67.0 kDa), Ovalbumin (43.0 kDa), Chymotrypsinogen A (25.0 kDa), and Ribonuclease A (13.7 kDa) in Gel Filtration LMW Calibration Kit (Amersham Biosciences), respectively.

Figure 6:
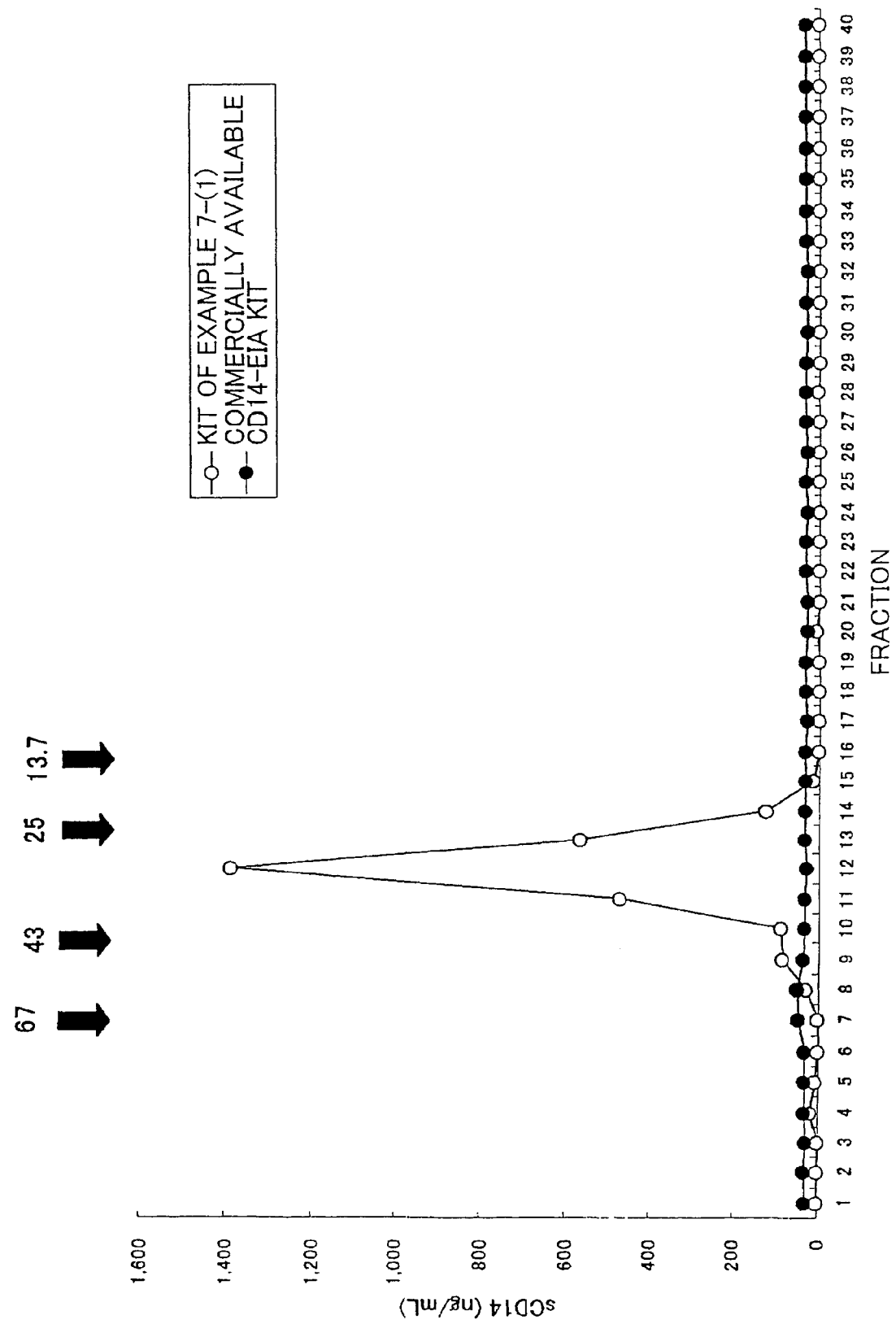
FIG. 6 shows the result of the analysis of the soluble CD14 antigen and the high molecular weight CD14 protein detected from the blood of a sepsis patient by the EIA kit of Example 7-(1). The serum of a sepsis patient was fractionated by S68-Sepharose™ 4FF antibody column by using F1024-1-3-Sepharose™ 4B for the precolumn, and the fractions were further fractionated by gel filtration chromatography. The fractions were then analyzed by the EIA kit of Example 7-(1) and a commercially available CD14-EIA kit (IBL-Hamburg). The solid arrows on the top of the graph indicate positions of the markers used for calibration which are, from left, BSA, ovalbumin, chymotrypsinogen A, and ribonuclease A.
Figure 7:
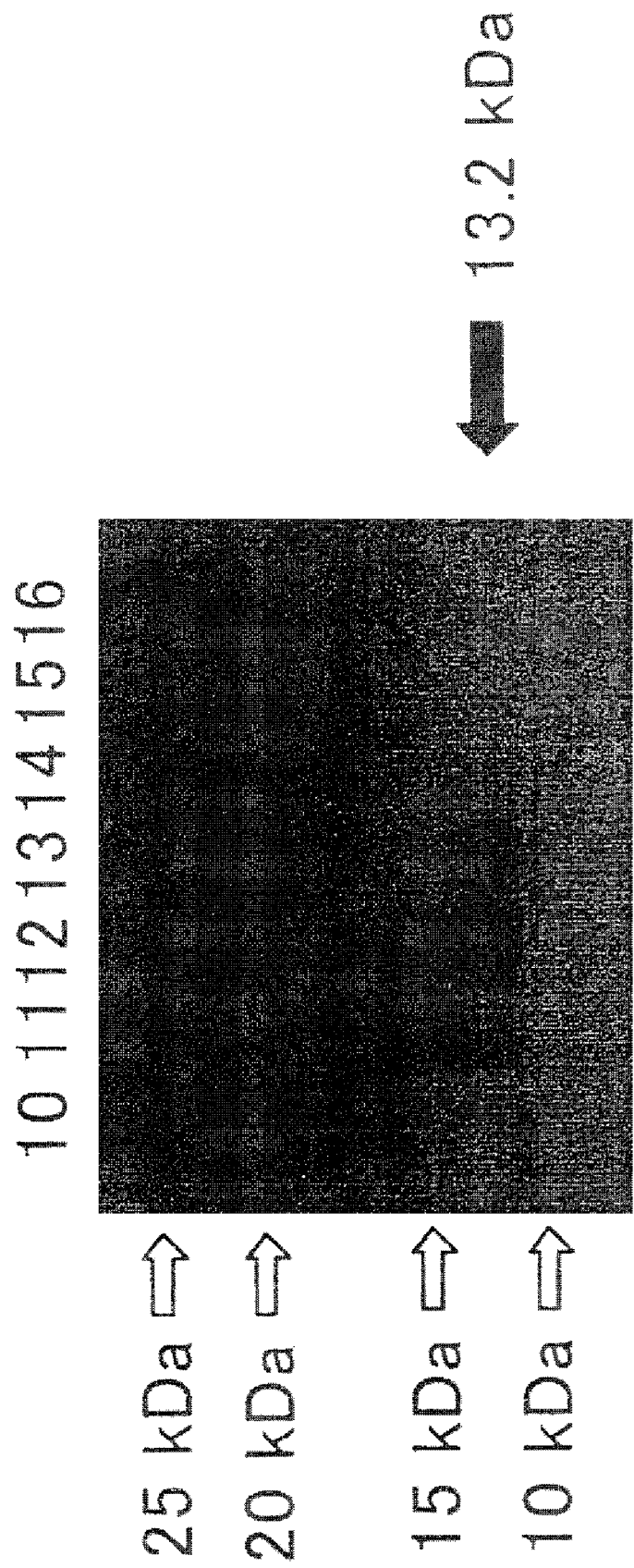
FIG. 7 shows the result of western blotting of the freeze dried fractions 10-16 obtained by the gel filtration chromatography described in FIG. 6.

Subsequently, these gel filtration fractions were subjected to the Western-blotting analysis shown in Example 9-(4). The soluble protein in blood which could be detected by the kit of Example 7-(1) was identified and the molecular weight thereof was then determined, using Precision Plus Protein™ Dual Color Standards (Bio-Rad Laboratories, Inc.). As a result, the concentration of the protein increased or decreased in agreement with the results of the measurement on the gel-filtered fractions with the kit of Example 7-(1). For the soluble protein in blood having a peak in Fraction 12, a band of 13±2 kDa in molecular weight was detected (FIGS. 6 and 7).

Example 10

Purification of Soluble Protein in Blood from Normal Human Serum 10-(1) Purification of Soluble Protein in Blood from Normal Human Serum A normal human serum purchased from Nippon Biotest Laboratories inc. was quantitatively analyzed using the kit of Example 7-(1), resulting in a level of 61 ng/ml.

Subsequently, 20 ml of the F1024-1-3-Sepharose 4B carrier prepared in Example 9-(1) was stuffed in a XK column 26/20 column (Amersham Biosciences) and then equilibrated with D-PBS (pH 7.4) containing 0.05% Tween 20. In addition, 8 ml of the S68-Sepharose 4FF carrier prepared in Example 9-(2) was stuffed in a XK column 16/20 column (Amersham Biosciences) and likewise equilibrated with D-PBS (pH 7.4) containing 0.05% Tween 20.

Next, these two columns were connected in tandem such that the F1024-1-3-Sepharose 4B column was arranged on the tip of the S68-Sepharose 4FF column. Then, 1.3 L of the normal human serum was supplied into the connected column assembly at a flow rate of 0.5 ml/min. Protein which could not be adsorbed onto the column was washed out with D-PBS (pH 7.4) containing 0.05% Tween 20. After that, the S68-Sepharose 4FF column was detached from the assembly and protein adsorbed onto the S68-Sepharose 4FF column was eluted at a flow rate of 1 ml/min. for 160 minutes with 10 mM HCl containing 0.05% Tween 20, during which 20-ml aliquots were collected in different vessels, successively. To each of the vessels used was previously added 2 ml of 500-mM ammonium bicarbonate, so that the pH of the eluate could be immediately returned to neutral. The concentration of the soluble protein in blood in each fraction to be detected by the kit of Example 7-(1) was determined and the fraction containing such protein was then freeze-dried after pooling.

The resulting freeze-dried powder was dissolved by addition of 1 ml of 150-mM ammonium acetate solution containing 0.05% Tween 20, and then filtered through a 0.22-µm pore size filter (Mylex™ GV13, Millipore), followed by gel filtration with a Superdex™ 75 10/300 GL column (Amersham Biosciences). An elution buffer used was a 150-mM ammonium acetate solution containing 0.05% Tween 20 and then added to the column provided with 0.5 ml of the sample at a flow rate of 0.8 ml/min. From 7 or 8 minutes after the sample addition, 0.45-ml aliquots of the eluate were collected into 40 vessels, successively. The gel filtration was carried out twice.

Each fraction was subjected to the measurement with the kit of Example 7-(1) and a commercially-available CD14-EIA kit (IBL-Hamburg). As a result, the soluble protein in blood which could be detected by the kit of Example 7-(1) was found in Fractions 11-13 with a peak in Fraction 12. In addition, the peak of the protein which was obtained by the same way as that of Example 9-(4) was located at the position of 29±5 kDa.

Figure 8:
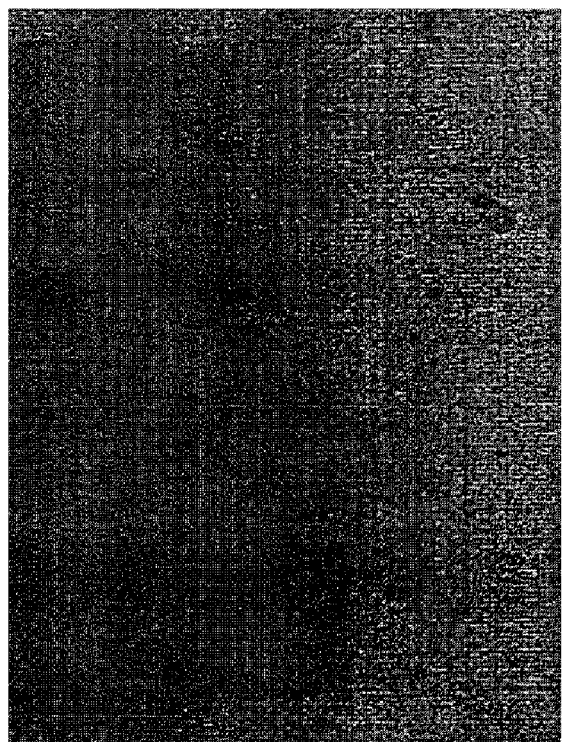
FIG. 8 shows the result of western blotting of the freeze dried fractions 10-16 obtained by the gel filtration chromatography after passing the serum of a normal donor through a precolumn of F1024-1-3-Sepharose™ 4B, and S68 antibody-Sepharose™ 4FF column.

Subsequently, these fractions obtained by gel filtration were subjected to the Western-blotting analysis shown in Example 9-(4). The soluble protein in blood which could be detected by the kit of Example 7-(1) was identified and the molecular weight thereof was then determined, using Precision Plus Protein™ Dual Color Standards (Bio-Rad Laboratories, Inc.). As a result, the concentration of the protein increased or decreased in agreement with the results of the measurement on the gel-filtered fractions with the kit of Example 7-(1). For the soluble protein in blood having a peak in Fraction 12, a band of 13±2 kDa in molecular weight was detected (FIG. 8).

The above fraction was pooled and freeze-dried. The resulting freeze-dried preparation was dissolved by addition of 100 μl of a 150-mM ammonium acetate solution containing 0.05% Tween 20. Subsequently, using the kit of Example 7-(1), the amount of the soluble protein in blood collected was determined. As a result, 19 μg of the soluble protein in blood was obtained from 1.3 L of the normal human serum.

10-(2) Identification of Amino Acid Sequence

[1] Electro-Blotting

The soluble protein in blood which could be detected by the kit of Example 7-(1) and freeze-dried in Example 10-(1) was developed on an acrylamide gel by SDS-PAGE described in Example 9-(3) and then electro-blotted on a polyvinylidene difluoride (hereinafter, referred to as PVDF) membrane. In other words, filter paper soaked in a 20% methanol/25 mM Tris/40 mM ε-aminocaproic acid solution was placed on a cathode of a transfer system, that is the platinum electrode semidry transfer system (Biocraft Ltd.), and an acrylamide gel after electrophoresis and a PVDF membrane (Clear Blot™ Membrane P (ATTO Corporation)) were then laid thereon. Furthermore, filter paper soaked in 20% methanol/25 mM Tris and filter paper soaked in 20% methanol/0.3 M Tris were laid thereon in this order. Finally, an anodic electrode of the system was placed thereon to carry out transfer at a constant current of 2 mA/cm² for one hour.

[2] Detection of Transferred Protein

The PVDF membrane after the electro-blotting was soaked in a 0.1% Coomassie brilliant blue G250/10% acetic acid/30% acetonitrile solution for about five minutes, followed by appropriate decolorization with a 10% acetic acid/30% acetonitrile solution to detect the protein of interest.

[3] Analysis of Amino Acid Sequence

The band of protein of 13±2 kDa in molecular weight, which was detected on the PVDF membrane, was cut from the membrane with a clean cutter and then transferred into a 1.7-ml microcentrifugation tube. The resulting PVDF membrane fragment was washed three times with a 0.1% trifluoroacetic acid/50% methanol solution and additionally with methanol, followed by completely drying the fragment. The amino acid sequence was analyzed using a protein sequencer, Procise™ 494 cLC (Applied Biosciences JAPAN, Ltd.). The PCDV membrane fragment after washing was mounted on the protein sequencer and a required analytic cycle was then set to carry out the analysis. As a result, as a major sequence, it was confirmed a peptide having an amino acid sequence of Thr Thr Pro Glu Pro Xaa Glu Leu Asp Asp Glu (SEQ ID NO: 32) on the N-terminal.

By the way, Xaa may be Cys, Asn, Ser, Thr, or any of other modified amino acids on the basis of the characteristics of the protein sequencer. However, considering that the protein analyzed is a protein derived from CD14, it may be Cys. In addition, the amino acid analysis with the reducing alkylation method can reveal that Xaa is Cys.

From those results, the fraction in which the band of 13±2 kDa in molecular weight of 12.5% SDS-PAGE under non-reducing conditions after the gel filtration was extracted, has a good degree of purity. Therefore, it is found that the soluble protein in blood to be detected by the kit of Example 7-(1) was purified.

Furthermore, the soluble protein in blood detected by the kit of Example 7-(1) was found to be a novel protein having an amino acid sequence of Thr Thr Pro Glu Pro Cys Glu Leu Asp Asp Glu (SEQ ID NO:1) from the first residue of CD14 on the N-terminal and a molecular weight of 13±2 kDa determined by SDS-PAGE under non-reducing conditions. Furthermore, as the soluble protein in blood can be detected by the kit of Example 7-(1), it is recognized that the protein will specifically bind to antibody prepared using a peptide consisting of 16 amino acid residues described in SEQ ID NO: 2 as an antigen.

From the results of Examples 9 and 10, it is revealed that the soluble protein in blood detected by the kit of Example 7-(1) and confirmed in the serum of a patient suffering from sepsis can be also found in the normal human serum. In addition, the protein would be collected at a higher rate in the serum of a patient suffering from sepsis.

Furthermore, even when a sandwich assay system using MEM-18 (Monosan) as an immobilized antibody and labeled 3C10 as a labeled antibody was used instead of the IBL-kit used in Examples 8-10, the same results as those obtained by the IBL-kit were obtained.

The labeling was carried out according to the description in Example 3-(3) and the sandwich assay system was prepared according to Example 7-(1).

Example 11

Measurement in Patients Suffering from Various Kinds of Diseases 10 examples from which isolates were identified were used (Table 5) as the sera of patients suffering from sepsis. In addition, the assay was conducted using the assay kit described in Example 7-(1) on 52 examples of normal donors (male 31 examples and female 21 examples), and patients suffering from various kinds of diseases (20 diseases, 60 examples).

TABLE 5

| Number | Sex | Age | Bacteria |
| --- | --- | --- | --- |
| 1 | Male | 41 | Coagulase-negative bacteria |
| 2 | Female | 44 | Coagulase-negative bacteria |
| 3 | Female | 61 | Faecium bacteria |
| 4 | Male | 52 | Serratia bacteria |

TABLE 5-continued

| Number | Sex | Age | Bacteria |
|---|---|---|---|
| 5 | Male | 37 | Escherichia coli |
| 6 | Female | 67 | Escherichia coli |
| 7 | Male | 70 | Staphylococcus aureus |
| 8 | Male | 51 | Pantoea agglomerans |
| 9 | Female | 81 | Escherichia coli |
| 10 | Male | 77 | Escherichia coli |

The level of soluble protein in serum of a normal donor as detected by the kit of Example 7-(1) was in the range of 0.008 to 0.100 μg/mL and the average thereof was 0.04 μg/mL. In the case of a patient suffering from sepsis, the level of the soluble protein was in the range of 0.190 to 7.260 μg/mL and the average thereof was 2.0 μg/mL. The level of the soluble protein of the patient suffering from sepsis was higher than those of the normal donors and patients suffering from other various kinds of diseases. Among patients suffering from other various kinds of diseases, there was no patient showing a high level, compared with that of the normal donor.

Example 12

Comparison with Commercially Available ELISA Kit for CD14 Protein Soluble in Blood 12-(1) Assay of Soluble CD14 Protein in Blood of Patients Suffering from Various Kinds of Diseases Specimens of Example 11 were assayed using the commercially available CD14-ELISA kit (IBL-Hamburg). The level of soluble CD14 protein in serum of a normal donor was in the range of 5.6 to 11.2 μg/mL but an example of a high level in the case of a patient suffering from sepsis was observed. However, many cases that showed high levels of soluble CD14 protein were found in sera of patients suffering from various kinds of disease, so that there was no difference from the patients suffering from sepsis.

12-(2) Comparison with Kit Using S68 Antibody

The comparison with and investigation of the measured levels of the soluble protein determined in Example 11 were performed. As shown in Table 6, the commercially available CD14-EIA kit showed an almost 1.7-fold difference at maximum among the normal donors, patients of various diseases, and sepsis patients, while the assay kit of Example 7-(1) showed a 50-fold difference between the normal donors and the sepsis patients in spite of no difference between the normal donors and patients of various diseases. Therefore, the result clearly showed that the measured level by the assay kit of Example 7-(1) specifically increases in sepsis.

TABLE 6

| | CD14 level in blood (μg/mL) | | | Ratio Sepsis/ Normal |
|---|---|---|---|---|
| | Normal | Various kinds of diseases | Sepsis | |
| Assay kit of Example 7-(1) | 0.04 | 0.06 | 2.0 | 50.0 |
| Commercially available CD14-EIA | 7.6 | 9.0 | 13.2 | 1.7 |

The average level+3 S.D of the tested normal donors was provided as a cut-off level (measurement kit of Example 7-(1): 0.134 μg/mL, commercially available CD14-EIA: 11.14 μg/mL) and then the analyses were divided into positive samples (sepsis) and negative samples (normal+various diseases). The results were shown in Table 7. According to the results, a rate of identity between both kits ((the number of identity for EIA positive+the number of identity for EIA negative)/total×100), sensitivity (the number of identity for EIA positive/positive samples×100), and specificity (the number of identity for EIA negative/negative samples×100) were calculated. As a result, as shown in Table 8, in the case of the kit of Example 7-(1), the rate of identity was 94.3%, the sensitivity was 100.0%, and the specificity was 93.8%. Thus, it was found that the kit of Example 7-(1) could be useful in differential diagnosis on sepsis by defining the cut-off level. On the other hand, in the case of the commercially available CD14-EIA, there was no sensitivity and specificity which were specific to allow diagnosis of sepsis.

TABLE 7

| | Classification | | | |
|---|---|---|---|---|
| | Positive sample | Negative sample | | |
| Disease | Sepsis | Normal | Various kinds of diseases | Total |
| Assay kit of Example 9-(1) | 10 | 51 | 54 | 115 |
| Commercially available CD14-EIA | 6 | 51 | 45 | 102 |
| Total | 10 | 52 | 60 | 122 |

TABLE 8

| | Assay kit of Example 7-(1) | Commercially available CD14-EIA |
|---|---|---|
| Rate of identity (%) | 94.3% | 83.6% |
| Sensitivity (%) | 100.0% | 60.0% |
| Specificity (%) | 93.8% | 85.7% |

Example 13

Preparation of Recombinant Soluble CD14 Fragment

This fragment was prepared to express the soluble protein in blood purified in Example 10 (hereinafter, it can be also referred to as a soluble CD14 subtype, or abbreviated as a low-molecular sCD14-ST) as a recombinant protein.

13-(1) Construction of Plasmid for Expression of C-Terminal-Deleted CD14 Modified Product For preparing a recombinant soluble CD14 fragment (hereinafter, it can be also referred to as a recombinant soluble CD14 subtype or abbreviated as a rsCD14-ST), a plasmid which produces C-terminal-deleted CD14 was constructed.

Expression plasmids that are pCAG65, pCAG70, pCAG75, pCAG80, pCAG85, pCAG90, pCAG95, pCAG100, pCAG105, and pCAG110, each expressing in mammalian cells human CD14 molecules (SEQ ID NO: 3) including:

1) a molecule in which a portion of from position 66 to C-terminal is deleted (hereinafter, it will be described as CD14 (1-65), and the same can be said hereinafter);

2) a molecule in which a portion of from position 71 to C-terminal is deleted (CD14 (1-70));

3) a molecule in which a portion of from position 76 to C-terminal is deleted (CD14 (1-75));
4) a molecule in which a portion of from position 81 to C-terminal is deleted (CD14 (1-80));
5) a molecule in which a portion of from position 86 to C-terminal is deleted (CD14 (1-85));
6) a molecule in which a portion of from position 91 to C-terminal is deleted (CD14 (1-90));
7) a molecule in which a portion of from position 96 to C-terminal is deleted (CD14 (1-95));
8) a molecule in which a portion of from position 101 to C-terminal is deleted (CD14 (1-100));
9) a molecule in which a portion of from position 106 to C-terminal is deleted (CD14 (1-105)); and
10) a molecule in which a portion of from position 111 to C-terminal is deleted (CD14 (1-110)) were constructed by using the method described below.

The following primers were designed: a sense primer 1 (5'-TTT CCT ACA GCT CCT GGG-3') (SEQ ID NO: 11) and an antisense primer 1 (5'-GG GGT ACC TTA GTC AGC ATA CTG CCG CGG GTC-3') (SEQ ID NO: 12); an antisense primer 2 (5'-GG GGT ACC TTA GAG AGC CTT GAC CGT GTC AGC-3') (SEQ ID NO: 13); an antisense primer 3 (5'-GG GGT ACC TTA GAG CCG CCG CAC GCG GAG AGC-3') (SEQ ID NO: 14); an antisense primer 4 (5'-GG GGT ACC TTA TGC GGC TCC CAC TGT GAG CCG-3') (SEQ ID NO: 15); an antisense primer 5 (5'-GG GGT ACC TTA CTG AGC AGG AAC CTG TGC GGC-3') (SEQ ID NO: 16); an antisense primer 6 (5'-GG GGT ACC TTA GGC GCC TAC CAG TAG CTG AGC-3') (SEQ ID NO: 17); an antisense primer 7 (5'-GG GGT ACC TTA CGC TAG CAC ACG CAG GGC GCC-3') (SEQ ID NO: 18); an antisense primer 8 (5'-GG GGT ACC TTA CTT GAG GCG GGA GTA CGC TAG-3') (SEQ ID NO: 19); an antisense primer 9 (5'-GG GGT ACC TTA CTC GAG CGT CAG TTC CTT GAG-3') (SEQ ID NO: 20); and an antisense primer 10 (5'-GG GGT ACC TTA GGT TAT CTT TAG GTC CTC GAG-3') (SEQ ID NO: 21). Next, PCR was conducted by using pCAG356 as a template and a set of primers: a sense primer 1 and an antisense primer 1; an sense primer 1 and an antisense primer 2; a sense primer 1 and an antisense primer 3; a sense primer 1 and an antisense primer 4; a sense primer 1 and an antisense primer 5; a sense primer 1 and an antisense primer 6; a sense primer 1 and an antisense primer 7; a sense primer 1 and an antisense primer 8; a sense primer 1 and an antisense primer 9; and a sense primer 1 and an antisense primer 10 respectively. PCR reaction condition was set for heating at 90° C. for 2 minutes, followed by repeating 30 times a cycle of (i) heating at 98° C. for 10 seconds, (ii) heating at 50° C. for 30 seconds, and (iii) heating at 72° C. for 1 minute, to thereby obtain a product. The resultant products were double-digested using restriction enzymes EcoRI and KpnI to collect each fragment of 0.4 kb to 0.5 kb. Those fragments were ligated to a fragment of about 4.8 kb obtained by cleaving pCAG356 with restriction enzymes EcoRI and KpnI, followed by transformation of E. coli JM109 according to the conventional method to obtain each of expression plasmids. It is noted that pCAG356 is a plasmid obtained by inserting a CD14 gene derived from a plasmid pUCH14 P-4 described in WO98/39438 in pCGAAS (GENE, vol. 15 p 269-277 (1989)).

13-(2) Construction of CD14 Expression Plasmid Having Cleavage Sequence of Protease Inserted Therein The amount of rsCD14-ST produced by the production method using the plasmid described in Example 13-(1) was very small. Thus, it was judged that the fragment expressed in the rsCD14-ST production method using the plasmid described in Example 1-(1) could not be used as a reference material to be purified to obtain a pure product. Thus, there was selected a method involving the steps of inserting a cleavage sequence of a protease which specifically cleaves at position 64 CD14 having 356 amino acid residues in length into the plasmid, specifically cleaving the sequence by a protease after expression of the full length CD14, isolating a portion at positions 1-64 of SEQ ID NO: 3 from the remaining portion and purifying to prepare rsCD14-ST. Two cleaving sequences including a PreScission Protease recognition sequence and a Thrombin recognition sequence were used for protease.

13-(2)-1 Construction of rsCD14-ST (PSP64/356) Expression Plasmid

A plasmid for the expression of rsCD14 (hereinafter, also referred to as rsCD14-ST (PSP64/356)) having a PreScission Protease recognition sequence (8 amino residues: LEVLFQGP (SEQ ID NO: 30), each represented by a single letter) inserted between the amino acids of Ala at position 64 and Asp at position 65 of human CD14 described in SEQ ID NO: 3 was constructed by the method described below. A sense primer 1 (5'-TTT CCT ACA GCT CCT GGG-3') (SEQ ID NO: 11), a sense primer 2 (5'-GCT CTG GAA GTT CTG TTC CAG GGG CCC GAC ACG GTC AAG GCT CTC CGC GTG CGG-3') (SEQ ID NO: 22), an antisense primer 11 (5'-GTC GGG CCC CTG GAA CAG AAC TTC CAG AGC ATA CTG CCG CGG GTC GGC GTC CGC-3') (SEQ ID NO: 23), and an antisense primer 12 (5'-TCT CCA TTC CTG TGT TGC GC-3') (SEQ ID NO: 24) were designed and synthesized, respectively. A plasmid pCAG356 in which a soluble human CD14 structural gene sequence described in SEQ ID NO: 3 was inserted was used as a template to carry out PCR using A: the sense primer 1 and the antisense primer 11 and B: the sense primer 2 and the antisense primer 12. The reaction conditions of PCR were: for A, heating at 90° C. for 2 min., followed by repeating 30 times a cycle of (i) 98° C. for 10 sec., (ii) 50° C. for 30 sec., and (iii) 72° C. for 1 min.; and for B, heating at 90° C. for 2 min., followed by repeating 30 times a cycle of (i) 98° C. for 10 sec., (ii) 46° C. for 30 sec., and (iii) 72° C. for 1 min. The resulting PCR-amplified products A: about 0.5 kb and B: about 0.5 kb were collected. Subsequently, PCR reactions using these two mixtures as templates and the sense primer 1 and the antisense primer 12 were carried out, respectively. The same PCR reaction conditions as those of the above A were used. The resulting PCR-amplified product of about 0.9 kb was collected and then cleaved by restriction enzymes EcoRI and XhoI. The fragment obtained was ligated to a fragment of about 5.2 kb obtained by cleaving pCAG356 with the restriction enzymes EcoRI and XhoI, followed by transformation of E. coli JM109 by the conventional method. The obtained plasmid was named pCAG356 (PSP64/356). Furthermore, pCAG356 was digested with restriction enzymes EcoRI and KpnI and a fragment of about 1.3 kb was collected. This fragment was ligated to a fragment of about 4.4 kb obtained by digesting mammalian cell expression vector pTK-2043 having human EF-1α promoter with EcoRI and KpnI, followed by transformation of E. coli JM109 by the conventional method. Consequently, pTK356 (PSP64/356) was obtained.

13-(2)-2 Construction of rsCD14-ST (2ST64/356) Expression Plasmid

A plasmid for the expression of rsCD14 (hereinafter, also referred to as rsCD14-ST (2ST64/356) having a Thrombin recognition sequence (6 amino residues: LVPRGS) (SEQ ID NO: 31) inserted between the amino acids of Ala at position 64 and Asp at position 65 in human CD14 described in SEQ ID NO: 3 was constructed by the method described below. A sense primer 3 (5'CTG GTT CCG CGT GGT TCC GAC ACG GTC AAG-3') (SEQ ID NO: 25), an antisense primer 13 (5'-GAA CCA CGC GGA ACC AGA GCA TAC TGC CGC-3') (SEQ ID NO: 26), and an antisense primer 14 (5'-CGG GAT CCT CAA TGA TGA TGA TGA TGA TGG-3') (SEQ ID NO: 27) were designed and synthesized, respectively. A plasmid pCAG356-His having a structural gene sequence of a molecule in which a His tag (His×6) was added to C-terminal of a soluble human CD14 of a plasmid pCAG356 was used as a template to carry out PCR using A: the sense primer 1 and the antisense primer 13 and B: the sense primer 3 and the antisense primer 14. The reaction condition of PCR was heating at 96° C. for 2 min., followed by repeating 25 times a cycle of (i) 96° C. for 30 sec., (ii) 55° C. for 30 sec., and (iii) 72° C. for 1 min. The resulting PCR-amplified products A: about 0.5 kb and B: about 0.9 kb were collected. Subsequently, PCR reactions using the two mixtures as templates and the sense primer 1 and the antisense primer 4 were carried out, respectively. The same PCR reaction conditions as those of the above A were used. The resulting PCR-amplified product of about 1.4 kb was collected and was then inserted into a pT7-Blue (T) vector. The nucleotide sequence was confirmed, followed by cleavage with restriction enzymes EcoRI and BamHI. The obtained fragment of about 1.3 kb was ligated to a fragment of about 4.4 kb obtained by digesting pTK-2043 with EcoRI and BamHI, followed by transformation of E. coli JM109 by the conventional method. Consequently, pTK356H (TB64) was obtained.

13-(3) Preparation of rsCD14-ST 13-(3)-1 Preparation of rsCD14-ST

Each plasmid described in (1) was transfected into COS-1 cells (ATCC: CRL-1650) using Fugene™ 6 (Roche). In other words, according to the manual, 1.7 μl/ml of a transfection reagent was mixed with 4 μg/ml of the plasmid and the mixture was added to a culture medium, followed by the addition of COS-1 cells. Then, the cells were incubated at 37° C. After 72 hours, the culture supernatant was collected. The culture supernatant was centrifuged and then filtered through a 0.22-μm filter.

13-(3)-2 Preparation of rsCD14

Transfection of the plasmids (pTK356 (PSP64/356) and pTK356H (TB64)) each containing a gene encoding the sequence of rsCD14-ST as described in (2)-1 and (2)-2 was carried out using Fugene 6 (Roche) for COS-1 cells. In other words, according to the manual, 1.7 μl/ml of a transfection reagent was mixed with 4 μg/ml of the plasmid and the mixture was added to a culture medium, followed by the addition of COS-1 cells. Then, the cells were incubated at 37° C. After 72 hours, the culture supernatant was collected, while a flesh medium was supplied. The cells were further incubated for 96 hours and the culture supernatant was also collected. The culture supernatant was centrifuged and then filtered through a 0.22-μm filter, followed by purification.

13-(3)-3 Preparation of rsCD14-ST (2)

From each culture supernatant produced in (3)-2, rsCD14-ST (PSP64/356) and rsCD14-ST (2ST64/356) were purified and then cleaved by a protease, followed by purifying sCD14-ST.

<1> Purification of rsCD14-ST (2ST64)

The following procedures were carried out at 4° C. unless otherwise specified.

An equivalent volume of a 0.1-M nickel sulfate aqueous solution was poured into the Chelating-Sepharose FF (Amersham Biosciences) carrier. Then, three volumes of distilled water was poured into the column to wash out unreacted nickel. Consequently, a nickel-Sepharose carrier was prepared.

A 1000-ml COS-1 culture supernatant obtained in (3)-2 was applied to a 40-ml nickel-Sepharose column equilibrated with PBS at a flow rate of 8 ml/min to wash out unadsorbed protein with PBS. Subsequently, any protein nonspecifically adsorbed was eluted by PBS containing 20 mM imidazole and the protein of interest was then eluted by PBS containing 500 mM imidazole. The eluate was dialyzed against PBS overnight.

The concentration of protein in the dialysate was determined using the procedure described in Example 15-(3) below. Based on this result, thrombin protease (Amersham Biosciences) was added so as to attain the ratio of enzyme: substrate=1:50 (U:μg) and then left to stand at 22° C. overnight, followed by carrying out a cleaving reaction with thrombin.

The enzyme reaction was terminated by the addition of 1/10 volumes of a 100-mM benzamidine aqueous solution. Subsequently, to the resulting mixture was added two volumes of a 50-mM Tris-HCl (pH 8.5) buffer containing 8 M urea. The solution was poured into a 3-ml Q-Sepharose HP (Amersham Biosciences) column previously equilibrated with a 50-mM Tris-HCl (pH 8.5) buffer containing 8 M urea at a flow rate of 3 ml/min. Nonadsorbed protein was washed out with the same buffer and adsorbed protein was then eluted with a linear concentration gradient of 0-500 mM NaCl (50 minutes). 3-ml aliquots of the eluate were collected in different vessels, sequentially. The content of a fraction, which corresponds to rsCD14-ST (hereinafter, also referred to as rsCD14-ST (2ST64)) obtained by cutting out the position 65 of rCD14-ST (2ST64/356) of each fraction, was determined by the kit described in Example 7-(3).

Figure 9:
FIG. 9 is the image of the purified rsCD14-ST(2ST64) and (PSP64) which were electrophoresed by SDS-PAGE and stained by silver staining.

The fraction containing rsCD14-ST (2ST64) was pooled and then dialyzed overnight for a 150-mM ammonium hydrogencarbonate aqueous solution, followed by freeze-drying. The resulting freeze-dried preparation was dissolved in PBS containing 8 M urea and then supplied to Superdex™ 75 10/300 GL column (Amersham Biosciences) previously equilibrated with the same buffer at a flow rate of 0.4 ml/min. 0.45-μl aliquots of the column solution were taken up in 40 vessels, respectively. The purity of rsCD14-ST (2ST64) in each fraction was confirmed by SDS-PAGE and then pooled. That is, an equivalent volume of Tris-SDS-Seprasol™ (Daiichi Pure Chemicals Co., Ltd.) was added to each fraction and then heated at 100° C. for five minutes, followed by applying the mixture to a 5-20% e-PAGEL™ gel (ATTO corporation) to carry out electrophoresis using the procedures of Laemmli at 25 mA for 90 minutes. After the termination of the electrophoresis, the gel was stained with the silver-staining kit, 2D Silver Stain II "Daiichi" (Daiichi Pure Chemicals Co., Ltd.). The 2ST64 preparation was dialyzed against distilled water overnight to obtain a final purified preparation. The concentration of protein in the final purified preparation was determined according to the procedure described in Example 15-(3) below. From the operation described above, 452 μg of rsCD14-ST (2ST64) was obtained from the supernatant of 1,000 ml of the culture medium of COS-1 cells. The purity of the purified preparation thus obtained was confirmed using SDS-PAGE. As shown in FIG. 9, it was detected as a single band.

<2> Purification of rsCD14-ST (PSP64)

The following procedures were carried out at 4° C. unless otherwise specified.

The COS-1 culture supernatant obtained in (3)-2 was applied to the 3C10-Sepharose 4FF column previously equilibrated with PBS at a flow rate of 9 ml/min., and nonadsorbed protein was then washed out with PBS, followed by eluting adsorbed protein by 10 mM HCl. To the eluted fraction was added 1/10 volumes of 500 mM ammonium bicarbonate, so that the pH of the eluate could be immediately returned to neutral. After that, the eluted fraction was freeze-dried. Furthermore, the 3C10-Sepharose 4FF column was prepared as follows: 3C10 antibody was dialyzed at 4° C. overnight using a dialysis membrane having a molecular weight cut-off of 10 kDa and 2.5 L of a dialysate (i.e., 0.2 M NaHCO$_3$ (pH 8.3) containing 0.5 M NaCl). The dialysate was replaced with new one three times. Subsequently, NHS-Activated Sepharose 4 Fast Flow column (Amersham Biosciences) previously equilibrated with 0.2 M NaHCO$_3$ (pH 8.3) containing 0.5 M NaCl was added to the dialyzed 3C10 antibody solution to carry out a coupling reaction at 4° C. overnight. Next, 0.5 M monomethanolamine (pH 8.3) containing 0.5 M NaCl was added to the carrier to carry out a blocking reaction at 4° C. overnight. After the termination of the blocking reaction, the carrier was washed with 0.1 M sodium acetate (pH 4.0) containing 0.5 M NaCl and subsequently with 0.2 M NaHCO$_3$ (pH 8.3) containing 0.5 M NaCl.

The resulting freeze-dried preparation was dissolved in a 50-mM Tris-HCl (pH 7) buffer containing 1 mM EDTA and 150 mM NaCl and the concentration of protein therein was then determined according to the procedure described in Example 15-(3) below. After that, PreScission Protease™ (Amersham Biosciences) was added so as to attain the ratio of enzyme:substrate=1:3 (U:μg) and then left to stand at 4° C. overnight to carry out a cleaving reaction. After the termination of the reaction, to the resulting mixture was added two volumes of a 50-mM Tris-HCl (pH 8.5) buffer containing 8 M urea and then the mixture was applied to a 2-ml Q-Sepharose HP column at a flow rate of 1 ml/min. Nonadsorbed protein was washed out with the same buffer and then eluted by a linear concentration gradient of 0-500 mM NaCl (100 minutes). 3-ml aliquots of the eluate were collected in different vessels, sequentially. The content of a fraction, which corresponds to rsCD14-ST (hereinafter, also referred to as rsCD14-ST (PSP64)) obtained by cutting rCD14-ST (PSP64/356) of each fraction at the position 65, was determined by the kit described in Example 7-(3).

The fraction containing rsCD14-ST (PSP64) was pooled and then dialyzed overnight for a 150-mM ammonium hydrogencarbonate aqueous solution, followed by freeze-drying. The resulting freeze-dried preparation was dissolved in PBS containing 8 M urea and then supplied to Superdex™ 75 10/300 GL column (Amersham Biosciences) previously equilibrated with the same buffer at a flow rate of 0.4 ml/min. 0.45-ml aliquots of the column solution were taken up in 40 vessels, respectively. The purity of rsCD14-ST (PSP64) in each fraction was confirmed by SDS-PAGE shown in <1> and then pooled. The rsCD14-ST (PSP64) preparation was dialyzed against distilled water overnight to obtain a final purified preparation. The concentration of the protein in the final purified preparation was determined according to the procedure described in Example 15-(3) below. From the operation described above, 368 μg of PSP64 was obtained from the supernatant of 13,000 ml of the culture medium of COS-1 cells. The purity of the purified preparation thus obtained was confirmed using SDS-PAGE. As shown in FIG. 9, it was detected as a single band.

Example 14

Evaluation of rsCD14-ST 14-(1) Concentration Measurement Using Kit of Example 7-(3)

For confirming whether rsC14-ST was produced in the supernatant of the culture medium prepared in Example 13-(3)-1, the concentration of rsCD14-ST in each culture supernatant was determined using the kit of Example 7-(3). The results are shown in Table 9. In addition, each culture supernatant was subjected to Western-blotting by the method described in Example 9-(4). As a result, no band was detected at all. From this fact, it was determined that the actual content of protein could be very small even though rsCD14-ST might be produced and detected by a high-sensitive detection kit.

TABLE 9

| | Deleted product | | | | | | | | | |
|---|---|---|---|---|---|---|---|---|---|---|
| | 1-65 | 1-70 | 1-75 | 1-80 | 1-85 | 1-90 | 1-95 | 1-100 | 1-105 | 1-110 |
| Concentration (μg/ml) | 195 | 590 | 273 | 100 | 55 | 16 | 0.43 | 0.21 | 0.29 | 0.18 |

For example, the deleted product 1-65 represents a fragment of positions 1 to 65 of SEQ ID NO: 3 (rsCD14 (1-65)).

14-(2) Detection of rsCD14-ST by Western Blotting

Reactivities of sCD14-ST prepared in Example 10-(1) and rsCD14-ST (PSP64) prepared in Example 13-(3)-3 to F1106-13-3 antibody, F1031-8-3 antibody, and S68 antibody were confirmed, respectively. In other words, SDS-PAGE was carried out using a 12.5% SDS-polyacrylamide gel under non-reducing conditions according to the procedures of Laemmli. An equivalent volume of Tris-SDS-Seprasol (Daiichi Pure Chemicals Co., Ltd.) was added to the sample and a SDS treatment was then carried out at 4° C. overnight, followed by applying the mixture to 12.5% of e-PAGEL™ gel (ATTO Corporation) to carry out electrophoresis using the Laemmli's discontinuous buffer system at 40 mA for 40 minutes.

Filter paper previously cut to fit the size of the SDS-PAGE gel was soaked in a 5% methanol/25 mM Tris/40 mM ε-aminocaproic acid solution and then placed on the cathode plate of the platinum electrode semidry transfer system BE320 (Biocraft Ltd.). Subsequently, the gel was soaked in the same solution and then laid on the filter paper without causing air bubbles therein. After that, nitrocellulose membranes (Trans-Blot™ Transfer-Medium, Bio-Rad Laboratories, Inc.), previously equilibrated in 5% methanol/25 mM Tris, were laid on the gel without causing air bubbles therein. Furthermore, the filter paper previously soaked in the same solution was also lied thereon without causing air bubbles therein and finally the filter paper soaked in 5% methanol/300 mM Tris was laid thereon without causing air bubbles. Furthermore, the anodic electrode was placed thereon to carry out transfer at 2 mA/cm$^2$ at room temperature for two hours. After the termination of the transfer, the nitrocellulose membranes were soaked in Block-Ace™ (Dainippon Pharmaceutical Co., Ltd.) to carry out a blocking operation at 37° C. for 80 minutes. After that, the nitrocellulose membranes were allowed to react with 6.8 μg/ml of F1106-13-3 antibody, 6.8

µg/ml of F1031-8-3 antibody, and 6.8 µg/ml of S68 antibody on a one-to-one basis, at 37° C. for 80 minutes and then washed with 0.05% Tween 20/PBS, followed by reacting the nitrocellulose membranes reacted with F1106-13-3 antibody and F1031-8-3 antibody with an anti-mouse Igs antibody-HRP conjugate (DAKO) and reacting the nitrocellulose membrane reacted with S68 antibody with an anti-rabbit IgG antibody-HRP conjugate (DAKO) at 37° C. for one hour, respectively. After the termination of the reaction, the nitrocellulose membranes were washed with 0.05% Tween 20/PBS. After unreacted conjugate had washed out, 4 ml of ECL (Plus)™ (Amersham Biosciences) was added and then the whole was reacted at room temperature for five minutes, followed by placing on the Hyperfilm™ ECL™ (Amersham Biosciences) and exposing for 90 seconds.

Consequently, sCD14-ST and PSP64 showed almost similar reactivities to three different antibodies, respectively.

Example 15

Analysis on Physical Properties of rsCD14-ST

The physical properties of rsCD14-ST (2ST64) and rsCD14-ST (PSP64) prepared in Example 13-(3)-3 were analyzed, respectively. For both fragments, there is no difference between their purified final products except the proteases used for cleavage and thus they are substantially the same material in terms of rsCD14-ST.

15-(1) Analysis on N-Terminal Amino Acid Sequence

The analysis on the N-terminal amino acid sequence was carried out using the protein sequencer, Procise 494 cLC™ (Applied Biosystems Japan Ltd.). As a result of analysis on the rsCD14-ST (2ST64) purified preparation, it was confirmed that the amino acid sequence (TTPEPCELDDG) (SEQ ID NO: 1) was a main component from the first residue of CD14. No amino acid sequence other than CD14 was confirmed.

15-(2) Mass Spectrometry

The rsCD14-ST (2ST64) purified preparation was incubated at 37° C. for four hours in a 20-mM sodium phosphate buffer containing N-glycosidase F (Roche Diagnostics K.K.) to remove sugar chains. The resulting sugar-chain-removed 2ST64 was demineralized with ZipTipC18 (Millipore) and provided as a sample for mass spectrometry. A mass spectrometer used was the autoflex II TOF (Bruker Daltonics Inc.). A matrix solution was prepared by dissolving sinapic acid so as to be saturated in 0.1% trifluoroacetate:acetonitrile=2:1. The sample for mass spectrometry was mixed with the matrix solution at a ratio of 1:4 and a 1-µL aliquot thereof was used in mass spectrometry. As a result of mass spectrometry, the molecular weight peak corresponding to the theoretical molecular weight 7663.5 of the peptide portion of rsCD14-ST(2ST64) was detected as a main peak. Also taking into account the results of the N-terminal amino acid sequence analysis it was confirmed that a molecule having a primary structure as designed (molecule consisting of an amino acid sequence at positions 1-64 in CD14) was obtained.

15-(3) Determination of Protein Concentration

The measurement of protein concentration was carried out using the BRP assay kit (Bio-Rad Laboratories, Inc.) with a BSA (Bio-Rad Laboratories, Inc.) standard preparation according to the accompanying manual. In other words, a 1.5-ml Dye-Reagent diluted five times with distilled water was added to 30 µL of the sample diluted to various concentrations with the BSA standard solution and PBS and then the mixture was left to stand at room temperature for 15 minutes, followed by measuring the absorbance of the sample at 595 nm using a spectrophotometer DU-7400 (Beckmann) to determine the concentration of protein in the sample from the calibration curve of BSA.

15-(4) Estimation of Molecular Weight

For confirming that rsCD14-ST prepared in Example 13-(3)-3 and sCD14-ST purified from patients suffering from sepsis or normal donors were similar proteins, their molecular weights were compared using Western blotting.

The sCD14-ST purified preparation from the normal human serum was used such that the freeze-dried preparation obtained in Example 10-(1) was dissolved in 100 µl of distilled water.

Figure 10:
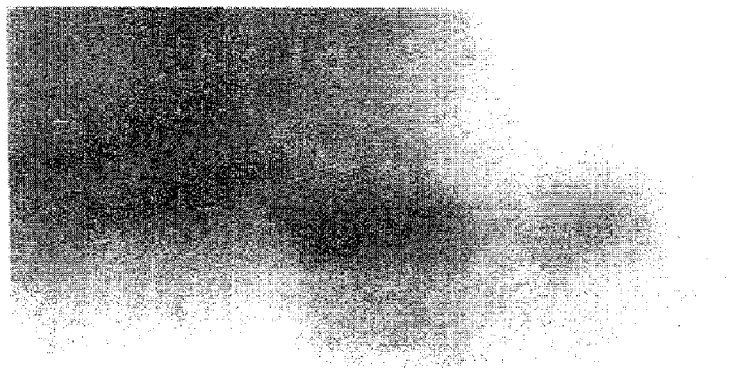
FIG. 10 is the image of western blotting of sCD14-ST and PSP64 stained with S68 antibody.

By the Western blotting using F1031-8-3 antibody represented in Example 14-(2), the comparison between molecular weights was carried out using Precision Plus Protein Dual Color Standards™ (Bio-Rad Laboratories, Inc.). Consequently, as shown in FIG. 10, sCD14-ST derived from human serum was detected at a molecular weight of 12.9 kDa, rsCD14-ST (2ST64) was detected at 12.6 kDa, and rsCD14-ST (PSP64) was detected at 12.6 kDa.

15-(5) Comparison with Specific Activity of rsCD14(1-307) S286C Standard Preparation The concentration of rsCD14-ST(2ST64) prepared in Example 13-(3)-3 was determined using the kit of Example 7-(1) and the rsCD14 (1-307) S286C standard preparation and calculated in terms of an EIA value per protein concentration. In other words, rsCD14-ST (2ST64) was diluted to 100 pg/ml by a sample-diluting solution of the kit. In addition, 50 and 25 pg/mL of the sample was prepared and then subjected to the measurement with the kit. As a result, the rsCD14 (1-307) S286C converted value per 1 pg of sCD14-ST (2ST64) was 352 pg, so that the present kit was shown to have extremely high reactivity to rsCD14-ST (2ST64).

15-(6) Influence on LPS Binding Ability and IL-6 Production

Whether rsCD14-ST had LPS binding ability as in the full length CD14 and the effect of inhibiting IL-6 production described in WO01/72993 was investigated.

15-(6)-1 Inhibitory Activity of rsCD14-ST (PSP64) on IL-6 Production

For investigating the inhibitory activity of sCD14-ST (PSP64) on IL-6 production, the following experiment was conducted. Human umbilical vascular endothelial cells HUVEC (Sanko Junyaku, Co., Ltd.) were inoculated in a 96-well plate at a concentration of $2 \times 10^4$ cells/well with a RPMI1640 medium (Sigma Corporation) containing 2% of inactivated FBS and then incubated under 5% $CO_2$ at 37° C. overnight. On the next day, a RPMI1640 medium containing 2% human serum (hereinafter, referred to as 2% inactivated-FBS/RPMI) was prepared and a sample was then prepared by 2-fold dilution of the desired concentration of 3C10 which was rsCD14-ST (PSP64) or the anti-CD14 antibody, with 2% inactivated-FBS/RPMI. In addition, LPS (*E. coli* 055: B5, DIFCO) was diluted to 20 ng/ml with 2% inactivated-FBS/RPMI. The culture supernatant of HUVEC cells incubated overnight was discarded and then washed twice with a RPMI1640 medium containing 0.1% HSA (Sigma). The sample and the LPS diluent were added at 50 µl/well, respectively. The mixture was incubated under 5% $CO_2$ at 37° C. for about additional 18 hours. After that, the amount of IL-6 in the culture supernatant was quantitatively determined using the human IL-6 detection kit (Eli-PAIR™ hIL-6: Invitrogen). Consequently, almost 50% of the IL-6 production was inhibited by about 0.1 µg/ml of 3C10, while rsCD14-ST (PSP64) could not show inhibitory activity even though rSCD14-ST (PSP64) was added up to 10 µg/ml.

15-(6)-2 LPS Binding Activity of rsCD14-ST (PSP64)

The presence of LPS-binding ability was investigated in rsCD14-ST (PSP64) using Endospecy™ kit (Seikagaku Corporation) with reference to J.B.C., vol. 270, No. 3 (1995), pp. 1382-1387, "Soluble CD14 Truncated at Amino Acid 152 Binds LPS and Enables Cellular Response to LPS". That is, LPS (*E. Coli* 055: B5, DIFCO) was diluted with PBS(−) containing 0.01% BSA (hereinafter, referred to as 0.01% BSA/PBS) to prepare 0.6 ng/ml of a LPS solution. In addition, rhLBP (R&D Systems) was diluted with PBS(−) containing 0.1% HSA to 100 µg/mL and then mixed with the LPS solution to prepare a LPS/LBP solution (the concentration of LPS was about 0.6 ng/mL and the concentration of LBP was about 0.3 nM). Subsequently, rsCD14-ST (PSP64) or rsCD14 (1-356) was diluted with 0.01% BSA/PBS to a desired concentration and then mixed with the LPS/LBP solution in equivalent amounts. After a reaction at 37° C. for one hour, Endospecy™ C lysate (Endospecy™-ES-24S set; Seikagaku Corporation) was added and then the whole was left to stand at room temperature for 20 minutes. After that, 25% acetic acid was added to the mixture to terminate the reaction. Then, the absorbance at 405 nm was determined to calculate the concentration of LPS in the reaction solution (hereinafter, referred to as a free-LPS concentration). Furthermore, an calibration curve was formed by carrying out the similar operation as that of the sample after only subjecting the LPS diluent to a reaction at 37° C. for one hour. As a result, for rCD14 (1-356), a decrease in amount of free LPS depended on the concentration of rCD14 (1-356) added and the binding between rCD14 (1-356) and LPS was then confirmed. However, for rsCD14-ST (PSP64), even if it was added up to 100 nM, the amount of free LPS was not changed. It is found that rsCD14-ST (PSP64) has no LPS binding ability.

Example 16

Figure 11:
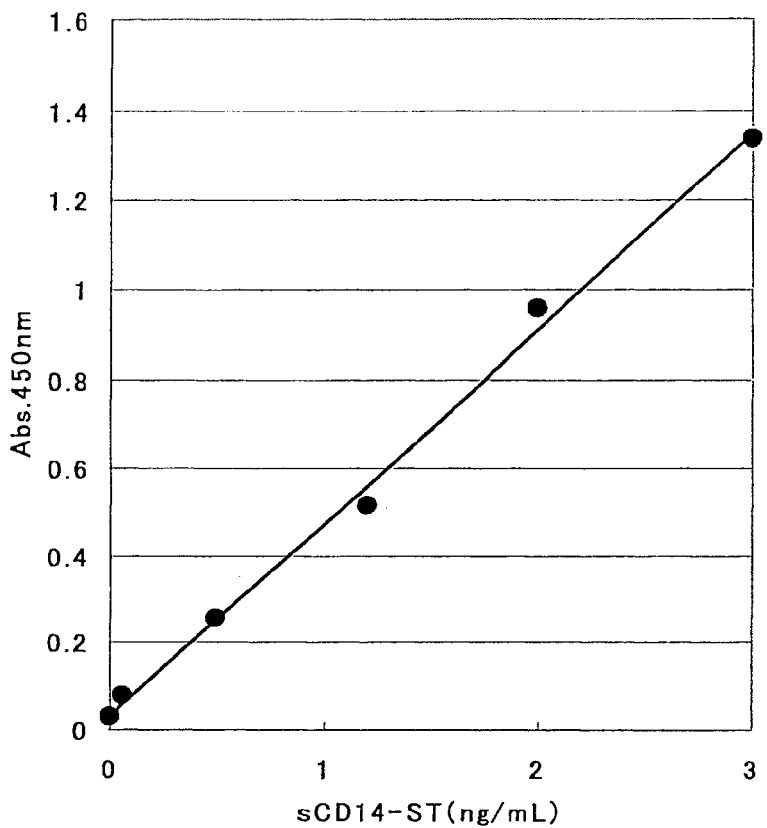
FIG. 11 shows the standard curve for the EIA kit of Example 16 using rsCD14-ST(2ST64).

Examination of rsCD14-ST Standard Preparation 16-(1) Creation of Standard Curve Based on rsCD14-ST Standard Preparation A standard curve was created using rsCD14-ST(2ST64) prepared in Example 13-(3)-3. That is, rsCD14-ST (2ST64) was diluted with a diluent described in Example 7-(12) to prepare a concentration series of 0.06, 0.5, 1.2, 2, and 3 ng/ml, and the measurement was then carried out using the kit of Example 7-(1). A diluent was used as a blank. As shown in FIG. 11, the absorbance increases as the concentration increases. Thus, it was confirmed that rsCD14-ST (2ST64) can be used as a standard preparation of the kit.

16-(1) Creation of Standard Curve Based on rsCD14-ST Standard Preparation sCD14-ST in the normal human serum and sCD14-ST in the EDTA-containing serum were measured using the kit prepared in Example 7-(3). In the EDTA-containing serum, the concentration of sCD14-ST was about twice as high as that in serum. This is because EDTA may affect the assay system. Thus, when EDTA was added to the diluent so as to have a concentration of 0.2 mg/ml, the measurement value of serum increased, resulting in no difference from the EDTA-containing serum. However, a decrease in reactivity was observed for a standard curve created using a rsCD14 (1-307) S286C standard preparation. It is found that the presence or absence of EDTA affects the reading value. On the other hand, when rsCD14-ST is used as a standard preparation, the addition of EDTA does not affect the standard curve. Consequently, it was determined that rsCD14-ST is more preferable for the standard preparation.

Example 17

Preparation of Antibody Using rsCD14-ST 17-(1) Preparation of Polyclonal Antibody Specific to rsCD14-ST For preparing polyclonal antibody to rsCD14-ST(PSP64) prepared in Example 13-(3)-3, a rabbit was immunized. That is, 20 µg of rsCD14-ST(PSP64) was diluted with 500 µl of physiological saline and then mixed with 500 µL of Freund's complete adjuvant (DIFCO) in equivalent amounts, followed by subcutaneously administering the mixture to the back of New Zealand white female rabbit (Kitayama Labes) weighing 2.0 to 2.4 kg. After 2 weeks, 20 µg of rsCD14-ST (PSP64) was diluted with 500 µl of physiological saline and the solution was mixed with 500 µl of Freund's incomplete adjuvant (DIFCO) in equivalent amounts, followed by subcutaneously administering the mixture to the back. After additional two weeks, 20 µg of rsCD14-ST (PSP64) was administered in the same way. After one week from the administration, blood was collected from the ear vein and antiserum was then isolated from the blood by the conventional method, followed by purification of antibody. At first, ammonium sulfate was added to the antiserum such that the final saturated concentration of ammonium sulfate would reach 33% and then stirred at 4° C. for one hour, followed by centrifuging a precipitated pellet. Subsequently, the precipitate was dissolved in a Dulbecco PBS (hereinafter, referred to as PBS (PH 7.4)) and then dialyzed overnight. The dialysate was filtered and then applied to Protein A column (Procep-A™, Millipore). The IgG fraction coupled thereon was eluted with a 0.1-M glycine hydrochloride buffer (pH 3.0), resulting in purified antibody. Then, the antibody was dialyzed against PBS (pH 7.4) and the protein concentration was then calculated from the absorbance at 280 nm (absorption coefficient: 0.714 mg/ml). Hereinafter, the resulting antibody will be referred to as anti-PSP64 polyclonal antibody or anti-PSP64 antibody.

17-(2) Preparation of Monoclonal Antibody Specific to sCD14-ST

For enhancing antigenicity, dinitrofluorobenzene (Wako Pure Chemical Industries, Ltd.) was added to rsCD14-ST (PSP64) prepared in Example 13-(3)-3 so as to have a final concentration of 0.1% and then the whole was incubated at room temperature for one hour, followed by dialysis with PBS (PH 7.4), resulting in antigen to be administered (hereinafter, also referred to as DNP-PSP64 antigen). Then, 30 µg of the DNP-PSP64 antigen was dissolved in 100 µl of physiological saline and then the solution was mixed with an equal amount of Freund's complete adjuvant (DIFCO), followed by administering 100 µl of antigen to the sole of each hind foot-pad of an 8-week female Wistar rat. After two weeks, the iliac lymph node was excised and cell fusion was then carried out. The cell fusion was conducted according to Tamie Ando and Takeshi Chiba: "Introduction to Monoclonal Antibody Experimental Manipulation", page 83, 1991 (Kodansha Ltd.). In other words, lymphocytes were separated from the lymph node using a cell strainer (Falcon) and mixed with myeloma cells (Sp2/O-Ag14) at a ratio of 5:1, followed by cell fusion using polyethylene glycol. Fused cells were suspended in an HAT medium and hybridomas were selected, followed by screening hybridomas producing the target antibody.

The screening was performed by an ELISA method in which rsCD14-ST(PSP64) was directly immobilized on a plate. That is, 50 µl of rsCD14-ST(PSP64) diluted with 0.1-M phosphate buffer (pH 7.4) to 2.5 µg/mL was added to each well of an immunoplate (Maxisorb™, NUNC) and left to stand at 4° C. overnight. After that, the plate was washed with ion-exchanged water five times and then 100 µl of PBS (pH 7.4) containing 2% StabilGuard (SurModics, Inc.) was added to each well, followed by leaving the plate standing for 1 hour at room temperature to effect blocking. Then, the culture supernatant sampled from the selected hybridomas was added to each well and allowed to react at 37° C. for 1 hour. After that, the plate was washed three times with physiological saline containing 0.05% Tween 20. Subsequently, 50 µl of a solution obtained by diluting peroxidase-labeled anti-rat immunoglobulin antibody (DAKO) 1,000-fold with PBS (pH 7.4) containing 10% rabbit serum was added to each well. After a reaction at 37° C. for 1 hour, the plate was washed five times in the same manner as above and a tetramethylbenzidine solution (TMB, BioFix) was added to each well. After a reaction for 10 minutes at room temperature, the reaction was terminated with a 0.5 M sulfuric acid solution and an absorbance at 450 nm was determined using a plate spectrophotometer (Multiscan JX, Thermo Electron Corporation). As a result, a well containing hybridoma capable of producing an antibody binding to 2ST64 protein was selected. Next, from the selected well, cloning was performed by a limiting dilution method according to Tamie Ando and Takeshi Chiba: "Introduction to Monoclonal Antibody Experimental Manipulation", page 97, 1991 (Kodansha Ltd.). After 10 days, likewise, screening was performed using as an index the reactivity with 2ST64 protein and 6 kinds of hybridomas were selected. The selected hybridomas were cultivated in a 10% FCS/RPMI-1640 medium (Sigma) and then cultivated in Hybridoma-SFM medium (Invitrogen) to produce an antibody. The antibody was purified using a protein G column (Prosep-G column, Millipore). The subtypes of the purified F1237-3-4 antibody and F1237-4-4 antibody were determined using a rat typing kit (ZYMED) and as a result these subtypes were rat IgG2a·κ and rat IgG2b·κ.

17-(3) Preparation of anti-rsCD14-ST Polyclonal Antibody Specific to rsCD14-ST without Binding to High Molecular Weight CD14

For preparing polyclonal antibody specifically binding to sCD14-ST found in patients suffering from sepsis but not to high molecular weight CD14, a rabbit is immunized with rCD14-ST (PSP64) prepared in Example 13-(3)-3. That is, 20 µg of rsCD14-ST(PSP64) is diluted with 500 µl of physiological saline and then mixed with 500 µl of Freund's complete adjuvant (DIFCO) in equivalent amounts, followed by subcutaneously administering the mixture to the back of New Zealand white female rabbit (Kitayama Labes) weighing 2.0 to 2.4 kg. After 2 weeks, 20 µg of rsCD14-ST (PSP64) is diluted with 500 µl of physiological saline and the solution is mixed with 500 µl of Freund's incomplete adjuvant (DIFCO) in equivalent amounts, followed by subcutaneously administering the mixture to the back. After additional two weeks, 20 µg of rsCD14-ST (PSP64) is administered in the same way. After one week from the administration, blood is collected from the ear vein and antiserum is then isolated from the blood by the conventional method, followed by purification of antibody. At first, ammonium sulfate is added to the antiserum such that the final saturated concentration of ammonium sulfate would reach 33% and then stirred at 4° C. for one hour, followed by centrifuging a precipitated pellet. Subsequently, the precipitate is dissolved in a Dulbecco PBS (hereinafter, referred to as PBS (PH 7.4)) and then dialyzed overnight. The dialysate is filtered and then applied to Protein A column (Procep-A™, Millipore). The IgG fraction coupled thereon is eluted with a 0.1-M glycine hydrochloride buffer (pH 3.0), resulting in purified antibody. After dialysis with PBS (pH 7.4), the protein concentration is calculated from the absorbance at 280 nm (absorption coefficient: 0.714 mg/ml). The resulting purified anti-PSP64 polyclonal antibody is specifically purified using a resin coupled with high molecular weight CD14 prepared in Example 22 or with rsCD14(1-356) prepared in Example 6 to obtain antibody capable of binding only to rsCD14-ST. That is, according to the manual, 5 mg of high molecular weight CD14 or rsCD14 (1-356) is coupled with the HiTrap™ NHS-activated HP column (Amersham Biosciences) to prepare an affinity column for specific purification. Next, the antibody purified by the protein A column is applied to the affinity column for specific purification, while the antibody not capable of binding to high molecular weight CD14 or rsCD14 (1-356) is collected. The resulting antibody is condensed. After dialysis with PBS (pH 7.4), the protein concentration is calculated from the absorbance at 280 nm (absorption coefficient: 0.714 mg/ml).

17-(4) Preparation of Anti-rsCD14-ST Monoclonal Antibody Specific to rsCD14-ST, which does not Bind to High Molecular Weight CD14

For enhancing antigenicity, dinitrofluorobenzene (Wako Pure Chemical Industries, Ltd.) is added to rsCD14-ST (PSP64) prepared in Example 13-(3)-3 so as to have a final concentration of 0.1% and then the whole is incubated at room temperature for one hour, followed by dialysis with PBS (PH 7.4), resulting in antigen to be administered (hereinafter, also referred to as DNP-PSP64 antigen). Then, 30 µg of the DNP-PSP64 antigen is dissolved in 100 µl of physiological saline and then the solution is mixed with an equal amount of Freund's complete adjuvant (DIFCO), followed by administering 100 µl of antigen to the sole of each hind foot-pad of an 8-week female Wistar rat or ddY mouse. After two weeks, the iliac lymph node is excised and cell fusion is then carried out. The cell fusion is conducted according to Tamie Ando and Takeshi Chiba: "Introduction to Monoclonal Antibody Experimental Manipulation", page 83, 1991 (Kodansha Ltd.). In other words, lymphocytes are separated from the lymph node using a cell strainer (Falcon) and mixed with myeloma cells (Sp2/O-Ag14) at a ratio of 5:1, followed by cell fusion using polyethylene glycol. Fused cells are suspended in an HAT medium and hybridomas are selected, followed by screening hybridomas producing the target antibody.

The screening is performed by an ELISA method in which rsCD14-ST(PSP64), high molecular weight CD14 or rsCD14 (1-356) is directly immobilized on a plate. That is, 50 µl of rsCD14-ST(PSP64), high molecular weight CD14, or rsCD14 (1-356) diluted with PBS (pH 7.4) to 2.5 µg/mL is added to each well of an immunoplate (Maxisorb™, NUNC) and left to stand at 4° C. overnight. After that, the plate is washed with ion-exchanged water five times and then 100 µl of PBS (pH 7.4) containing 2% StabilGuard™ (SurModics, Inc.) is added to each well, followed by leaving the plate standing for 1 hour at room temperature to effect blocking. Then, the culture supernatant sampled from the selected hybridomas is added to each well and allowed to react at 37° C. for 1 hour. After that, the plate is washed three times with physiological saline containing 0.05% Tween 20. Subsequently, 50 µl of a solution obtained by diluting peroxidase-labeled anti-rat immunoglobulin antibody (DAKO) or peroxidase-labeled anti-mouse immunoglobulin antibody (DAKO) 1,000-fold with PBS (pH 7.4) containing 10% rabbit serum is added to each well. After a reaction at 37° C. for 1 hour, the plate is washed five times in the same manner as above and a tetramethylbenzidine solution (TMB, BioFix) is added to each well. After a reaction for 10 minutes at room temperature, the reaction is terminated with a 0.5 M sulfuric acid solution and an absorbance at 450 nm is determined using a plate spectrophotometer (Multiscan JX™, Thermo Electron Corporation). As a result, a well containing hybridoma capable of producing an antibody binding to rsCD14-ST but not to high molecular weight CD14 or rsCD14 (1-356) is selected. Next, from the selected well, cloning is performed by a limiting dilution method according to Tamie Ando and Takeshi Chiba: "Introduction to Monoclonal Antibody Experimental Manipulation", page 97, 1991 (Kodansha Ltd.). After 10 days, screening is performed likewise using as an index the reactivity with 2ST64 protein and a hybridoma is selected. The selected hybridoma is cultivated in a 10% FCS/RPMI-1640 medium (Sigma) and then cultivated in Hybridoma-SFM medium (Invitrogen) to produce an antibody. The antibody is purified using a protein G column (Prosep-G™ column, Millipore) or a protein A column (Prosep-A™, Millipore). After dialysis with PBS (pH 7.4), the protein concentration is calculated from the absorbance at 280 nm (absorption coefficient: 0.714 mg/ml). The subtype of the purified antibody is determined using a commercially available kit.
17-(5) Selection of Anti-rsCD14-ST Monoclonal Antibody Specific to sCD14-ST, which does not Depend on Method of Storing Sample Monoclonal antibody for the kit where the state of preservation does not affect the results of measurement is obtained. That is, sCD14-ST is determined as antibody on the label side in a sandwich system described in Example 22 among monoclonal antibodies against rsCD14-ST prepared in Example 17-(4). After the antibody having property of increasing in a patient suffering from sepsis has been selected, sCD14-ST in the sample is determined. The measurement is conducted on both the sample stored in a frozen state and the sample stored at room temperature for 24 hours and then a combination of antibodies with a little difference between their measured values was selected.

Example 18

Reactivity of Anti-sCD14-ST(PSP64) Polyclonal Antibody

Figure 12:
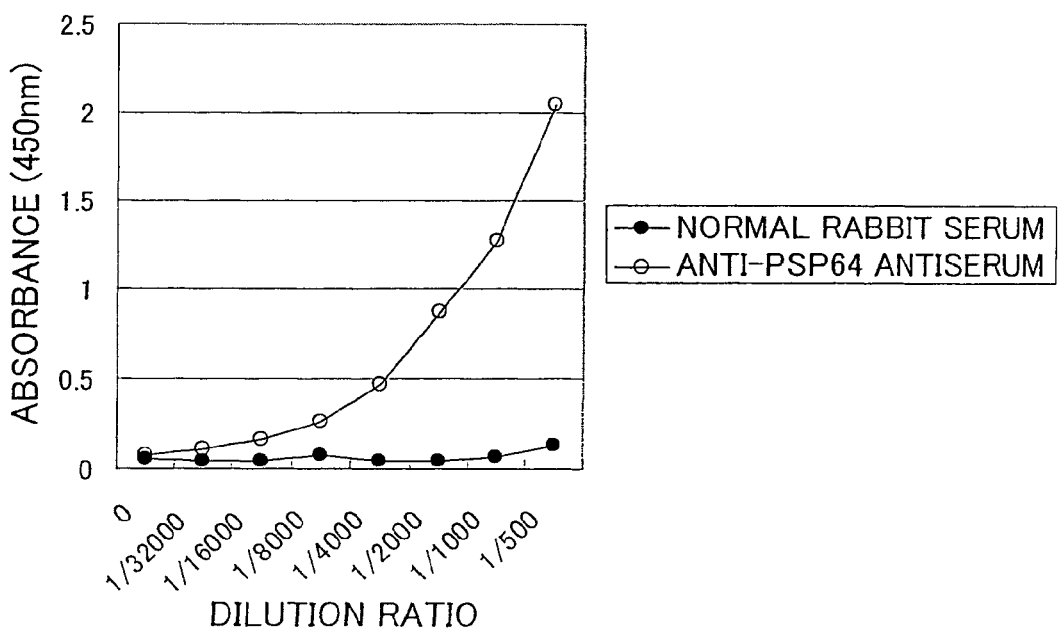
FIG. 12 is a view comparing the antibody titer of the antiserum of the rabbit administered with rsCD14-ST (PSP64) with that of the serum from a normal rabbit.

The reactivity of anti-PSP64 polyclonal antibody prepared in Example 17-(1) was confirmed. Just as in the case of Example 17-(2), rsCD14-ST (PSP64) was immobilized. Antiserum containing anti-PSP64 polyclonal antibody prepared in Example 17-(1) and normal rabbit serum as a control were diluted 500 times with PBS (pH 7.4) and then serially diluted up to 32,000 times to prepare their serial dilutions, respectively. Each diluent was added to each well after blocking and then reacted at 37° C. for one hour, followed by washing three times with physiological saline containing 0.05% Tween 20. Subsequently, 50 μl of a solution in which peroxidase-labeled anti-rabbit immunoglobulin antibody (DAKO) was diluted 1,000 times with PBS (pH 7.4) containing 10% goat serum was added to each well. After the reaction at 37° C. for one hour, the well was washed five times in the same way as above and a tetramethylbenzidine solution (TMB, BIoFIx) was added to each well. After a reaction for 10 minutes at room temperature, the reaction was terminated with a 0.5 M sulfuric acid solution and an absorbance at 450 nm was determined using a plate spectrophotometer (Multi-Scan JX™, Thermo Electron Corporation) to confirm the binding to rsCD14-ST (PSP64). As shown in FIG. 12, the rabbit administered with rsCD14-ST (PSP64) showed an increase in absorbance depending on the dilution ratio, while the normal rabbit serum did not show such an increase and the production of antibody specific to rsCD14-ST (PSP64) protein was then confirmed.

Example 19

Preparation of sCD-14-ST Assay System Using Anti-rsCD14-ST Antibody

Figure 13:
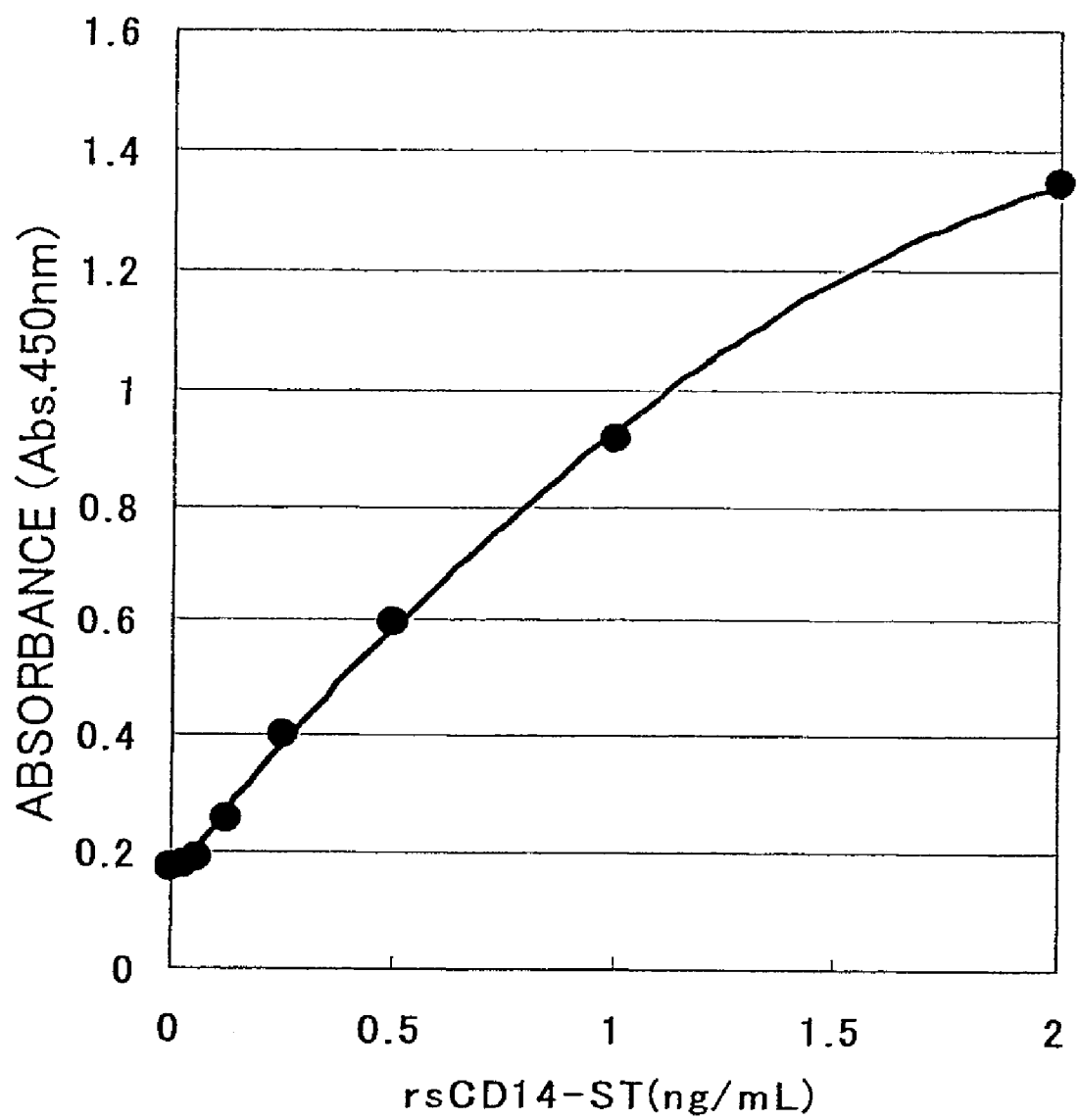
FIG. 13 shows the standard curve for the EIA system of Example 19 using rsCD14-ST(2ST64).

S68-peptide polyclonal antibody was diluted to 10 μg/ml with D-PBS (pH 7.4) and 50 μl of the resultant solution was then added to each well of an immunoplate (Maxisorb, NUNC). After a reaction at 4° C. overnight, the plate was washed five times with ion-exchanged water and blocked by the addition of 100 μl of D-PBS containing 0.1% Stabil-Guard™ (SurModics, Inc.) and 0.1% Tween 20 to each well. Next, 76 mM PBS (pH 7.4) containing 1% CD14-absorbing serum and 0.1% BSA was used as a diluent to prepare a dilution series of 0, 0.031, 0.063, 0.125, 0.25, 0.5, and 1.2 ng/ml of rsCD14-ST (2ST64) protein standard preparation. The dilution series of the standard preparation was added in an amount of 50 μl per well and reacted for two hours at 37° C. After the completion of the reaction, the plate was washed three times with physiological saline containing 0.05% Tween 20. Then, 50 μL of a 1% fetal bovine serum/Hybridoma-SFM solution containing F1237-3-4 antibody was added to each well. After a reaction at 37° C. for one hour, the plate was washed three times in the same way as above and 50 μl of a peroxidase-labeled anti-rat immunoglobulin antibody (DAKO) which was diluted to the concentration of 1/1,000 with D-PBS (pH 7.4) containing 10% rabbit serum was added to each well. After a reaction at 37° C. for one hour, the plate was washed five times in the same way as above and a tetramethylbenzidine solution (TMB, BioFix) was added to each well. After a reaction for 10 minutes at room temperature, the reaction was terminated by a 0.5 M sulfuric acid solution and an absorbance at 450 nm was determined using a plate spectrophotometer (MaltiScan JX™, Thermo Electron Corporation). A standard curve prepared was shown in FIG. 13.

Example 20

Serum Assay with Novel sCD14-ST Assay System

The sandwich EIA system prepared in Example 19 was used to determine the sera of five normal donors and five patients suffering from sepsis. As a result, as shown in Table 10, the concentration of sCD14-ST in the serum of normal donor was 1 ng/ml while that of the septic patient was 6.47 ng/ml, which was almost six times as high as the former. Therefore, just as in the case of Example 11, the patients suffering from sepsis could be diagnosed. Furthermore, the concentrations were different from those in Example 11 and the difference was due to the difference in standard preparations as described in Example 16.

TABLE 10

| Sample No. | Classification | Concentration (ng/ml) |
|---|---|---|
| N1 | Normal | 0 |
| N2 | Normal | 1.7 |
| N3 | Normal | 0.76 |
| N4 | Normal | 3.16 |

TABLE 10-continued

| Sample No. | Classification | Concentration (ng/ml) |
|---|---|---|
| N5 | Normal | 0 |
| S1 | Sepsis | 8.44 |
| S2 | Sepsis | 5.02 |
| S3 | Sepsis | 9.02 |
| S4 | Sepsis | 4.26 |
| S5 | Sepsis | 5.6 |

Example 21

Evaluation of Monoclonal Antibody Specific to sCD14-ST Protein

For clarifying the specificity of antibody to sCD14-ST, the affinity of antibody to each of various CD14 proteins was determined. In addition, the reactivity of antibody to each of various antigens was determined by an antigen immobilized EIA system.

21-(1) Measurement of Dissociation Constant ($K_D$) Using BIACORE

The reaction rate constants of F1237-3-4 antibody prepared in Example 17-(2) and 3C10 antibody (ATCC TIB-228) which is anti-CD14 antibody, were analyzed using Biacore™ 3000 (Biacore). First, rsCD14-ST (2ST64) and rsCD14 (1-356) were separately immobilized on a sensor chip CM5 (Biacore) using an amine-coupling kit (Biacore). An assay was performed such that HBS-EP (Biacore) was used as a running buffer and a dilution series (1.25 nM to 640 nM, which could be changed depending on antibody) of each antibody was injected into flow cells. The data analysis was performed using BIA evaluation software version 4.1 (Biacore) by subtracting reference-cell data from flow-cell measurement data of each antigen being immobilized and also by subtracting only measurement data of the running buffer. As a result of analyzing a dissociation constant ($K_D$) using the Bivalent analysis, as shown in FIG. 11 the F1237-3-4 antibody showed high affinity to rsCD14-ST, but KD thereof could not be calculated because of no substantial binding to rsCD14 (1-356). 3C10 could not substantially bind to rsCD14-ST and showed high affinity to rsCD14 (1-356).

TABLE 11

| Name of antibody | Dissociation constant KD (M) | |
|---|---|---|
| | rsCD14-ST | rsCD14 (1-356) |
| F1237-3-4 antibody | $5.75 \times 10^{-8}$ | unavailable |
| 3C10 antibody | unavailable | $6.69 \times 10^{-10}$ |

21-(2) Analysis of Antigenic Specificity Using Antigen Immobilized EIA System

The reactivities of F1237-3-4 antibody prepared in Example 17-(2) and 3C10 antibody (which is anti-CD14 antibody) to high molecular weight CD14 are analyzed using the antigen immobilized EIA system. That is, high molecular weight CD14 prepared by the same way as that of Example 13-(2) is diluted to 2.5 µg/ml with D-PBS (pH7.4). Then, 50 µL of the resultant solution is added to each well of an immunoplate (Maxisorb™, NUNC) and subsequently left to stand at 4° C. overnight. Next, the plate is washed five times with ion-exchanged water and blocked by the addition of 100 µL of PBS (pH 7.4) containing 2% StabilGuard™ (SurModics, Inc.) to each well. Each of F1237-3-4 antibody and 3C10 antibody is diluted to 1 µg/mL with PBS (pH 7.4). Then, the resultant solution is added to each well and allowed to react at 37° C. for one hour, followed by washing three times with physiological saline containing 0.05% Tween 20. Subsequently, a solution is prepared by diluting peroxidase-labeled anti-immunoglobulin antibody (DAKO) to each of the antibodies 1,000 times with PBS (pH 7.4) containing 10% serum and 50 µL of the resultant solution is then added to each well. After a reaction at 37° C. for one hour, the plate is washed five times in the same way as above and a tetramethylbenzidine solution (TMB, BioFix) is added to each well. After a reaction for 10 minutes at room temperature, the reaction is terminated by a 0.5 M sulfuric acid solution and an absorbance at 450 nm is determined using a plate spectrophotometer (Multi-Scan JX™ Thermo Electron Corporation). As a result, it is confirmed that 3C10 strongly binds to high molecular weight CD14, while F1237-3-4 antibody cannot bind, substantially.

Example 22

Preparation (2) of sCD14-ST Assay System Using Anti-rsCD14-ST Antibody 22-(1) Sandwich EIA Method Sandwich EIA systems were prepared by various combinations of antibodies listed in Table 12 according to the method described in Example 3-(3). As shown in Table 12, any of sCD14 assay systems using the monoclonal antibodies prepared in Example 17 specifically increased in patients suffering from sepsis but not in normal donors.

TABLE 12

| Combination of antibodies | | Measured values | |
|---|---|---|---|
| Immobilizing side | Labeling side | Sepsis patients | Normal donors |
| S68 peptide polyclonal antibody | F1237-3-4 antibody | + | − |
| S68 peptide polyclonal antibody | F1237-4-4 antibody | + | − |

22-(2) Competitive EIA Method

F1237-3-4 antibody diluted to 10 µg/mL with PBS is added to each well and then left to stand at 4° C. overnight thereby to bind each other. Subsequently, it is blocked with 2% StabilGuard/PBS (pH 7.4). After that, 25 µL of each of the sera from the sepsis patient and the normal donor is added to the plate and subsequently peroxidase-labeled rsCD14-ST antigen diluted to 0.5 µg/mL with PBS (pH 7.4) containing 1% BSA and 0.1% Tween 20 is added. After the reaction at 37° C. for one hour, each of the wells in the plate is washed three times with physiological saline containing 0.05% Tween 20. A TMB solution (BioFix) is added to the well to allow color development, followed by the termination of such a reaction with a 0.5-M aqueous solution of sulfuric acid. In addition, an absorbance at 450 nm is determined. A decrease in absorbance depends on the concentration of sCD14-ST in blood. Thus, the measured value reflects the amount of sCD14-ST in blood. It is confirmed that normal donors have lower concentrations of sCD14-ST, while the concentrations of the patients suffering from sepsis are specifically high. Furthermore, the labeling materials to be used include other enzymes, radio-

Example 23

Antibody Screening for Assaying Soluble Protein in Blood

For the purpose of preparing an assay system of soluble protein in blood, purified and identified in Example 9, two different screening methods useful for the assay were constructed.

23-(1) Preparation of Antibodies for Screening

Antibodies for screening bound to any peptide having consecutive 6 to 20 amino acid residues selected from amino acid sequences described in SEQ ID NO: 3 can be prepared according the description of Example 1. Alternatively, the antibodies can be prepared as follows: (i) a peptide is synthesized by the conventional method on the basis of the whole sequence of CD14 and immunizing antigen is then prepared to form antigen; (ii) purified soluble CD14 antigen in serum is purified and then used as immunogen to form antibody; (iii) recombinant CD14 protein is prepared using COS cells or E. coli and then used as immunogen to form antibody; and (iv) various prepared CD14 antigens are subjected to thermal denaturalization and DNP-ation or the like and then used as immunogens to form antibodies.

For instance, P001 antibody (antibody prepared using a peptide consisting of amino acid residues described in SEQ ID NO: 4 as antigen) and P002 antibody (antibody prepared using a peptide consisting of amino acid residues described in SEQ ID NO: 5 as antigen) are prepared by the method described in Example 1 and then attached to carrier proteins, followed by administration to prepare antibodies, respectively. Furthermore, S68 antibody prepared in Example 1-(4), F1146-17-2 antibody prepared in Example 2, F1031-8-3 antibody prepared in Example 3-(2)[2], F1106-13-3 antibody prepared in Example 3-(2)[1], F1237-3-4 antibody prepared in Example 17-(2), and anti-PSP64 antibody prepared in Example 17-(1) were also prepared as samples for screening, respectively. As described above, antibodies bound to peptides each consisting of consecutive 6 to 20 amino acid resides selected from amino acid sequences described in SEQ ID NO: 3 were used to screen for an antibody capable of specifically detecting soluble protein in blood according the procedures described below.

23-(2) Antigen Immobilization

This is a screening method for an antibody for use in assaying soluble protein in blood, which is characterized by the use of the difference in reactivity of the antibody to the high molecular weight CD14 protein derived from a normal donor. In the screening method, the reactivity to the high molecular weight CD14 protein is analyzed by antigen immobilization, whereby screening is conducted for an antibody which cannot bind to the high molecular weight CD14 in serum of the normal donor but binds to the soluble protein in blood.

[1] Preparation of High Molecular Weight CD14

At first, high molecular weight CD14 protein was prepared as follows. Human serum (Nippon Biotest Laboratories inc.) was applied to 3C10 antibody-binding resin column (5 mL) and then washed with PBS, followed by elution with a 6-M urea aqueous solution. The eluate was dialyzed against PBS and then freeze-dried, followed by fractionation with gel filtration chromatography (Superdex75 10/300GL, Amersham Biosciences). Each of the resulting fractions was analyzed using the commercially-available soluble CD14 protein assay kit (IBL-kit) and the high molecular weight CD14 fraction capable of reacting with the IBL-kit was then pooled and freeze-dried. The freeze-dried product was dissolved and subjected again to the measurement with the IBL kit to calculate the concentration thereof.

[2] Antigen Immobilized EIA Method

An antigen immobilized EIA method was carried out as follows. First, 2.5 µg/mL of high molecular weight CD14 was placed in each well of the plate and left standing at 4° C. overnight for binding. Then, it was blocked by 2% Stabil-Guard/PBS (pH 7.4) and 1 µg/mL of each antibody was diluted with PBS and then added to each of wells where the respective antigens were immobilized. After a reaction at 37° C. for one hour, the well was washed three times with physiological saline containing 0.05% Tween 20. Subsequently, peroxidase-labeled anti-γ-globulin antibody (DAKKO) to each antibody was diluted with PBS (pH 7.4) containing 10% rabbit serum and 0.05% Tween 20 and allowed to react at room temperature for one hour. Likewise, the well was washed five times and then a TMB solution (BioFix) was added to the well for color development, followed by the termination of the reaction with a 0.5-M sulfuric acid aqueous solution. Subsequently, the absorbance of the antibody was measured at 450 nm. For the high molecular weight CD14, an antibody causing no increase in absorbance was selected. F1237-3-4 antibody was selected according to the above method.

Instead of the antibody to be bound to the plate, sCD14-ST may be bound to the plate to permit the selection of an antibody that does not bind to sCD14-ST.

Next, dot blotting is carried out as follows. First, high molecular weight CD14 is spotted on the Trans-Blot Transfer Medium™ (Bio-Rad Laboratories, Inc.) at 400 ng/dot and then dried. Subsequently, it is blocked using 100% Block-Ace™ (Snow Brand Milk Products Co., Ltd.). Two types of immobilizing CD14, and each of various anti-CD14 antibodies diluted with PBS (pH 7.4) containing 10% Block-Ace™, 0.05% Tween 20 is allowed to react at room temperature for one hour. Next, the medium is washed five times for five minutes with PBS (pH 7.4) containing 0.05% Tween 20. Subsequently, peroxidase-labeled anti-rabbit immunoglobulin antibody (DAKKO, P448) is diluted with PBS (pH 7.4) containing 10% Block-Ace™ and 0.05% Tween 20, followed by reacting with each membrane at room temperature for one hour. Likewise, it is washed five times and the presence or absence of the binding of antibody is determined as luminescence in a chemiluminescence detector (CoolSaver™ AE-6955, ATTO corporation) by means of ECL-PLUS™ (Amersham Biosciences). For the high molecular weight CD14 used for the screening, antibody of which no spot could be detected is selected.

23-(3) Sandwich Immunoassay

This is a screening method for an antibody for use in assaying soluble protein in blood, which is characterized by the use of difference between the detected amounts of the sera of normal donors and patients suffering from sepsis. A sandwich ELISA system is prepared by combining two different anti-CD14 antibodies and then used to assay normal donors and patients suffering from sepsis.

[1] Preparation of Peroxidase-Labeled Antibody

A peroxidase-labeled antibody was prepared according to the description of Example 3-(3) using the antibody prepared in 12-(1).

[2] Preparation of Sandwich EIA System

Each antibody for screening was diluted to 10 µg/mL with D-PBS (pH 7.4) and 50 µL of the resultant solution was then added to each well of an immunoplate (Maxisorb™, NUNC).

After a reaction at 4° C. overnight, the well was washed with ion-exchanged water five times and 100 μL of D-PBS containing 2% StabilGuard™ (SurModics, Inc) was added to each well to effect blocking. Using as a diluent PBS (pH 7.4) containing 0.1% BSA, a dilution series of S286C protein standard preparation of 0, 3.12, 6.25, 12.5, 25, 50, 100, and 200 ng/ml and a 10-time diluted sample were prepared. Then, 50 μL of each of the dilution series and the diluted sample were added to each well and then reacted at 37° C. for one hour. After the termination of the reaction, the well was washed three times with physiological saline containing 0.05% Tween 20. Subsequently, peroxidase-labeled antibody was diluted to 1 μg/mL with PBS containing 2% rat serum, 1% mouse serum, and 0.1% Tween 20 and 50 μL of the resultant solution was then added to each well. After a reaction at 37° C. for one hour, the well was washed five times in the same way as above and a tetramethylbenzidine solution (TMB, BioFix) was added to each well. After a reaction for 20 minutes at room temperature, the reaction was terminated by a 0.5 M sulfuric acid solution and an absorbance at 450 nm was measured using a plate spectrophotometer (NJ-2100, Japan Intermed).

[3] Screening of Antibody Using Sandwich EIA System

With respect to a combination allowing the system to form a standard curve, screening was carried out for determining whether soluble protein in blood could be specifically detected. Sera obtained from two sepsis patients and two normal donors were subjected to the measurement in the assay system prepared in [1]. Screening was conducted for a combination of antibodies capable of specifically detecting sepsis patients by selecting a combination of antibodies in the assay system which shows higher levels in the sepsis patients but lower levels in the normal donors. As a result, combinations of antibodies described in Examples 7-(1) to (8) and Example 22 were selected. Furthermore, a measurement value of high molecular weight CD14 in each serum may be obtained by the IBL kit in advance and then a combination of antibodies of the assay system that does not determine the high molecular weight CD14 may be selected.

Example 24

Method of Screening Antibodies Using rsCD24-ST

Two different methods were investigated for screening antibodies using rsCD14-ST.

24-(1) Antigen Immobilized EIA Method

As a method of screening for an antibody capable of specifically detecting sCD14-ST, the antibody-screening method described in Example 17-(2) (i.e., a method utilizing ELISA in which rsCD14-ST (PSP64) is directly immobilized on a plate) was conducted.

The results of screening various antibodies are shown in Table 13. Here, MY4 (Colter), MEM18 (Monosan), 61D3 (Southern Biotechnology Associates, Inc.), and various kinds of γ-globulin used herein were commercially available.

TABLE 13

| Antibody | Binding to rsCD14-ST (PSP64) |
| --- | --- |
| F1237-3-4 | ++ |
| S68 | ++ |
| F1106-13-3 | ++ |
| F1031-8-3 | ++ |
| P001 | + |
| P002 | ++ |

TABLE 13-continued

| Antibody | Binding to rsCD14-ST (PSP64) |
| --- | --- |
| MY4 | − |
| 3C10 | − |
| MEM18 | − |
| 61D3 | − |
| Mouse γ-globulin | − |
| Rat γ-globulin | − |
| Rabbit γ-globulin | − |

24-(2) Sandwich EIA Method

The sandwich EIA system described in Example 23-(2) was prepared for the method of screening for an antibody capable of specifically detecting sCD14-ST. That is, various antibodies to be provided as target samples of screening were immobilized on a plate and the screening was then carried out by the sandwich ELISA method using peroxidase-labeled F1106-13-3 antibody or peroxidase-labeled F1031-8-3 antibody and using rsCD14-ST (PSP64) for the antigen.

The results of screening various antibodies are shown in Table 14. Here, AntiHCG antibody used was commercially available.

TABLE 14

| Antibody | Binding to rsCD14-ST (PSP64) |
| --- | --- |
| F1237-3-4 | ++ |
| S68 | ++ |
| F1106-13-3 | − |
| F1031-8-3 | − |
| P001 | + |
| P002 | + |
| 3C10 | − |
| 61D3 | − |
| AntiHCG antibody | − |
| Rat γ-globulin | − |
| Rabbit γ-globulin | − |

Example 25

Chemical Synthesis of sCD14-ST

A soluble polypeptide having amino acids at positions 1 to 70 on the N-terminal of human CD14 was chemically synthesized (hereinafter, referred to as sCD14(1-70)).

A peptide synthesizer ABI433A (Applied) was used and amino acid columns were then aligned according to the amino acid sequences to carry out automatic synthesis. The synthesized peptide was removed from a resin by the conventional method and then recovered by ether precipitation. The resultant peptide was re-dissolved in distilled water and then freeze-dried. After the dissolution, the crude peptide thus obtained was eluted through a linear gradient of 5-70% acetonitrile by the use of C18 reversed phase HPLC (CAPCELL-PAK, Shiseido Co., Ltd.). Consequently, a fraction containing a peptide of interest was collected. The collected fraction was freeze-dried and provided as a purified peptide. The purified peptide was dissolved in the diluent described in Example 7-(12) and then the solution was subjected to the measurement with the kit described in Example 7-(3). As a result, the purified peptide strongly reacted with the kit described in Example 7-(3), so that sCD14-ST chemically prepared could be also provided as a standard preparation.

Example 26

Measurement on sCD14-ST Expressed from THP-1 Cells Treated with Elastase

THP-1 cells ($1 \times 10^6$ cells) stimulated with vitamin D3 were suspended in RPMI1640 culture medium containing 0.1% BSA and human leukocyte elastase (Elastin Products Company, Inc.) was then added to the medium so as to have a final concentration of 1 μM. Consequently, a reaction mixture having a final volume of 200 μL was prepared. Subsequently, the reaction mixture was incubated at 37° C. for 1, 3, 10, 30, or 60 minutes. Then, the enzyme reaction was terminated by the addition of phenylmethyl sulfonyl fluoride. The supernatant of each reaction mixture was collected and the concentration of sCD14-ST in the supernatant was then detected by the kit of Example 7-(1). As a result, the concentration of sCD14-ST increased three minutes after the addition of elastase and then gradually decreased.

According to the present invention, there is provided a novel antigen which has the sequence of CD14 in human blood. There is also provided a method for diagnosing or detecting sepsis which is accomplished by assaying the antigen.

The present invention further provides a recombinant soluble fragment which has immunological nature similar to the antigen, a method for producing the recombinant soluble fragment, and a novel antibody which binds to the fragment.

The present invention still further provides an assay kit and an assay method which are capable of assaying various antigens, the kit including as its constituent "an antibody which binds to a peptide comprising a particular amino acid sequence of the human full length soluble CD14 protein"; "an antibody produced by using the peptide comprising a particular amino acid sequence of the human full length soluble CD14 for the antigen"; or "an antibody which binds to the fragment" or a fragment of such antibodies.

The present invention yet further provides a method for screening for an antibody which is effective in assaying the protein.

---

The invention claimed is:

1. A method of diagnosing sepsis comprising the steps of:
   1) contacting a test blood sample with an antibody that detects soluble CD14 antigen by specifically binding to a soluble CD14 antigen, consisting of the amino acid sequence from position 1 to any one of positions 59 to 90 of the amino acid sequence of SEQ ID NO: 3;
   2) comparing an assayed value of soluble CD14 antigen in the test blood sample to a standard value of soluble CD14 antigen in a normal blood sample; and
   3) evaluating whether the assayed value of soluble CD14 antigen observed in said test blood sample is higher than the standard value of soluble CD14 antigen in the normal blood sample;
   wherein said soluble CD14 antigen specifically binds to an antibody which binds to a peptide consisting of the amino acid sequence of SEQ ID NO:2, has no ability to specifically bind to 3C10 antibody, ATCC No. TIB-228 and no ability to bind LPS; and wherein said soluble CD14 antigen has a molecular weight of 13±2 kDa when measured by SDS-PAGE under non-reducing conditions.

2. The method according to claim 1, wherein said step 1) further comprises the steps of:
   determining an assayed value of soluble CD14 antigen in the test blood sample by using a recombinant soluble CD14 fragment as a standard preparation for calibration;
   wherein said recombinant soluble CD14 fragment consists of the amino acid sequence from any one of positions 1 to any one of positions 59 to 90 of the amino acid sequence of SEQ ID NO: 3; specifically binds to an antibody which binds a peptide consisting of the amino acid sequence of SEQ ID NO: 2, has no ability to specifically bind to 3C10 antibody, ATCC No. TIB-288 and has no ability to bind LPS; and has a molecular weight of 13±2 kDa when measured by SDS-PAGE under non-reducing conditions.

* * * * *

SEQUENCE LISTING

```
<160> NUMBER OF SEQ ID NOS: 34

<210> SEQ ID NO 1
<211> LENGTH: 11
<212> TYPE: PRT
<213> ORGANISM: Homo sapiens

<400> SEQUENCE: 1

Thr Thr Pro Glu Pro Cys Glu Leu Asp Asp Glu
1               5                   10

<210> SEQ ID NO 2
<211> LENGTH: 16
<212> TYPE: PRT
<213> ORGANISM: Homo sapiens

<400> SEQUENCE: 2

Arg Val Asp Ala Asp Ala Asp Pro Arg Gln Tyr Ala Asp Thr Val Lys
1               5                   10                  15

<210> SEQ ID NO 3
<211> LENGTH: 356
<212> TYPE: PRT
<213> ORGANISM: Homo sapiens

<400> SEQUENCE: 3

Thr Thr Pro Glu Pro Cys Glu Leu Asp Asp Glu Asp Phe Arg Cys Val
1               5                   10                  15

Cys Asn Phe Ser Glu Pro Gln Pro Asp Trp Ser Glu Ala Phe Gln Cys
            20                  25                  30

Val Ser Ala Val Glu Val Glu Ile His Ala Gly Gly Leu Asn Leu Glu
        35                  40                  45

Pro Phe Leu Lys Arg Val Asp Ala Asp Ala Asp Pro Arg Gln Tyr Ala
    50                  55                  60

Asp Thr Val Lys Ala Leu Arg Val Arg Arg Leu Thr Val Gly Ala Ala
65                  70                  75                  80

Gln Val Pro Ala Gln Leu Leu Val Gly Ala Leu Arg Val Leu Ala Tyr
                85                  90                  95

Ser Arg Leu Lys Glu Leu Thr Leu Glu Asp Leu Lys Ile Thr Gly Thr
                100                 105                 110
```

```
Met Pro Pro Leu Pro Glu Ala Thr Gly Leu Ala Leu Ser Ser Leu
            115                 120                 125

Arg Leu Arg Asn Val Ser Trp Ala Thr Gly Arg Ser Trp Leu Ala Glu
130                 135                 140

Leu Gln Gln Trp Leu Lys Pro Gly Leu Lys Val Leu Ser Ile Ala Gln
145                 150                 155                 160

Ala His Ser Pro Ala Phe Ser Cys Glu Gln Val Arg Ala Phe Pro Ala
                165                 170                 175

Leu Thr Ser Leu Asp Leu Ser Asp Asn Pro Gly Leu Gly Glu Arg Gly
                180                 185                 190

Leu Met Ala Ala Leu Cys Pro His Lys Phe Pro Ala Ile Gln Asn Leu
            195                 200                 205

Ala Leu Arg Asn Thr Gly Ile Glu Thr Pro Thr Gly Val Cys Ala Ala
210                 215                 220

Leu Ala Ala Ala Gly Val Gln Pro His Ser Leu Asp Leu Ser His Asn
225                 230                 235                 240

Ser Leu Arg Ala Thr Val Asn Pro Ser Ala Pro Arg Cys Met Trp Ser
                245                 250                 255

Ser Ala Leu Asn Ser Leu Asn Leu Ser Phe Ala Gly Leu Glu Gln Val
                260                 265                 270

Pro Lys Gly Leu Pro Ala Lys Leu Arg Val Leu Asp Leu Ser Cys Asn
            275                 280                 285

Arg Leu Asn Arg Ala Pro Gln Pro Asp Glu Leu Pro Glu Val Asp Asn
290                 295                 300

Leu Thr Leu Asp Gly Asn Pro Phe Leu Val Pro Gly Thr Ala Leu Pro
305                 310                 315                 320

His Glu Gly Ser Met Asn Ser Gly Val Val Pro Ala Cys Ala Arg Ser
                325                 330                 335

Thr Leu Ser Val Gly Val Ser Gly Thr Leu Val Leu Leu Gln Gly Ala
                340                 345                 350

Arg Gly Phe Ala
        355

<210> SEQ ID NO 4
<211> LENGTH: 17
<212> TYPE: PRT
<213> ORGANISM: Homo sapiens

<400> SEQUENCE: 4

Thr Thr Pro Glu Pro Cys Glu Leu Asp Asp Glu Asp Phe Arg Cys Val
1               5                   10                  15

Cys

<210> SEQ ID NO 5
<211> LENGTH: 19
<212> TYPE: PRT
<213> ORGANISM: Homo sapiens

<400> SEQUENCE: 5

Arg Cys Val Cys Asn Phe Ser Glu Pro Gln Pro Asp Trp Ser Glu Ala
1               5                   10                  15

Phe Gln Cys

<210> SEQ ID NO 6
<211> LENGTH: 68
<212> TYPE: PRT
<213> ORGANISM: Homo sapiens
```

<400> SEQUENCE: 6

Thr Thr Pro Glu Pro Cys Glu Leu Asp Asp Glu Asp Phe Arg Cys Val
1               5                   10                  15

Cys Asn Phe Ser Glu Pro Gln Pro Asp Trp Ser Glu Ala Phe Gln Cys
            20                  25                  30

Val Ser Ala Val Glu Val Glu Ile His Ala Gly Gly Leu Asn Leu Glu
        35                  40                  45

Pro Phe Leu Lys Arg Val Asp Ala Asp Ala Asp Pro Arg Gln Tyr Ala
    50                  55                  60

Asp Thr Val Lys
65

<210> SEQ ID NO 7
<211> LENGTH: 13
<212> TYPE: DNA
<213> ORGANISM: Artificial Sequence
<220> FEATURE:
<223> OTHER INFORMATION: Synthesized DNA (Oligomer:8linkS)

<400> SEQUENCE: 7
agcttaggaa ttt                                                          13

<210> SEQ ID NO 8
<211> LENGTH: 13
<212> TYPE: DNA
<213> ORGANISM: Artificial Sequence
<220> FEATURE:
<223> OTHER INFORMATION: Synthesuzed DNA (Oligomer:8linkA)

<400> SEQUENCE: 8
ctagaaattc cta                                                          13

<210> SEQ ID NO 9
<211> LENGTH: 26
<212> TYPE: DNA
<213> ORGANISM: Artificial Sequence
<220> FEATURE:
<223> OTHER INFORMATION: Synthesized DNA (Sense Primer A)

<400> SEQUENCE: 9
acatctagat gaccacgcca gaacct                                            26

<210> SEQ ID NO 10
<211> LENGTH: 30
<212> TYPE: DNA
<213> ORGANISM: Artificial
<220> FEATURE:
<223> OTHER INFORMATION: Synthesized DNA (Antisense Primer A)

<400> SEQUENCE: 10
tttggatcct tactagagat cgagcaatct                                        30

<210> SEQ ID NO 11
<211> LENGTH: 18
<212> TYPE: DNA
<213> ORGANISM: Artificial Sequence
<220> FEATURE:
<223> OTHER INFORMATION: Synthesized DNA (Sense Primer 1)

<400> SEQUENCE: 11
tttcctacag ctcctggg                                                     18

<210> SEQ ID NO 12

```
<211> LENGTH: 32
<212> TYPE: DNA
<213> ORGANISM: Artificial
<220> FEATURE:
<223> OTHER INFORMATION: Synthesized DNA (Antisense Primer 1)

<400> SEQUENCE: 12
ggggtacctt agtcagcata ctgccgcggg tc                                32

<210> SEQ ID NO 13
<211> LENGTH: 32
<212> TYPE: DNA
<213> ORGANISM: Artificial
<220> FEATURE:
<223> OTHER INFORMATION: Synthesized DNA (Antisense Primer 2)

<400> SEQUENCE: 13
ggggtacctt agagagcctt gaccgtgtca gc                                32

<210> SEQ ID NO 14
<211> LENGTH: 32
<212> TYPE: DNA
<213> ORGANISM: Artificial Sequence
<220> FEATURE:
<223> OTHER INFORMATION: Synthesized DNA (Antisense Primer 3)

<400> SEQUENCE: 14
ggggtacctt agagccgccg cacgcggaga gc                                32

<210> SEQ ID NO 15
<211> LENGTH: 32
<212> TYPE: DNA
<213> ORGANISM: Artificial Sequence
<220> FEATURE:
<223> OTHER INFORMATION: Synthesized DNA (Antisense Primer 4)

<400> SEQUENCE: 15
ggggtacctt atgcggctcc cactgtgagc cg                                32

<210> SEQ ID NO 16
<211> LENGTH: 32
<212> TYPE: DNA
<213> ORGANISM: Artificial Sequence
<220> FEATURE:
<223> OTHER INFORMATION: Synthesized DNA (Antisense Primer 5)

<400> SEQUENCE: 16
ggggtacctt actgagcagg aacctgtgcg gc                                32

<210> SEQ ID NO 17
<211> LENGTH: 32
<212> TYPE: DNA
<213> ORGANISM: Artificial Sequence
<220> FEATURE:
<223> OTHER INFORMATION: Synthesized DNA (Antisense Primer 6)

<400> SEQUENCE: 17
ggggtacctt aggcgcctac cagtagctga gc                                32

<210> SEQ ID NO 18
<211> LENGTH: 32
<212> TYPE: DNA
<213> ORGANISM: Artificial Sequence
<220> FEATURE:
<223> OTHER INFORMATION: Synthesized DNA (Antisense Primer 7)

<400> SEQUENCE: 18
```

```
ggggtacsctt acgctagcac acgcagggcg cc                                32
```

<210> SEQ ID NO 19
<211> LENGTH: 32
<212> TYPE: DNA
<213> ORGANISM: Artificial Sequence
<220> FEATURE:
<223> OTHER INFORMATION: Synthesized DNA (Antisense Primer 8)

<400> SEQUENCE: 19

```
ggggtacsctt acttgaggcg ggagtacgct ag                                32
```

<210> SEQ ID NO 20
<211> LENGTH: 32
<212> TYPE: DNA
<213> ORGANISM: Artificial Sequence
<220> FEATURE:
<223> OTHER INFORMATION: Synthesized DNA (Antisense Primer 9)

<400> SEQUENCE: 20

```
ggggtacsctt actcgagcgt cagttccttg ag                                32
```

<210> SEQ ID NO 21
<211> LENGTH: 32
<212> TYPE: DNA
<213> ORGANISM: Artificial Sequence
<220> FEATURE:
<223> OTHER INFORMATION: Synthesized DNA (Antisense Primer 10)

<400> SEQUENCE: 21

```
ggggtacsctt aggttatctt taggtcctcg ag                                32
```

<210> SEQ ID NO 22
<211> LENGTH: 54
<212> TYPE: DNA
<213> ORGANISM: Artificial Sequence
<220> FEATURE:
<223> OTHER INFORMATION: Synthesized DNA (Sense Primer 2)

<400> SEQUENCE: 22

```
gctctggaag ttctgttcca ggggcccgac acggtcaagg ctctccgcgt gcgg         54
```

<210> SEQ ID NO 23
<211> LENGTH: 54
<212> TYPE: DNA
<213> ORGANISM: Artificial Sequence
<220> FEATURE:
<223> OTHER INFORMATION: Synthesized DNA (Antisense Primer 11)

<400> SEQUENCE: 23

```
gtcgggcccc tggaacagaa cttccagagc atactgccgc gggtcggcgt ccgc         54
```

<210> SEQ ID NO 24
<211> LENGTH: 20
<212> TYPE: DNA
<213> ORGANISM: Artificial Sequence
<220> FEATURE:
<223> OTHER INFORMATION: Synthesized DNA (Antisense Primer 12)

<400> SEQUENCE: 24

```
tctccattcc tgtgttgcgc                                               20
```

<210> SEQ ID NO 25
<211> LENGTH: 30
<212> TYPE: DNA
<213> ORGANISM: Artificial Sequence
<220> FEATURE:

<223> OTHER INFORMATION: Synthesized DNA (Sense Primer 3)

<400> SEQUENCE: 25
ctggttccgc gtggttccga cacggtcaag                                        30

<210> SEQ ID NO 26
<211> LENGTH: 30
<212> TYPE: DNA
<213> ORGANISM: Artificial Sequence
<220> FEATURE:
<223> OTHER INFORMATION: Synthesized DNA (Antisense Primer 13)

<400> SEQUENCE: 26
gaaccacgcg gaaccagagc atactgccgc                                        30

<210> SEQ ID NO 27
<211> LENGTH: 30
<212> TYPE: DNA
<213> ORGANISM: Artificial Sequence
<220> FEATURE:
<223> OTHER INFORMATION: Synthesized DNA (Antisense Primer 14)

<400> SEQUENCE: 27
cgggatcctc aatgatgatg atgatgatgg                                        30

<210> SEQ ID NO 28
<211> LENGTH: 19
<212> TYPE: PRT
<213> ORGANISM: Homo sapiens

<400> SEQUENCE: 28

Met Glu Arg Ala Ser Cys Leu Leu Leu Leu Leu Leu Pro Leu Val His
1               5                   10                  15

Val Ser Ala

<210> SEQ ID NO 29
<211> LENGTH: 14
<212> TYPE: PRT
<213> ORGANISM: Homo sapiens

<400> SEQUENCE: 29

Cys Glu Gly Asn Gly Asn Asn Phe Glu Ser Arg Glu Ala Cys
1               5                   10

<210> SEQ ID NO 30
<211> LENGTH: 8
<212> TYPE: PRT
<213> ORGANISM: Homo sapiens

<400> SEQUENCE: 30

Leu Glu Val Leu Phe Gln Gly Pro
1               5

<210> SEQ ID NO 31
<211> LENGTH: 6
<212> TYPE: PRT
<213> ORGANISM: Homo sapiens

<400> SEQUENCE: 31

Leu Val Pro Arg Gly Ser
1               5

<210> SEQ ID NO 32
<211> LENGTH: 11
<212> TYPE: PRT

```
<213> ORGANISM: Homo sapiens
<220> FEATURE:
<221> NAME/KEY: VARIANT
<222> LOCATION: (6)..(6)
<223> OTHER INFORMATION: Xaa may be Cys, Asn, Ser, Thr, or any of other
      modified aminoacids. However, considering that the peotein
      analyzed is a protein  derived from CD14, it may be Cys. In
      addition, the amino with the reducing alkylation method can reveal
      that Xaa is Cys.

<400> SEQUENCE: 32

Thr Thr Pro Glu Pro Xaa Glu Leu Asp Asp Glu
1               5                   10

<210> SEQ ID NO 33
<211> LENGTH: 4
<212> TYPE: PRT
<213> ORGANISM: Homo sapiens
<220> FEATURE:
<221> NAME/KEY: SITE
<222> LOCATION: (1)..(4)
<223> OTHER INFORMATION: When the predetermined protease in Factor Xa,
      the sequence of the cleavage site.

<400> SEQUENCE: 33

Ile Glu Gly Arg
1

<210> SEQ ID NO 34
<211> LENGTH: 10
<212> TYPE: PRT
<213> ORGANISM: Homo sapiens
<220> FEATURE:
<221> NAME/KEY: BINDING
<222> LOCATION: (1)..(10)
<223> OTHER INFORMATION: F1106-13-3 antibody binds to the region.

<400> SEQUENCE: 34

Cys Asn Phe Ser Glu Pro Gln Pro Asp Trp
1               5                   10
```